(12) United States Patent
Velaparthi et al.

(10) Patent No.: US 8,673,922 B2
(45) Date of Patent: Mar. 18, 2014

(54) AZAINDAZOLE COMPOUNDS

(75) Inventors: Upender Velaparthi, Cheshire, CT (US); David B. Frennesson, Naugatuck, CT (US); Mark G. Saulnier, Higganum, CT (US); Joel F. Austin, Secaucus, NJ (US); Audris Huang, New Hope, PA (US); James Aaron Balog, Lambertville, NJ (US); Dolatrai M. Vyas, Madison, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 0 days.

(21) Appl. No.: 13/814,384

(22) PCT Filed: Jul. 14, 2011

(86) PCT No.: PCT/US2011/043962
§ 371 (c)(1),
(2), (4) Date: Feb. 5, 2013

(87) PCT Pub. No.: WO2012/009510
PCT Pub. Date: Jan. 19, 2012

(65) Prior Publication Data
US 2013/0184254 A1    Jul. 18, 2013

Related U.S. Application Data

(60) Provisional application No. 61/364,589, filed on Jul. 15, 2010.

(51) Int. Cl.
*A01N 43/54*    (2006.01)
*C07D 239/42*    (2006.01)
*C07D 401/04*    (2006.01)

(52) U.S. Cl.
USPC ............ 514/256; 514/303; 544/295; 546/119

(58) Field of Classification Search
USPC ................ 514/256, 303; 544/295; 546/119
See application file for complete search history.

(56) References Cited

U.S. PATENT DOCUMENTS

| | | | |
|---|---|---|---|
| 4,375,467 A * | 3/1983 | Lesher et al. | ................. 514/303 |
| 7,297,709 B2 | 11/2007 | Dai et al. | |
| 7,378,532 B2 | 5/2008 | Kuo et al. | |
| 7,468,376 B2 | 12/2008 | Rosales et al. | |
| 2005/0119278 A1 | 6/2005 | Teng et al. | |
| 2006/0100218 A1 | 5/2006 | Ibrahim et al. | |
| 2006/0178378 A1 | 8/2006 | Dai et al. | |
| 2007/0282101 A1 | 12/2007 | Ericsson et al. | |
| 2009/0030010 A1 | 1/2009 | Schwede et al. | |
| 2011/0105510 A1 | 5/2011 | Ishikawa | |
| 2012/0108589 A1 | 5/2012 | Kitade et al. | |
| 2013/0231354 A1 * | 9/2013 | Austin et al. | ................ 514/259.1 |

FOREIGN PATENT DOCUMENTS

| | | |
|---|---|---|
| WO | WO 03/027094 | 4/2003 |
| WO | WO 2006/004188 | 1/2006 |
| WO | WO 2010/059788 | 5/2010 |
| WO | WO 2010/062506 | 6/2010 |

OTHER PUBLICATIONS

A.M. Traynor et al., Drugs of Today, 40(8), 697-710, 698 (2004).*
Gonzalez, E., et al., "Acylation D'Aminopyrazoles: Formation De Pyrazolo[3,4-b)Pyridines, Pyrazolo[3,4-d]Pyrimidines Et Dipyrazolo[3,4-b:4'3'-e]Pyridines," Tetrahedron, vol. 34, pp. 1175-1178 (1978).
Volochnyuk, D.M., et al., "Electron-Rich Amino Heterocycles for Regiospecific Synthesis of Trifluoromethyl-Containing Fused Pyridines," Synthesis , No. 10, pp. 1531-1540 (2003).
Yap T.A., et al., "Targeting CYP17: established and novel approaches in prostate cancer," Current Opinion in Pharmacology, vol. 8, pp. 449-457 (2008).
International Preliminary Report on Patentability issued Jan. 15, 2013.

* cited by examiner

*Primary Examiner* — James O Wilson
*Assistant Examiner* — Alexander R Pagano
(74) *Attorney, Agent, or Firm* — Gary D. Greenblatt

(57) ABSTRACT

Disclosed are azaindazole compounds of Formula (I), or pharmaceutically acceptable salts thereof, wherein W is $CR^4$ or N; and $R^1$, $R^2$, $R^3$, and $R^4$ are defined herein. Also disclosed are methods of using such compounds in the treatment of at least one CYP17 associated condition, such as, for example, cancer, and pharmaceutical compositions comprising such compounds.

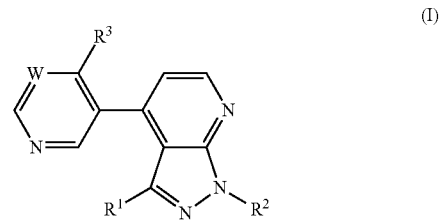

(I)

8 Claims, 1 Drawing Sheet

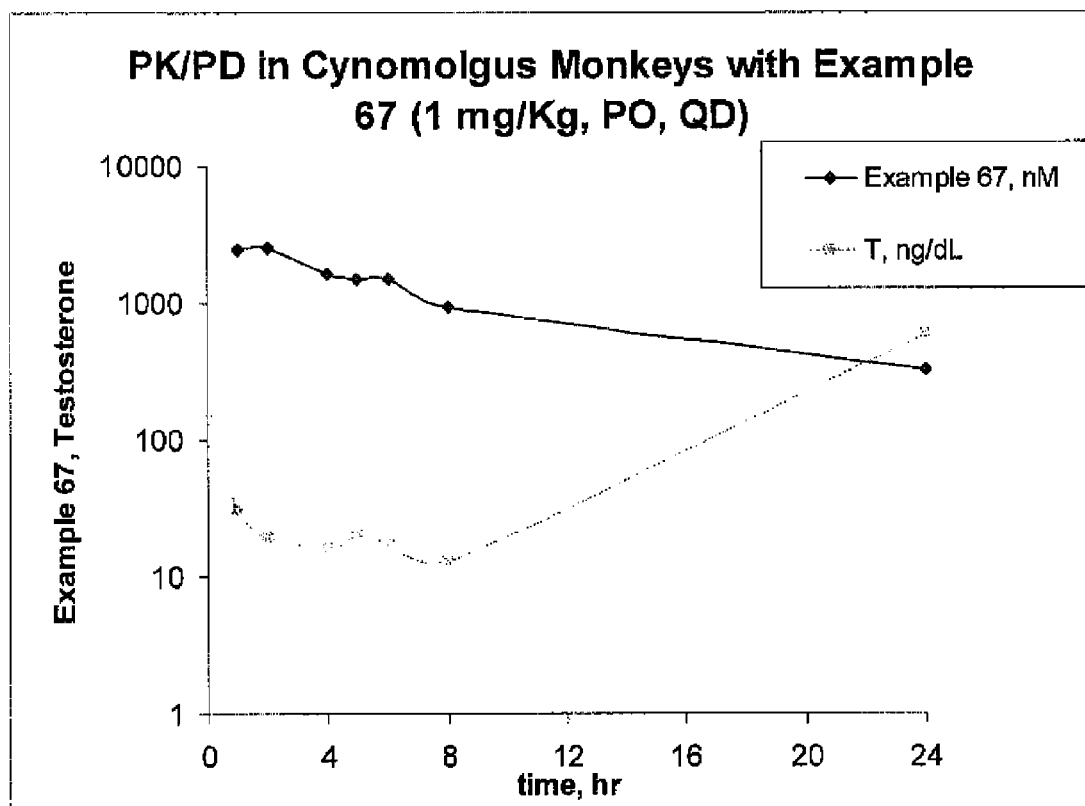

AZAINDAZOLE COMPOUNDS

This application claims the benefit of U.S. Provisional Application Ser. No. 61/364,589 filed Jul. 15, 2010.

FIELD OF THE INVENTION

The present invention generally relates to azaindazole compounds useful as CYP17 inhibitors. Provided herein are azaindazole compounds, compositions comprising such compounds, and methods of their use. The invention further pertains to pharmaceutical compositions comprising at least one compound according to the invention that is useful for the treatment of conditions related to the CYP17 enzyme, such as cancer and other proliferative diseases.

BACKGROUND OF THE INVENTION

Prostate cancer is the second leading cause of cancer related mortality in American men. In 2007, there were 218,890 new cases with 27,000 deaths associated with prostate cancer. It is well known that androgens, such as testosterone and dihydrotestosterone, drive the growth of the prostate as well as prostate cancer at the level of the androgen receptor. The standard of care for advanced hormone sensitive prostate cancer involves surgical or chemical castration with a leutenizing releasing hormone agonist/antagonist to remove the androgens produced in the gonads from circulation. However, approximately 90% of androgens are produced in the testes with the remaining 10% being produced through the action of the adrenal gland. Thus, castration does not alleviate the action of all androgens. Further once a patient progresses to castration resistant prostate cancer, androgens are also produced at the level of the tumor, making treatment with anti-androgens more difficult.

The cytochrome P450 CYP17 is responsible for the biosynthesis of both dihydroepiandrostenedione and androstenedione which are precursors of both androgens and estrogen. Thus the production of all androgens and estrogens produced in the human body is mediated by CYP17. Blocking this enzyme would inhibit the production of gonadal, adrenal and tumoral androgens and could offer a new treatment option for prostate cancer and estrogen receptor-positive breast cancer patients.

Clinical proof-of-concept for CYP17 as a target for prostate cancer has been achieved with the antifungal ketoconazole and the steroidal CYP17 inhibitor abiraterone, which has progressed to Phase III clinical trials for prostate cancer.

There remains a need for compounds that are useful as inhibitors of CYP17 enzymes.

Applicants have found potent compounds that have activity as CYP17 inhibitors. These compounds are provided to be useful as pharmaceuticals with desired stability, bioavailability, therapeutic index, and toxicity values that are important to their drugability.

SUMMARY OF THE INVENTION

The present invention fills the foregoing need by providing azaindazole compounds, which are useful as inhibitors of CYP17 enzymes, including salts and prodrugs thereof.

The present invention also provides pharmaceutical compositions comprising a pharmaceutically acceptable carrier; and at least one compound of Formula (I), or salts or prodrugs thereof.

The present invention also provides a method of treating a disease or disorder associated with the activity of the CYP17 enzyme, the method comprising administering to a mammalian patient a compound of Formula (I) or pharmaceutically acceptable salts or prodrugs thereof.

The present invention also provides processes and intermediates for making the compounds of Formula (I) or salts or prodrugs thereof.

The present invention also provides the compounds of Formula (I), or pharmaceutically acceptable salts or prodrugs thereof, for use in therapy.

The present invention also provides use of a compound of Formula (I) or pharmaceutically acceptable salts or prodrugs thereof, for the manufacture of a medicament for the treatment of cancer.

The compounds of Formula (I) and compositions comprising the compounds are inhibitors of CYP17 enzymes, and may be used in treating, prevention, or curing various CYP17 enzyme related conditions. Pharmaceutical compositions comprising these compounds are useful in treating, preventing, or slowing the progression of diseases or disorders in a variety of therapeutic areas, such as cancer.

These and other features of the invention will be set forth in expanded form as the disclosure continues.

BRIEF DESCRIPTION OF THE DRAWINGS

The invention is illustrated by reference to the accompanying drawing described below.

FIG. 1 shows the plasma pharmacokinetics of Example 67 and plasma levels of testosterone in cynomolgus monkeys. Example 67 was formulated in 80% PEG-400/water at a volume of 1 mL/kg of monkey at a dose of 1 mg/kg. The formulation was then dosed orally at time=0 hours and blood samples were taken over a 24 hour period to monitor for drug exposure and testosterone levels. (♦) Example 67 (nM); (■) testosterone (ng/dL).

DETAILED DESCRIPTION OF THE INVENTION

The first aspect of the invention provides compounds of Formula (I):

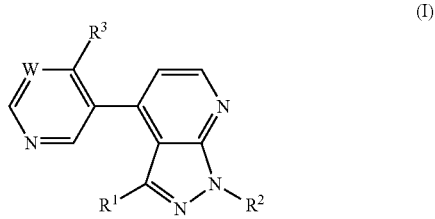

(I)

or pharmaceutically acceptable salts or prodrugs thereof, wherein:

W is CR$^4$ or N;
R$^1$ is H, halo, or C$_{1-6}$alkyl substituted with zero to 4 R$^a$;
R$^2$ is:
  (i) C$_{1-6}$alkyl substituted with zero to 4 R$^a$;
  (ii) C$_{3-6}$ cycloalkyl substituted with zero to 4 R$^a$;
  (iii) aryl substituted with zero to 6 R$^b$;
  (iv) heterocyclyl substituted with zero to 6 R$^c$; or
  (v) heteroaryl substituted with zero to 6 R$^c$;
R$^3$ is:
  (i) H, halo, —CN, —OR$^d$, —NR$^e$R$^e$, or —C(O)OR$^f$;
  (ii) C$_{1-6}$alkyl substituted with zero to 4 R$^a$;
  (iii) C$_{3-6}$ cycloalkyl substituted with zero to 4 R$^a$;
  (iv) aryl substituted with zero to 6 R$^b$;
  (v) heterocyclyl substituted with zero to 6 R$^c$; or
  (vi) heteroaryl substituted with zero to 6 R$^c$;

$R^4$ is:
(i) H, halo, —CN, —OR$^d$, —NR$^e$R$^e$, or —C(O)OR$^f$;
(ii) C$_{1-6}$alkyl substituted with zero to 4 R$^a$; or
(iii) C$_{3-6}$ cycloalkyl substituted with zero to 4 R$^a$;
each R$^a$ is independently halo, —OH, —CN, C$_{3-6}$cycloalkyl, C$_{1-2}$fluoroalkyl, C$_{1-2}$-fluoroalkoxy, morpholinyl, and/or phenyl substituted with zero to 5 R$^b$;
each R$^b$ is independently halo, —OH, —CN, C$_{1-4}$alkyl, C$_{3-6}$cycloalkyl, C$_{1-2}$fluoroalkyl, C$_{1-2}$alkoxy, C$_{1-2}$fluoroalkoxy, —NH$_2$, —NH(CH$_3$), —NH(CH$_2$CF$_3$), —N(CH$_3$)$_2$, —N(CH$_3$)(CH$_2$CF$_3$), —C(O)OH, —S(O)$_2$(C$_{1-4}$alkyl), —S(O)$_2$NR$^f$R$^f$, azetidine, and/or pyrrolidine;
each R$^c$ is independently halo, —CN, —OH, C$_{1-4}$alkyl, C$_{3-6}$cycloalkyl, C$_{1-2}$fluoroalkyl, —OCF$_3$, —OCHF$_2$, —OCH$_2$F, —NH$_2$, —NH(CH$_3$), —NH(CH$_2$CF$_3$), —N(CH$_3$)$_2$, —N(CH$_3$)(CH$_2$CF$_3$), azetidine, and/or pyrrolidine, or two R$^c$ attached to the same atom can form =O;
R$^d$ is:
(i) C$_{1-4}$alkyl substituted with zero to 4 R$^a$;
(ii) C$_{3-6}$ cycloalkyl substituted with zero to 4 R$^a$;
(iii) aryl substituted with zero to 6 R$^b$;
(iv) heterocyclyl substituted with zero to 6 R$^c$; or
(v) heteroaryl substituted with zero to 6 R$^c$;
each R$^e$ is independently:
(i) H;
(ii) C$_{1-4}$alkyl substituted with zero to 4 R$^a$; and/or
(iii) C$_{3-6}$ cycloalkyl substituted with zero to 4 R$^a$; and
each R$^f$ is independently H and/or C$_{1-4}$alkyl;
with the provisos that:
(i) if R$^1$ is H, W is CH, and R$^3$ is —CH$_3$, then R$^2$ is not:

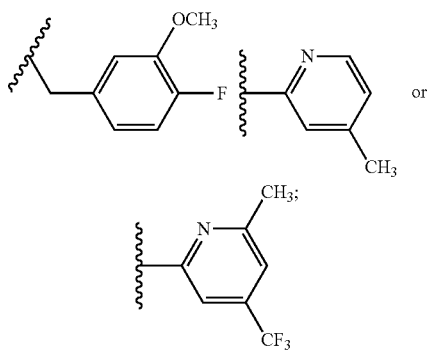

(ii) if R$^1$ is H, W is N, and R$^3$ is CF$_3$, then R$^2$ is not:

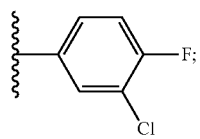 [SMILES: *c1ccc(F)c(Cl)c1]

and
(iii) if R$^1$ is H, W is N, and R$^3$ is —NH$_2$, then R$^2$ is not:

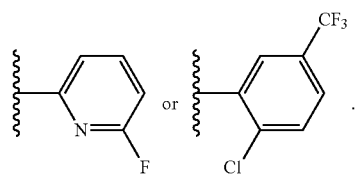

One embodiment provides compounds of Formula (I) or pharmaceutically acceptable salts or prodrugs thereof, wherein:
W is CR$^4$ or N;
R$^1$ is H, F, Cl, or —CH$_3$;
R$^2$ is:
(i) C$_{1-4}$alkyl substituted with zero to 4 R$^a$;
(ii) C$_{4-6}$ cycloalkyl substituted with zero to 2 R$^a$;
(iii) phenyl or naphthalenyl substituted with zero to 6 R$^b$;
(iv) monocyclic heterocyclyl substituted with zero to 4 R$^c$; or
(v) 5- to 6-membered or 9- to 10-membered heteroaryl substituted with zero to 4 R$^e$;
R$^3$ is:
(i) H, F, Cl, Br, —CN, —OR$^d$, —NR$^e$R$^e$, or —C(O)OR$^f$;
(ii) C$_{1-3}$alkyl substituted with zero to 4 R$^a$;
(iii) C$_{3-6}$ cycloalkyl substituted with zero to 2 R$^a$;
(iv) phenyl substituted with zero to 5 R$^b$;
(v) monocyclic heterocyclyl substituted with zero to 5 R$^c$; or
(vi) monocyclic heteroaryl substituted with zero to 3 R$^c$;
R$^4$ is:
(i) H, F, Cl, Br, —CN, —OR$^d$, —NR$^e$R$^e$, or —C(O)OR$^f$;
(ii) C$_{1-3}$alkyl substituted with zero to 4 R$^a$; or
(iii) C$_{3-6}$ cycloalkyl substituted with zero to 2 R$^a$;
each R$^a$ is independently F, Br, —OH, —CN, C$_{3-6}$cycloalkyl, C$_{1-2}$fluoroalkyl, —OCF$_3$, —OCHF$_2$, morpholinyl, and/or phenyl substituted with zero to 3 R$^b$;
each R$^b$ is independently F, Cl, Br, C$_{1-4}$alkyl, C$_{1-2}$fluoroalkyl, C$_{1-2}$alkoxy, —OCF$_3$, —OCHF$_2$, —OCH$_2$F, —NH$_2$, and/or —S(O)$_2$NR$^f$R$^f$;
each R$^c$ is independently F, Cl, Br, —CN, —OH, C$_{1-2}$alkyl, C$_{1-2}$fluoroalkyl, —OCF$_3$, —NH$_2$, —NH(CH$_3$), and/or —N(CH$_3$)$_2$, or two R$^c$ attached to the same atom can form =O;
R$^d$ is C$_{1-2}$alkyl or C$_{1-2}$fluoroalkyl;
each R$^e$ is independently:
(i) H;
(ii) C$_{1-2}$alkyl or C$_{1-2}$fluoroalkyl; and/or
(iii) C$_{3-6}$ cycloalkyl; and
each R$^f$ is independently H and/or C$_{1-2}$alkyl;
with the provisos (i), (ii), and (iii) of the first aspect of the invention hereinabove.

Included in this embodiment are compounds in which W is CR$^4$. Also included in this embodiment are compounds in which W is CH. Furthermore, included in this embodiment are compounds in which W is N.

One embodiment provides compounds of Formula (I) or pharmaceutically acceptable salts or prodrugs thereof, wherein W is CR$^4$. The compounds of this embodiment have the structure of Formula (II):

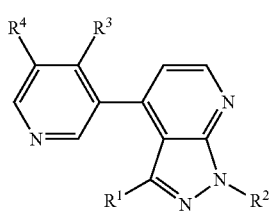

(II)

wherein $R^1$, $R^2$, $R^3$, and $R^4$ are defined in the first aspect of the invention hereinabove, and with the proviso that if $R^1$ is H, $R^4$ is H, and $R^3$ is —$CH_3$, then $R^2$ is not:

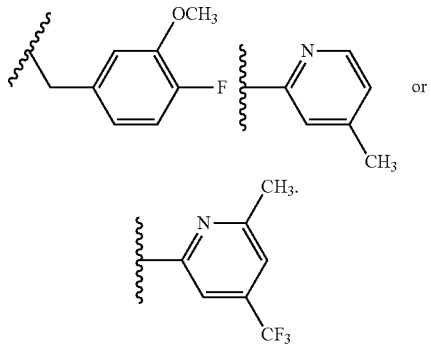

Included in this embodiment are compounds in which $R^1$ is H; $R^2$ is phenyl substituted with zero to 3 $R^b$; $R^4$ is H; $R^3$ is:
(i) H, F, Cl, Br, —CN, —$OR^d$, —$NHR^e$, or —$C(O)OR^f$;
(ii) $C_{1-3}$alkyl substituted with zero to 4 $R^a$;
(iii) $C_{3-6}$ cycloalkyl substituted with zero to 2 $R^a$;
(iv) phenyl substituted with zero to 5 $R^b$;
(v) monocyclic heterocyclyl substituted with zero to 5 $R^c$; or
(vi) monocyclic heteroaryl substituted with zero to 3 $R^c$;

each $R^a$ is independently F, Br, —OH, —CN, $C_{3-6}$cycloalkyl, $C_{1-2}$fluoroalkyl, —$OCF_3$, —$OCHF_2$, morpholinyl, and/or phenyl substituted with zero to 3 $R^b$;

each $R^b$ is independently F, Cl, Br, $C_{1-4}$alkyl, $C_{1-2}$fluoroalkyl, $C_{1-2}$alkoxy, —$OCF_3$, —$OCHF_2$, —$OCH_2F$, —$NH_2$, and/or —$S(O)_2NR^fR^f$;

each $R^c$ is independently F, Cl, Br, —CN, —OH, $C_{1-2}$alkyl, $C_{1-2}$fluoroalkyl, —$OCF_3$, —$NH_2$, —$NH(CH_3)$, and/or —$N(CH_3)_2$, or two $R^c$ attached to the same atom can form =O;

$R^d$ is $C_{1-2}$alkyl or $C_{1-2}$fluoroalkyl;

each $R^e$ is independently:
(i) H;
(ii) $C_{1-2}$alkyl or $C_{1-2}$fluoroalkyl; and/or
(iii) $C_{3-6}$ cycloalkyl; and each $R^f$ is independently H and/or $C_{1-2}$alkyl.

One embodiment provides compounds of Formula (III) or pharmaceutically acceptable salts or prodrugs thereof, wherein W is N. The compounds of this embodiment have the structure of Formula (III):

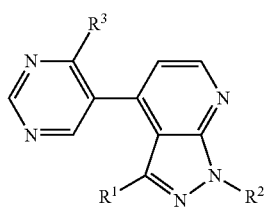

(III)

wherein $R^1$, $R^2$, and $R^3$ are defined in the first aspect of the invention hereinabove, and with the provisos that
(i) if $R^1$ is H and $R^3$ is $CF_3$, then $R^2$ is not:

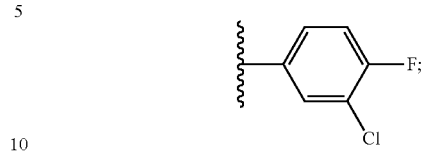

and
(ii) if $R^1$ is H and $R^3$ is —$NH_2$, then $R^2$ is not:

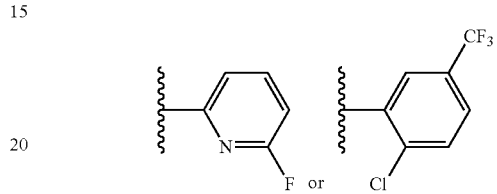

Included in this embodiment are compounds in which $R^1$ is H; $R^2$ is phenyl substituted with zero to 3 $R^b$; $R^3$ is:
(i) H, F, Cl, Br, —CN, —$OR^d$, —$NHR^e$, or —$C(O)OR^f$;
(ii) $C_{1-3}$alkyl substituted with zero to 4 $R^a$;
(iii) $C_{3-6}$ cycloalkyl substituted with zero to 2 $R^a$;
(iv) phenyl substituted with zero to 5 $R^b$;
(v) monocyclic heterocyclyl substituted with zero to 5 $R^c$; or
(vi) monocyclic heteroaryl substituted with zero to 3 $R^c$;

each $R^a$ is independently F, Br, —OH, —CN, $C_{3-6}$cycloalkyl, $C_{1-2}$fluoroalkyl, —$OCF_3$, —$OCHF_2$, morpholinyl, and/or phenyl substituted with zero to 3 $R^b$;

each $R^b$ is independently F, Cl, Br, $C_{1-4}$alkyl, $C_{1-2}$fluoroalkyl, $C_{1-2}$alkoxy, —$OCF_3$, —$OCHF_2$, —$OCH_2F$, —$NH_2$, and/or —$S(O)_2NR^fR^f$;

each $R^c$ is independently F, Cl, Br, —CN, —OH, $C_{1-2}$alkyl, $C_{1-2}$fluoroalkyl, —$OCF_3$, —$NH_2$, —$NH(CH_3)$, and/or —$N(CH_3)_2$, or two $R^c$ attached to the same atom can form =O;

$R^d$ is $C_{1-2}$alkyl or $C_{1-2}$fluoroalkyl;

each $R^e$ is independently:
(i) H;
(ii) $C_{1-2}$alkyl or $C_{1-2}$fluoroalkyl; and/or
(iii) $C_{3-6}$ cycloalkyl; and each $R^f$ is independently H and/or $C_{1-2}$alkyl.

One embodiment provides compounds of Formula (I) or pharmaceutically acceptable salts or prodrugs thereof, wherein $R^1$ is H, F, Cl, or —$CH_3$; preferably, $R^1$ is H, F, or Cl; and more preferably, $R^1$ is H.

One embodiment provides compounds of Formula (I) or pharmaceutically acceptable salts or prodrugs thereof, wherein $R^2$ is:
(i) $C_{1-4}$alkyl substituted with zero to 4 $R^a$;
(ii) $C_{4-6}$ cycloalkyl substituted with zero to 2 $R^a$;
(iii) phenyl or naphthalenyl substituted with zero to 6 $R^b$;
(iv) monocyclic heterocyclyl substituted with zero to 4 $R^c$; or
(v) 5- to 6-membered or 9- to 10-membered heteroaryl substituted with zero to 4 $R^c$;

each $R^a$ is independently F, Br, —OH, —CN, $C_{3-6}$cycloalkyl, $C_{1-2}$fluoroalkyl, —$OCF_3$, —$OCHF_2$, morpholinyl, and/or phenyl substituted with zero to 3 $R^b$;

each $R^b$ is independently F, Cl, Br, $C_{1-4}$alkyl, $C_{1-2}$fluoroalkyl, $C_{1-2}$alkoxy, —$OCF_3$, —$OCHF_2$, —$OCH_2F$, —$NH_2$, and/or —$S(O)_2NR^fR^f$;

each $R^c$ is independently F, Cl, Br, —CN, —OH, $C_{1-2}$alkyl, $C_{1-2}$fluoroalkyl, —OCF$_3$, —NH$_2$, —NH(CH$_3$), and/or —N(CH$_3$)$_2$, or two $R^c$ attached to the same atom can form =O.

Included in this embodiment are compounds in which $R^2$ is:
(i) $C_{1-4}$alkyl substituted with zero to 3 $R^a$;
(ii) $C_{4-6}$ cycloalkyl;
(iii) phenyl substituted with zero to 4 $R^b$;
(iv) tetrahydropyran or tetrahydrothiophenyl substituted with zero to 4 $R^c$; or
(v) oxazolyl, thiazolyl, pyridinyl, or benzothiazolyl, each substituted with zero to 2 $R^c$;

each $R^a$ is independently —OH, cyclohexyl, —CF$_3$, morpholinyl, and/or phenyl substituted with zero to 2 $R^b$;
each $R^b$ is independently F, Cl, Br, $C_{1-3}$alkyl, —CF$_3$, $C_{1-2}$alkoxy, —OCF$_3$, —C(O)OH, and/or —S(O)$_2$NH$_2$;
each $R^c$ is independently F, Cl, Br, —CN, —OH, —CH$_3$, —CF$_3$, or two $R^c$ attached to the same atom can form =O.

Also included in this embodiment are compounds in which $R^2$ is: (i) butyl or $C_{4-6}$cycloalkyl; (ii) $C_{1-2}$alkyl substituted with —OH, —CF$_3$, cyclohexyl, or morpholinyl; (iii) phenyl substituted with zero to 4 substituents independently selected from F, Cl, Br, $C_{1-3}$alkyl, $C_{1-2}$alkoxy, —CF$_3$, —OCF$_3$, —C(O)OH, and/or —S(O)$_2$NH$_2$; (iv) benzyl substituted with zero to 2 substituents independently selected from F, Cl, and/or —OCH$_3$; (v) thiazolyl, oxazolyl, or pyridinyl, each substituted with zero to two substituents independently selected from F, Cl, Br, —CH$_3$, —CF$_3$, and/or —CN; (vi) benzothiazolyl; or (vii) tetrahydropyranyl or tetramethylene sulfonyl.

One embodiment provides compounds of Formula (I) or pharmaceutically acceptable salts or prodrugs thereof, wherein $R^3$ is:
(i) H, F, Cl, Br, —CN, —OR$^d$, —NR$^e$R$^e$, or —C(O)OR$^f$;
(ii) $C_{1-3}$alkyl substituted with zero to 4 $R^a$;
(iii) $C_{3-6}$ cycloalkyl substituted with zero to 2 $R^a$;
(iv) phenyl substituted with zero to 5 $R^b$;
(v) monocyclic heterocyclyl substituted with zero to 5 $R^c$; or
(vi) monocyclic heteroaryl substituted with zero to 3 $R^c$;

each $R^a$ is independently F, Br, —OH, —CN, $C_{3-6}$cycloalkyl, $C_{1-2}$fluoroalkyl, —OCF$_3$, —OCHF$_2$, morpholinyl, and/or phenyl substituted with zero to 3 $R^b$;
each $R^b$ is independently F, Cl, Br, $C_{1-4}$alkyl, $C_{1-2}$fluoroalkyl, $C_{1-2}$alkoxy, —OCF$_3$, —OCHF$_2$, —OCH$_2$F, —NH$_2$, and/or —S(O)$_2$NR$^f$R$^f$;
each $R^c$ is independently F, Cl, Br, —CN, —OH, $C_{1-2}$alkyl, $C_{1-2}$fluoroalkyl, —OCF$_3$, —NH$_2$, —NH(CH$_3$), and/or —N(CH$_3$)$_2$, or two $R^c$ attached to the same atom can form =O;
$R^d$ is $C_{1-2}$alkyl or $C_{1-2}$fluoroalkyl;
each $R^e$ is independently: (i) H; (ii) $C_{1-2}$alkyl or $C_{1-2}$fluoroalkyl; and/or (iii) $C_{3-6}$ cycloalkyl; and
each $R^f$ is independently H and/or $C_{1-2}$alkyl.

Included in this embodiment are compounds in which $R^3$ is:
(i) H, Cl, —OCH$_3$, —OCH$_2$CF$_3$, —NHR$^e$, or —C(O)OCH$_3$;
(ii) —CH$_3$, —CF$_3$, —CHCl$_2$, or —CH$_2$CN; (iii) cyclopropyl;
(iv) oxetanyl, azetidinyl, or morpholinyl, each substituted with zero to 2 $R^c$; or (v) triazolyl; and $R^e$ is H, —CH$_2$CF$_3$, or cyclopropyl. Also included in this embodiment are compounds in which $R^3$ is H, Cl, —CH$_3$, —CF$_3$, —CHCl$_2$, —CH$_2$CN, —OCH$_3$, —OCH$_2$CF$_3$, —NH$_2$, —C(O)OCH$_3$, —NH(cyclopropyl), —NH(CH$_2$CF$_3$), cyclopropyl, morpholinyl, triazolyl, azetidinyl, difluoro azetidinyl, hydroxyazetidinyl, or hydroxy oxetanyl. Furthermore, included in this embodiment are compounds in which $R^3$ is H, Cl, —CH$_3$, —CF$_3$, —CHCl$_2$, —CH$_2$CN, —OCH$_3$, —OCH$_2$CF$_3$, —NH$_2$, —C(O)OCH$_3$, —NH(cyclopropyl), —NH(CH$_2$CF$_3$), cyclopropyl, morpholinyl, triazolyl, azetidinyl, difluoro azetidinyl, hydroxyazetidinyl, or hydroxy oxetanyl.

One embodiment provides compounds of Formula (I) or pharmaceutically acceptable salts or prodrugs thereof, wherein $R^2$ is: $C_{1-4}$alkyl substituted with zero to 4 $R^a$; with the proviso that if $R^1$ is H, W is CH, and $R^3$ is —CH$_3$, then $R^2$ is not:

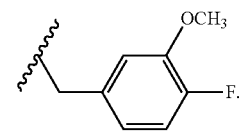 [SMILES: *Cc1ccc(F)c(OC)c1]

Preferably, $R^2$ is $C_{1-4}$alkyl substituted with zero to 3 $R^a$; wherein each $R^a$ is independently F, Br, —OH, —CN, $C_{3-6}$cycloalkyl, $C_{1-2}$fluoroalkyl, —OCF$_3$, —OCHF$_2$, morpholinyl, and/or phenyl substituted with zero to 3 $R^b$; and each $R^b$ is independently F, Cl, Br, $C_{1-4}$alkyl, $C_{1-2}$fluoroalkyl, $C_{1-2}$alkoxy, —OCF$_3$, —OCHF$_2$, —OCH$_2$F, —NH$_2$, and/or —S(O)$_2$NH$_2$. Included in this embodiment are compounds in which $R^2$ is butyl; $C_{1-2}$alkyl substituted with —OH, —CF$_3$, cyclohexyl, or morpholinyl; and benzyl substituted with zero to 2 substituents independently selected from F, Cl, and/or —OCH$_3$.

One embodiment provides compounds of Formula (I) or pharmaceutically acceptable salts or prodrugs thereof, wherein $R^2$ is: $C_{4-6}$ cycloalkyl substituted with zero to 2 $R^a$; wherein each $R^a$ is independently F, Br, —OH, —CN, $C_{3-6}$cycloalkyl, $C_{1-2}$fluoroalkyl, —OCF$_3$, —OCHF$_2$, morpholinyl, and/or phenyl substituted with zero to 3 $R^b$; and each $R^b$ is independently F, Cl, Br, $C_{1-4}$alkyl, $C_{1-2}$fluoroalkyl, $C_{1-2}$alkoxy, —OCF$_3$, —OCHF$_2$, —OCH$_2$F, —NH$_2$, and/or —S(O)$_2$NH$_2$. Included in this embodiment are compounds in which $R^2$ is unsubstituted cyclobutyl, cyclopentyl, or cyclohexyl.

One embodiment provides compounds of Formula (I) or pharmaceutically acceptable salts or prodrugs thereof, wherein $R^2$ is phenyl or naphthalenyl substituted with zero to 6 $R^b$; and each $R^b$ is independently F, Cl, Br, $C_{1-4}$alkyl, $C_{1-2}$fluoroalkyl, $C_{1-2}$alkoxy, —OCF$_3$, —OCHF$_2$, —OCH$_2$F, —NH$_2$, and/or —S(O)$_2$NH$_2$; with the provisos that:
(i) if $R^1$ is H, W is N, and $R^3$ is CF$_3$, then $R^2$ is not:

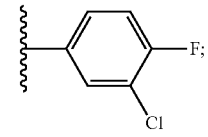 [SMILES: *c1ccc(F)c(Cl)c1]

and
(ii) if $R^1$ is H, W is N, and $R^3$ is —NH$_2$, then $R^2$ is not:

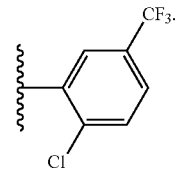 [SMILES: *c1cc(C(F)(F)F)ccc1Cl]

Preferably, $R^2$ is phenyl. Included in this embodiment are compounds of Formula (I) in which $R^2$ is phenyl substituted with zero to 4 $R^b$; wherein each $R^b$ is independently F, Cl, Br, $C_{1-3}$alkyl, —$CF_3$, $C_{1-2}$alkoxy, —$OCF_3$, —C(O)OH, and/or —$S(O)_2NH_2$.

One embodiment provides compounds of Formula (I) or pharmaceutically acceptable salts or prodrugs thereof, wherein $R^1$ is H, F, Cl, or —$CH_3$. Included in this embodiment are compounds in which $R^1$ is H or Cl. Also included are compounds in which $R^1$ is H.

One embodiment provides compounds of Formula (I) or pharmaceutically acceptable salts or prodrugs thereof, wherein $R^2$ is a monocyclic heterocyclyl substituted with zero to 4 $R^c$; and each $R^c$ is independently F, Cl, Br, —CN, —OH, $C_{1-2}$alkyl, $C_{1-2}$fluoroalkyl, —$OCF_3$, —$NH_2$, —$NH(CH_3)$, and/or —$N(CH_3)_2$, or two $R^c$ attached to the same atom can form =O. Included in this embodiment are compounds in which $R^2$ is tetrahydropyran or tetrahydrothiophenyl substituted with zero to 4 $R^c$. Also included in this embodiment are compounds of Formula (I) in which $R^2$ is tetrahydropyranyl or tetramethylene sulfonyl.

One embodiment provides compounds of Formula (I) or pharmaceutically acceptable salts or prodrugs thereof, wherein $R^2$ is: 5- to 6-membered or 9- to 10-membered heteroaryl substituted with zero to 4 $R^c$; and each $R^c$ is independently F, Cl, Br, —CN, —OH, $C_{1-2}$alkyl, $C_{1-2}$fluoroalkyl, —$OCF_3$, —$NH_2$, —$NH(CH_3)$, and/or —$N(CH_3)_2$, or two $R^c$ attached to the same atom can form =O; with the proviso that:
(i) if $R^1$ is H, W is CH, and $R^3$ is —$CH_3$, then $R^2$ is not:

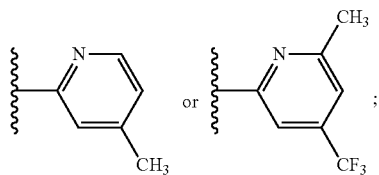

and (ii) if $R^1$ is H, W is N, and $R^3$ is —$NH_2$, then $R^2$ is not:

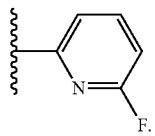

Included in this embodiment are compounds in which $R^2$ is oxazolyl, thiazolyl, pyridinyl, or benzothiazolyl, each substituted with zero to 2 $R^c$. Also included in this embodiment are compounds of Formula (I) in which $R^2$ is thiazolyl, oxazolyl, or pyridinyl, each substituted with zero to two substituents independently selected from F, Cl, Br, —$CH_3$, —$CF_3$, and/or —CN; or benzothiazolyl.

One embodiment provides compounds of Formula (I) or pharmaceutically acceptable salts or prodrugs thereof, wherein $R^2$ is benzyl substituted with zero to 2 substituents independently selected from F, Cl, Br, and/or $C_{1-2}$alkyl; with the proviso that if $R^1$ is H and G is

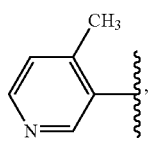

then $R^2$ is not:

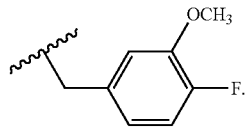 [SMILES: *Cc1ccc(F)c(OC)c1]

Included in this embodiment are compounds in which $R^2$ is benzyl substituted with zero to 2 substituents independently selected from F, Cl, and/or —$OCH_3$.

One embodiment provides compounds of Formula (I) or pharmaceutically acceptable salts or prodrugs thereof, wherein $R^3$ is: H, F, Cl, Br, —CN, —$OR^d$, —$NR^eR^e$, or —$C(O)OR^f$; each $R^e$ is independently H, $C_{1-2}$alkyl, $C_{1-2}$fluoroalkyl; and/or $C_{3-6}$ cycloalkyl; and $R^f$ is H or $C_{1-2}$alkyl. Included in this embodiment are compounds in which $R^3$ is H, Cl, —$OCH_3$, —$OCH_2CF_3$, —$NHR^e$, or —$C(O)OCH_3$. Also included in this embodiment are compounds in which $R^3$ is H, Cl, —$OCH_3$, —$OCH_2CF_3$, —$NH_2$, —NH(cyclopropyl), —$NH(CH_2CF_3)$, or —$C(O)OCH_3$.

One embodiment provides compounds of Formula (I) or pharmaceutically acceptable salts or prodrugs thereof, wherein $R^3$ is $C_{1-3}$alkyl substituted with zero to 4 $R^a$; each $R^a$ is independently F, Br, —OH, —CN, $C_{3-6}$cycloalkyl, $C_{1-2}$fluoroalkyl, —$OCF_3$, —$OCHF_2$, morpholinyl, and/or phenyl substituted with zero to 3 $R^b$; and each $R^b$ is independently F, Cl, Br, $C_{1-4}$alkyl, $C_{1-2}$fluoroalkyl, $C_{1-2}$alkoxy, —$OCF_3$, —$OCHF_2$, —$OCH_2F$, —$NH_2$, and/or —$S(O)_2NH_2$. Included in this embodiment are compounds in which $R^3$ is —$CH_3$, —$CF_3$, —$CHCl_2$, or —$CH_2CN$.

One embodiment provides compounds of Formula (I) or pharmaceutically acceptable salts or prodrugs thereof, wherein $R^3$ is $C_{3-6}$ cycloalkyl substituted with zero to 2 $R^a$; each $R^a$ is independently F, Br, —OH, —CN, $C_{3-6}$cycloalkyl, $C_{1-2}$fluoroalkyl, —$OCF_3$, —$OCHF_2$, morpholinyl, and/or phenyl substituted with zero to 3 $R^b$; and each $R^b$ is independently F, Cl, Br, $C_{1-4}$alkyl, $C_{1-2}$fluoroalkyl, $C_{1-2}$alkoxy, —$OCF_3$, —$OCHF_2$, —$OCH_2F$, —$NH_2$, and/or —$S(O)_2NH_2$. Included in this embodiment are compounds in which $R^3$ is unsubstituted cyclopropyl.

One embodiment provides compounds of Formula (I) or pharmaceutically acceptable salts or prodrugs thereof, wherein $R^3$ is phenyl substituted with zero to 5 $R^b$; and each $R^b$ is independently F, Cl, Br, $C_{1-4}$alkyl, $C_{1-2}$fluoroalkyl, $C_{1-2}$alkoxy, —$OCF_3$, —$OCHF_2$, —$OCH_2F$, —$NH_2$, and/or —$S(O)_2NH_2$. Included in this embodiment are compounds in which $R^3$ is phenyl substituted with zero to 4 $R^b$.

One embodiment provides compounds of Formula (I) or pharmaceutically acceptable salts or prodrugs thereof, wherein $R^3$ is a monocyclic heterocyclyl substituted with zero to 5 $R^c$; and each $R^c$ is independently F, Cl, Br, —CN, —OH, $C_{1-2}$alkyl, $C_{1-2}$fluoroalkyl, —$OCF_3$, —$NH_2$, —$NH(CH_3)$, and/or —$N(CH_3)_2$, or two $R^c$ attached to the same atom can form =O. Included in this embodiment are compounds in which $R^3$ is oxetanyl, azetidinyl, or morpholinyl, each substituted with zero to 2 $R^c$, wherein each $R^c$ is independently F, Cl, Br, —CN, —OH, —$CH_3$, —$CF_3$, or two $R^c$ attached to the same atom can form =O. Also included in this embodiment are compounds in which $R^3$ is morpholinyl, azetidinyl, difluoro azetidinyl, hydroxyazetidinyl, or hydroxy oxetanyl.

One embodiment provides compounds of Formula (I) or pharmaceutically acceptable salts or prodrugs thereof, wherein $R^3$ is a monocyclic heteroaryl substituted with zero to 3 $R^c$. Examples of suitable monocyclic heteroaryls include pyrrolyl, pyrazolyl, pyrazolinyl, imidazolyl, oxazolyl, isoxazolyl, thiazolyl, thiadiazolyl, isothiazolyl, furanyl, thiophenyl, oxadiazolyl, pyridinyl, pyrazinyl, pyrimidinyl, pyridazinyl, and triazolyl. Included in this embodiment are compounds in which $R^3$ is triazolyl.

One embodiment provides compounds of Formula (II) or pharmaceutically acceptable salts or prodrugs thereof, wherein $R^4$ is (i) H, F, Cl, Br, —CN, —$OR^d$, —$NR^eR^e$, or —C(O)$OR^f$; (ii) $C_{1-3}$alkyl substituted with zero to 4 $R^a$; or (iii) $C_{3-6}$ cycloalkyl substituted with zero to 2 $R^a$; wherein $R^d$ is $C_{1-2}$alkyl or $C_{1-2}$fluoroalkyl; each $R^e$ is independently: (i) H; (ii) $C_{1-2}$alkyl or $C_{1-2}$fluoroalkyl; and/or (iii) $C_{3-6}$ cycloalkyl; and each $R^f$ is independently H and/or $C_{1-2}$alkyl. Included in this embodiment are compounds in which $R^4$ is H.

One embodiment provides compounds of Formula (III):

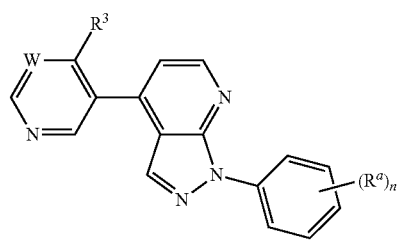

(III)

or pharmaceutically acceptable salts or prodrugs thereof, wherein W is CH or N; each $R^a$ is independently F, Cl, Br, $C_{1-3}$alkyl, $C_{1-2}$alkoxy, —$CF_3$, —$OCF_3$, —C(O)OH, and/or —S(O)$_2$NH$_2$; n is zero, 1, 2, 3, or 4; and $R^3$ is H, Cl, —$CH_3$, —$CF_3$, —$CHCl_2$, —$CH_2CN$, —$OCH_3$, —$OCH_2CF_3$, —$NH_2$, —C(O)$OCH_3$, —NH(cyclopropyl), —NH($CH_2CF_3$), cyclopropyl, morpholinyl, triazolyl, azetidinyl, difluoro azetidinyl, hydroxyazetidinyl, or hydroxy oxetanyl; with the proviso that the following compounds are excluded:

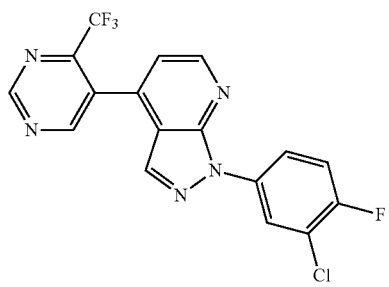

and

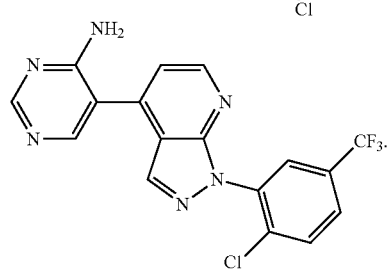

Included in this embodiment are compounds in which each $R^a$ is independently F, Cl, —$CH_3$, —$OCH_3$, —$CF_3$, —$OCF_3$, and/or —S(O)$_2$NH$_2$. Also included in this embodiment are compounds in which each $R^a$ is independently F, Cl, and/or —$CF_3$. Other compounds of this embodiment include compounds in which $R^3$ is —$CH_3$, —$CF_3$, —$NH_2$, or —$OCH_3$.

One embodiment provides compounds of Formula (IV)

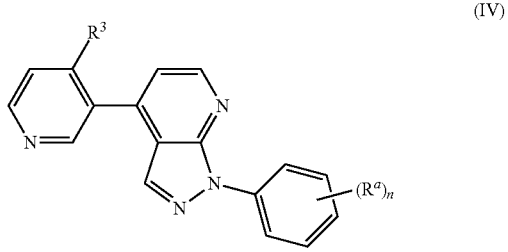

(IV)

or pharmaceutically acceptable salts or prodrugs thereof, wherein each $R^a$ is independently F, Cl, Br, $C_{1-3}$alkyl, $C_{1-2}$alkoxy, —$CF_3$, —$OCF_3$, —C(O)OH, and/or —S(O)$_2$NH$_2$; n is zero, 1, 2, 3, or 4; and $R^3$ is H, Cl, —$CH_3$, —$CF_3$, —$CHCl_2$, —$CH_2CN$, —$OCH_3$, —$OCH_2CF_3$, —$NH_2$, —C(O)$OCH_3$, —NH(cyclopropyl), —NH($CH_2CF_3$), cyclopropyl, morpholinyl, triazolyl, azetidinyl, difluoro azetidinyl, hydroxyazetidinyl, or hydroxy oxetanyl. Included in this embodiment are compounds in which each $R^a$ is independently F, Cl, —$CH_3$, —$OCH_3$, —$CF_3$, —$OCF_3$, and/or —S(O)$_2$NH$_2$. Also included in this embodiment are compounds in which each $R^a$ is independently F, Cl, and/or —$CF_3$. Other compounds of this embodiment include compounds in which $R^3$ is —$CH_3$, —$CF_3$, —$NH_2$, or —$OCH_3$.

One embodiment provides compounds of Formula (V):

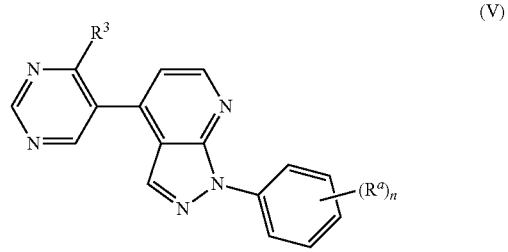

(V)

or pharmaceutically acceptable salts or prodrugs thereof, wherein each $R^a$ is independently F, Cl, Br, $C_{1-3}$alkyl, $C_{1-2}$alkoxy, —$CF_3$, —$OCF_3$, —C(O)OH, and/or —S(O)$_2$NH$_2$; n is zero, 1, 2, 3, or 4; and $R^3$ is H, Cl, —$CH_3$, —$CF_3$, —$CHCl_2$, —$CH_2CN$, —$OCH_3$, —$OCH_2CF_3$, —$NH_2$, —C(O)$OCH_3$, —NH(cyclopropyl), —NH($CH_2CF_3$), cyclopropyl, morpholinyl, triazolyl, azetidinyl, difluoro azetidinyl, hydroxyazetidinyl, or hydroxy oxetanyl, with the proviso that the following compounds are excluded:

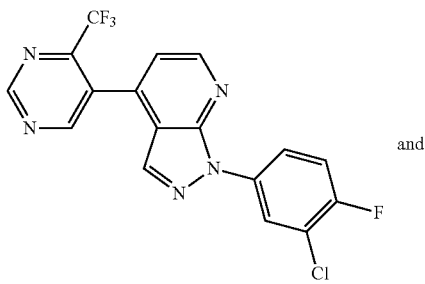

and

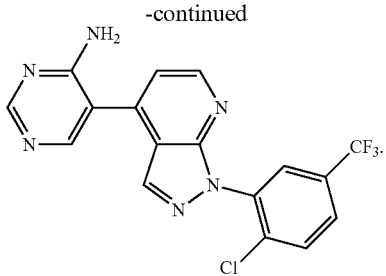

Included in this embodiment are compounds in which each $R^a$ is independently F, Cl, —$CH_3$, —$OCH_3$, —$CF_3$, —$OCF_3$, and/or —$S(O)_2NH_2$. Also included in this embodiment are compounds in which each $R^a$ is independently F, Cl, and/or —$CF_3$. Other compounds of this embodiment include compounds in which $R^3$ is —$CH_3$, —$CF_3$, —$NH_2$, or —$OCH_3$.

One embodiment provides compounds of Formula (VI):

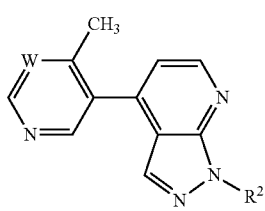

(VI)

or pharmaceutically acceptable salts or prodrugs thereof, wherein W and $R^2$ are defined in the first aspect of the invention hereinabove, with the proviso that if W is CH, then $R^2$ is not:

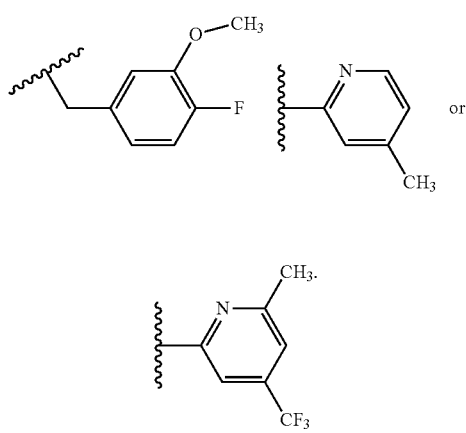

Included in this embodiment are compounds in which $R^2$ is phenyl substituted with zero to 4 substituents independently selected from F, Cl, Br, $C_{1-3}$alkyl, $C_{1-2}$alkoxy, —$CF_3$, —$OCF_3$, —$C(O)OH$, and/or —$S(O)_2NH_2$; or benzyl substituted with zero to 2 substituents independently selected from F, Cl, and/or —$OCH_3$. Also included in this embodiment are compounds in which W is CH. Further, this embodiment includes compounds in which W is N.

One embodiment provides compounds of Formula (VII):

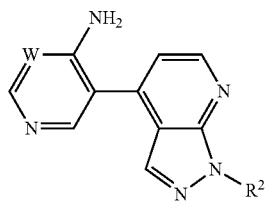

(VII)

or pharmaceutically acceptable salts or prodrugs thereof, wherein W and $R^2$ are defined in the first aspect of the invention hereinabove, with the proviso that if W is N, then $R^2$ is not

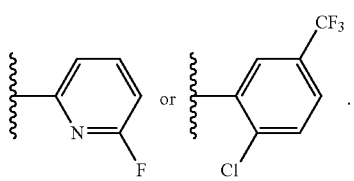

Included in this embodiment are compounds in which $R^2$ is phenyl substituted with zero to 4 substituents independently selected from F, Cl, Br, $C_{1-3}$alkyl, $C_{1-2}$alkoxy, —$CF_3$, —$OCF_3$, —$C(O)OH$, and/or —$S(O)_2NH_2$; or benzyl substituted with zero to 2 substituents independently selected from F, Cl, and/or —$OCH_3$. Also included in this embodiment are compounds in which W is CH. Further, this embodiment includes compounds in which W is N.

One embodiment provides compounds of Formula (VIII)

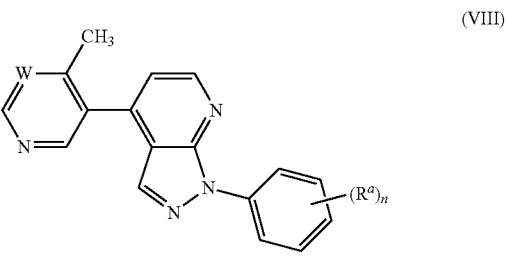

(VIII)

or pharmaceutically acceptable salts or prodrugs thereof, wherein W is CH or N; each $R^a$ is independently F, Cl, Br, $C_{1-3}$alkyl, $C_{1-2}$alkoxy, —$CF_3$, —$OCF_3$, —$C(O)OH$, and/or —$S(O)_2NH_2$; and n is zero, 1, 2, 3, or 4. Included in this embodiment are compounds in which each $R^a$ is independently F, Cl, —$CH_3$, —$OCH_3$, —$CF_3$, —$OCF_3$, and/or —$S(O)_2NH_2$. Also included in this embodiment are compounds in which each $R^a$ is independently F, Cl, and/or —$CF_3$. Also included in this embodiment are compounds in which W is CH. Further, this embodiment includes compounds in which W is N.

One embodiment provides compounds of Formula (IX)

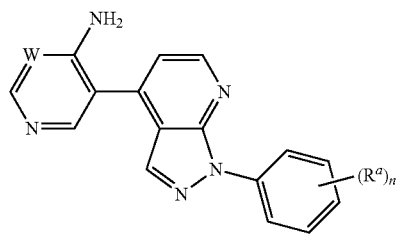
(IX)

or pharmaceutically acceptable salts or prodrugs thereof, wherein W is CH or N; each $R^a$ is independently F, Cl, Br, $C_{1-3}$alkyl, $C_{1-2}$alkoxy, —$CF_3$, —$OCF_3$, —C(O)OH, and/or —$S(O)_2NH_2$; and n is zero, 1, 2, 3, or 4, with the proviso that the following compound is excluded:

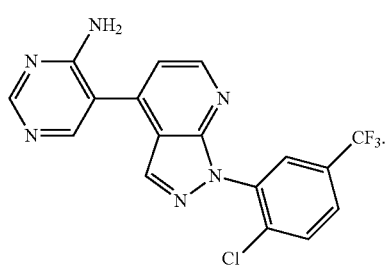 [SMILES: Nc1ncncc1-c1ccnc2c1cnn2-c1cc(C(F)(F)F)ccc1Cl]

Included in this embodiment are compounds in which each $R^a$ is independently F, Cl, —$CH_3$, —$OCH_3$, —$CF_3$, —$OCF_3$, and/or —$S(O)_2NH_2$. Also included in this embodiment are compounds in which each $R^a$ is independently F, Cl, and/or —$CF_3$. Also included in this embodiment are compounds in which W is CH. Further, this embodiment includes compounds in which W is N.

One embodiment provides compounds of Formula (X)

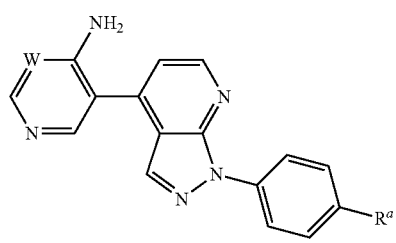
(X)

or pharmaceutically acceptable salts or prodrugs thereof, wherein $R^a$ is F, Cl, or —$CF_3$. Included in this embodiment are compounds of Formula (XI):

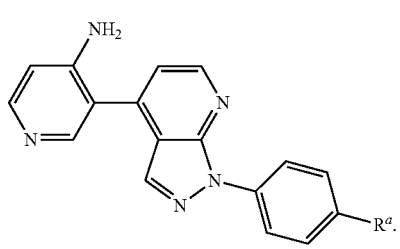
(XI)

Also, included in this embodiment are compounds of Formula (XII):

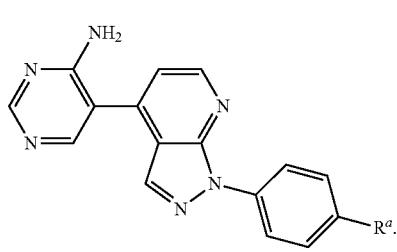
(XII)

One embodiment provides compounds of Formula (XIII)

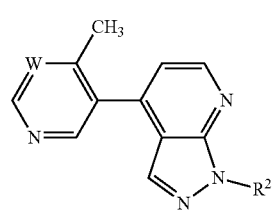
(XIII)

or pharmaceutically acceptable salts or prodrugs thereof, wherein W is CH or N; and $R^2$ is

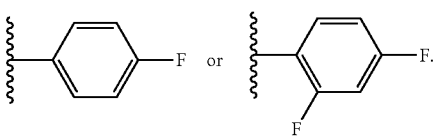 [SMILES: *c1ccc(F)cc1 ; *c1ccc(F)cc1F]

One embodiment provides compounds of Formula (XIV)

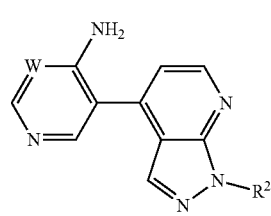
(XIV)

or pharmaceutically acceptable salts or prodrugs thereof, wherein W is CH or N; and $R^2$ is

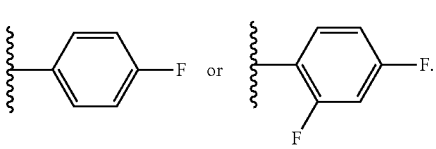

One embodiment provides compounds of Formula (XV)

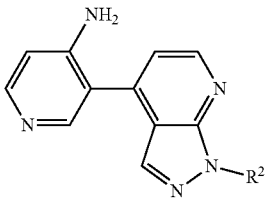

or pharmaceutically acceptable salts or prodrugs thereof, wherein W is CH or N; and R² is

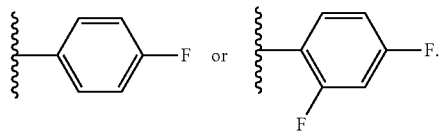

One embodiment provides compounds of Formula (XVI)

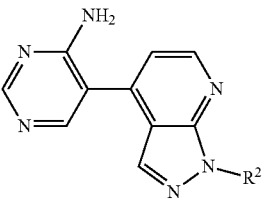

or pharmaceutically acceptable salts or prodrugs thereof, wherein W is CH or N; and R² is

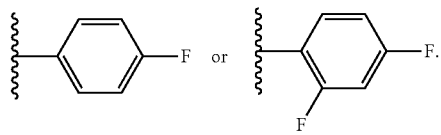

One embodiment provides a compound of Formula (I) or a pharmaceutically acceptable salt or a prodrug thereof, wherein said compound is selected:

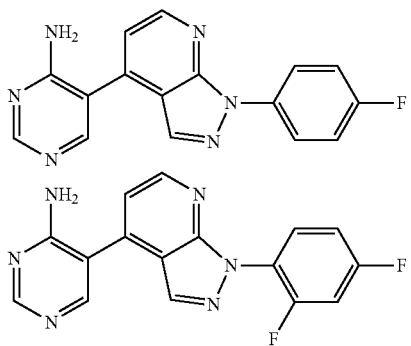

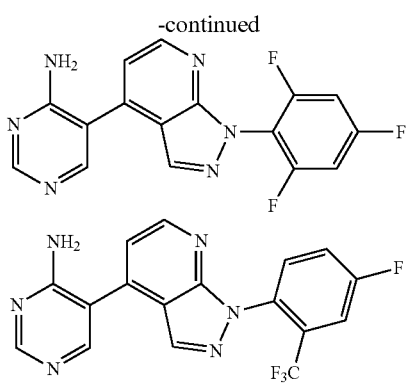

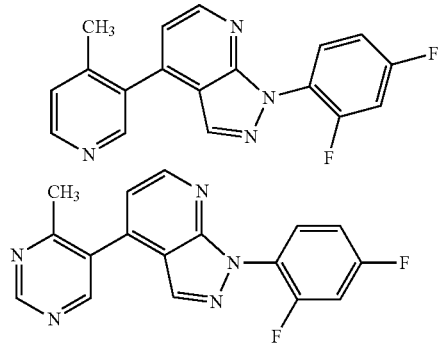

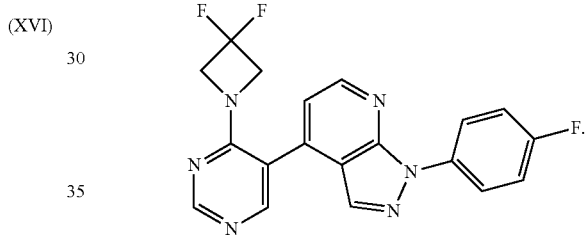

One embodiment provides a compound of Formula (I) or a pharmaceutically acceptable salt or a prodrug thereof, wherein said compound is selected from 3-(4-(4-methoxypyridin-3-yl)-1H-pyrazolo[3,4-b]pyridin-1-yl)benzenesulfonamide (1); 1-(4-fluorophenyl)-4-(4-methylpyridin-3-yl)-1H-pyrazolo[3,4-b]pyridine (3); 1-(4-fluorophenyl)-4-(4-(trifluoromethyl)pyridin-3-yl)-1H-pyrazolo[3,4-b]pyridine (5); 1-(4-fluorophenyl)-4-(4-methoxypyridin-3-yl)-1H-pyrazolo[3,4-b]pyridine (6); 3-(3-(1-(4-fluorophenyl)-1H-pyrazolo[3,4-b]pyridin-4-yl)pyridin-4-yl)oxetan-3-ol (9); 4-(4-chloropyridin-3-yl)-1-(4-fluorophenyl)-1H-pyrazolo[3,4-b]pyridine (10); 1-(4-fluorophenyl)-4-(pyridin-3-yl)-1H-pyrazolo[3,4-b]pyridine (11); methyl 3-(1-(4-fluorophenyl)-1H-pyrazolo[3,4-b]pyridin-4-yl)isonicotinate (12); 1-(2,4-difluorophenyl)-4-(4-methylpyridin-3-yl)-1H-pyrazolo[3,4-b]pyridine (13); 4-(4-methylpyridin-3-yl)-1-(pyridin-2-yl)-1H-pyrazolo[3,4-b]pyridine (14); 1-(2,5-dichlorophenyl)-4-(4-methylpyridin-3-yl)-1H-pyrazolo[3,4-b]pyridine (15); 4-(4-methylpyridin-3-yl)-1-(2,4,6-trifluorophenyl)-1H-pyrazolo[3,4-b]pyridine (16); 1-(2,5-difluorophenyl)-4-(4-methylpyridin-3-yl)-1H-pyrazolo[3,4-b]pyridine (17); 1-(3-chloro-4-fluorophenyl)-4-(4-methylpyridin-3-yl)-1H-pyrazolo[3,4-b]pyridine (18); 1-(2-chloro-5-(trifluoromethyl)phenyl)-4-(4-methylpyridin-3-yl)-1H-pyrazolo[3,4-b]pyridine (19); 1-(3-fluoro-2-methoxyphenyl)-4-(4-methylpyridin-3-yl)-1H-pyrazolo[3,4-b]pyridine (20); 1-tert-butyl-4-(4-methylpyridin-3-yl)-1H-pyrazolo[3,4-b]pyridine (21); 3-(4-(4-methylpyridin-3-yl)-1H-pyrazolo[3,4-b]pyridin-1-yl)benzoic acid (22); 4-(4- methylpyridin-3-yl)-1-(3-(trifluoromethyl)pyridin-2-yl)-1H-pyrazolo[3,4-b]pyridine (23); 1-(cyclohexylmethyl)-4-(4-methylpyridin-3-yl)-1H-pyrazolo[3,4-b]pyridine (24); 1-(3-chloropyridin-2-yl)-4-(4-methylpyridin-3-yl)-1H-pyrazolo[3,4-b]pyridine (25); 1-(3-chloro-2-methylphenyl)-4-(4-methylpyridin-3-yl)-1H-pyrazolo[3,4-b]pyridine (26); 1-cyclohexyl-4-(4-methylpyridin-3-yl)-1H-pyrazolo[3,4-b]pyridine (27); 1-isobutyl-4-(4-methylpyridin-3-yl)-1H-pyrazolo[3,4-b]pyridine (28); 1-(4-fluorobenzyl)-4-(4-methylpyridin-3-yl)-1H-pyrazolo[3,4-b]pyridine (29); 1-(3-chloro-5-fluorophenyl)-4-(4-methylpyridin-3-yl)-1H-pyrazolo[3,4-b]pyridine (30); 4-(2-(4-(4-methylpyridin-3-yl)-1H-pyrazolo[3,4-b]pyridin-1-yl)ethyl) morpholine (31); 1-(5-chloropyridin-2-yl)-4-(4-methylpyridin-3-yl)-1H-pyrazolo[3,4-b]pyridine (32); 4-(4-methylpyridin-3-yl)-1-(tetrahydro-2H-pyran-4-yl)-1H-pyrazolo[3,4-b]pyridine (33); 2-(4-(4-methylpyridin-3-yl)-1H-pyrazolo[3,4-b]pyridin-1-yl)benzo[d]thiazole (34); 4-(4-methylpyridin-3-yl)-1-(2-(trifluoromethyl)phenyl)-1H-pyrazolo[3,4-b]pyridine (35); 4-(4-methylpyridin-3-yl)-1-(2-methylpyridin-4-yl)-1H-pyrazolo[3,4-b]pyridine (36); 1-cyclobutyl-4-(4-methylpyridin-3-yl)-1H-pyrazolo[3,4-b]pyridine (37); 1-(6-fluoropyridin-2-yl)-4-(4-methylpyridin-3-yl)-1H-pyrazolo[3,4-b]pyridine (38); 4-(4-methylpyridin-3-yl)-1-(5-(trifluoromethyl)pyridin-2-yl)-1H-pyrazolo[3,4-b]pyridine (39); 2-methyl-5-(4-(4-methylpyridin-3-yl)-1H-pyrazolo[3,4-b]pyridin-1-yl)oxazole-4-carbonitrile (40); 1-(3-methoxyphenyl)-4-(4-methylpyridin-3-yl)-1H-pyrazolo[3,4-b]pyridine (41); 1-(4-methoxybenzyl)-4-(4-methylpyridin-3-yl)-1H-pyrazolo[3,4-b]pyridine (42); 1-(2-methoxybenzyl)-4-(4-methylpyridin-3-yl)-1H-pyrazolo[3,4-b]pyridine (43); 1-(3-methoxybenzyl)-4-(4-methylpyridin-3-yl)-1H-pyrazolo[3,4-b]pyridine (44); 1-benzyl-4-(4-methylpyridin-3-yl)-1H-pyrazolo[3,4-b]pyridine (45); 1-(3-bromopyridin-2-yl)-4-(4-methylpyridin-3-yl)-1H-pyrazolo[3,4-b]pyridine (46); 4-(4-methylpyridin-3-yl)-1-o-tolyl-1H-pyrazolo[3,4-b]pyridine (47); 1-(2-methoxyphenyl)-4-(4-methylpyridin-3-yl)-1H-pyrazolo[3,4-b]pyridine (48); 4-(4-(4-methylpyridin-3-yl)-1H-pyrazolo[3,4-b]pyridin-1-yl)benzenesulfonamide (49); 1-(5-fluoro-2-methylphenyl)-4-(4-methylpyridin-3-yl)-1H-pyrazolo[3,4-b]pyridine (50); 4-(4-methylpyridin-3-yl)-1-(3-(trifluoromethyl)phenyl)-1H-pyrazolo[3,4-b]pyridine (51); 1-(3,4-difluorophenyl)-4-(4-methylpyridin-3-yl)-1H-pyrazolo[3,4-b]pyridine (52); 1-(2-isopropylphenyl)-4-(4-methylpyridin-3-yl)-1H-pyrazolo[3,4-b]pyridine (53); 1-(2-ethoxyphenyl)-4-(4-methylpyridin-3-yl)-1H-pyrazolo[3,4-b]pyridine (54); 1-(2-chloro-6-fluorobenzyl)-4-(4-methylpyridin-3-yl)-1H-pyrazolo[3,4-b]pyridine (55); 1-(1,1-dioxidotetrahydrothiophen-3-yl)-4-(4-methylpyridin-3-yl)-1H-pyrazolo[3,4-b]pyridine (56); 1-(2,6-difluorophenyl)-4-(4-methylpyridin-3-yl)-1H-pyrazolo[3,4-b]pyridine (57); 1-(5-chloro-2-fluorophenyl)-4-(4-methylpyridin-3-yl)-1H-pyrazolo[3,4-b]pyridine (58); 1-(2-bromophenyl)-4-(4-methylpyridin-3-yl)-1H-pyrazolo[3,4-b]pyridine (59); 1-(3-bromophenyl)-4-(4-methylpyridin-3-yl)-1H-pyrazolo[3,4-b]pyridine (60); 4-(4-(dichloromethyl)pyridin-3-yl)-1-(2,4-difluorophenyl)-1H-pyrazolo[3,4-b]pyridine (61); 3-(1-(2,4-difluorophenyl)-1H-pyrazolo[3,4-b]pyridin-4-yl)pyridin-4-amine (62): 2-(3-(1-(2,4-difluorophenyl)-1H-pyrazolo[3,4-b]pyridin-4-yl)pyridin-4-yl)acetonitrile (63); 4-(4-(Azetidin-1-yl)pyridin-3-yl)-1-(2,4-difluorophenyl)-1H-pyrazolo[3,4-b]pyridine (65); 3-(4-(4-aminopyridin-3-yl)-1H-pyrazolo[3,4-b]pyridin-1-yl)benzenesulfonamide (79); 3-(4-(4-methylpyridin-3-yl)-1H-pyrazolo[3,4-b]pyridin-1-yl)benzenesulfonamide (80); 1-(3-fluorophenyl)-4-(4-methylpyridin-3-yl)-1H-pyrazolo[3,4-b]pyridine (81); 1-(2-chloro-4-fluorophenyl)-4-(4-methylpyridin-3-yl)-1H-pyrazolo[3,4-b]pyridine (82); 2-(4-(4-methylpyridin-3-yl)-1H-pyrazolo[3,4-b]pyridin-1-yl)ethanol (83); 4-(4-methylpyridin-3-yl)-1-(2,2,2-trifluoroethyl)-1H-pyrazolo[3,4-b]pyridine (84); 4-(4-methylpyridin-3-yl)-1-phenyl-1H-pyrazolo[3,4-b]pyridine (85); 1-(5-methylpyridin-2-yl)-4-(4-methylpyridin-3-yl)-1H-pyrazolo[3,4-b]pyridine (86); 2-(4-(4-methylpyridin-3-yl)-1H-pyrazolo[3,4-b]pyridin-1-yl)thiazole (87); and 4-methyl-2-(4-(4-methylpyridin-3-yl)-1H-pyrazolo[3,4-b]pyridin-1-yl)thiazole (88).

One embodiment provides a compound of Formula (I) or a pharmaceutically acceptable salt or a prodrug thereof, wherein said compound is selected from 1-(4-fluorophenyl)-4-(4-methylpyrimidin-5-yl)-1H-pyrazolo[3,4-b]pyridine (2); 3-(4-(4-aminopyrimidin-5-yl)-1H-pyrazolo[3,4-b]pyridin-1-yl)benzenesulfonamide (4); 4-(4-cyclopropylpyrimidin-5-yl)-1-(4-fluorophenyl)-1H-pyrazolo[3,4-b]pyridine (7); 5-(1-(4-fluorophenyl)-1H-pyrazolo[3,4-b]pyridin-4-yl)pyrimidin-4-amine (8); 1-(2,4-difluorophenyl)-4-(4-methylpyrimidin-5-yl)-1H-pyrazolo[3,4-b]pyridine (64); 4-(4-(azetidin-1-yl)pyrimidin-5-yl)-1-(2,4-difluorophenyl)-1H-pyrazolo[3,4-b]pyridine (66); 5-(1-(2,4-difluorophenyl)-1H-pyrazolo[3,4-b]pyridin-4-yl)pyrimidin-4-amine (67); 1-(5-(1-(2,4-difluorophenyl)-1H-pyrazolo[3,4-b]pyridin-4-yl)pyrimidin-4-yl)azetidin-3-ol (68); 5-(1-(2,3,5,6-tetrafluorophenyl)-1H-pyrazolo[3,4-b]pyridin-4-yl)pyrimidin-4-amine (69); 5-(1-(2,3,4-trifluorophenyl)-1H-pyrazolo[3,4-b]pyridin-4-yl)pyrimidin-4-amine (70); 5-(1-(3-bromopyridin-2-yl)-1H-pyrazolo[3,4-b]pyridin-4-yl)pyrimidin-4-amine (71); 5-(1-(pyridin-2-yl)-1H-pyrazolo[3,4-b]pyridin-4-yl)pyrimidin-4-amine (72); 5-(1-(3-(trifluoromethyl)pyridin-2-yl)-1H-pyrazolo[3,4-b]pyridin-4-yl)pyrimidin-4-amine (73); 5-(1-(2,6-difluorophenyl)-1H-pyrazolo[3,4-b]pyridin-4-yl)pyrimidin-4-amine (74); 5-(1-(3-chloro-5-fluorophenyl)-1H-pyrazolo[3,4-b]pyridin-4-yl)pyrimidin-4-amine (75); 5-(1-(2-(trifluoromethyl)phenyl)-1H-pyrazolo[3,4-b]pyridin-4-yl)pyrimidin-4-amine (76); 5-(1-(2,4,6-trifluorophenyl)-1H-pyrazolo[3,4-b]pyridin-4-yl)pyrimidin-4-amine (77); 5-(1-(2-chloro-4-fluorophenyl)-1H-pyrazolo[3,4-b]pyridin-4-yl)pyrimidin-4-amine (78); N-cyclopropyl-5-(1-(4-fluorophenyl)-1H-pyrazolo[3,4-b]pyridin-4-yl)pyrimidin-4-amine (89); 5-(1-(2,4-difluorophenyl)-1H-pyrazolo[3,4-b]pyridin-4-yl)-N-(2,2,2-trifluoroethyl) pyrimidin-4-amine (90); 4-(4-(2 H-1,2,3-triazol-2-yl)pyrimidin-5-yl)-1-(2,4-difluorophenyl)-1H-pyrazolo[3,4-b]pyridine (91); 5-3-chloro-1-(4-fluorophenyl)-1H-pyrazolo[3,4-b]pyridin-4-yl)pyrimidin-4-amine (92); 1-(2,4-difluorophenyl)-4-(4-(trifluoromethyl)pyrimidin-5-yl)-1H-pyrazolo[3,4-b]pyridine (93); 5-(1-(2-methoxyphenyl)-1H-pyrazolo[3,4-b]pyridin-4-yl)-4-pyrimidinamine (94); 5-(1-(3,4-difluorophenyl)-1H-pyrazolo[3,4-b]pyridin-4-yl)-4-pyrimidinamine (95); 5-(1-(3-chloro-4-fluorophenyl)-1H-pyrazolo[3,4-b]pyridin-4-yl)-4-pyrimidinamine (96); 5-(1-(2,5-difluorophenyl)-1H-pyrazolo[3,4-b]pyridin-4-yl)-4-pyrimidinamine (97); 5-(1-(2-(trifluoromethoxy)phenyl)-1H-pyrazolo[3,4-b]pyridin-4-yl)-4-pyrimidinamine (98); 1-(4-fluorophenyl)-4-(4-(trifluoromethyl)-5-pyrimidinyl)-1H-pyrazolo[3,4-b]pyridine (99); 1-(3,4-difluorophenyl)-4-(4-(trifluoromethyl)-5-pyrimidinyl)-1H-pyrazolo[3,4-b]pyridine (100); 1-(2,5-difluorophenyl)-4-(4-(trifluoromethyl)-5-pyrimidinyl)-1H-pyrazolo[3,4-b]pyridine (101); 4-(4-(3,3-difluoroazetidin-1-yl)pyrimidin-5-yl)-1-(4-fluorophenyl)-1H-pyrazolo[3,4-b]pyridine (102); 4-(4-(3,3-difluoroazetidin-1-yl)pyrimidin-5-yl)-1-(2,4-difluorophenyl)-1H-pyrazolo[3,4-b]pyridine (103); 5-(1-(4-fluoro-2-(trifluoromethyl)phenyl)-1H-pyrazolo[3,4-b]pyridin-4-yl)pyrimidin-4-amine (104); 4-(5-(1-(4-fluorophenyl)- 1H-pyrazolo[3,4-b]pyridin-4-yl)pyrimidin-4- yl)morpholine (105); 1-(4-fluorophenyl)-4-(4-(2,2,2-trifluoroethoxy)pyrimidin-5-yl)-1H-pyrazolo[3,4-b]pyridine (106); 5-(1-(4-fluorophenyl)-1H-pyrazolo[3,4-b]pyridin-4-yl)-N-(2,2,2-trifluoroethyl) pyrimidin-4-amine (107); and N-cyclopropyl-5-(1-(2,4-difluorophenyl)-1H-pyrazolo[3,4-b]pyridin-4-yl)pyrimidin-4-amine (108).

Definitions

The features and advantages of the invention may be more readily understood by those of ordinary skill in the art upon reading the following detailed description. It is to be appreciated that certain features of the invention that are, for clarity reasons, described above and below in the context of separate embodiments, may also be combined to form a single embodiment. Conversely, various features of the invention that are, for brevity reasons, described in the context of a single embodiment, may also be combined so as to form sub-combinations thereof. Embodiments identified herein as exemplary or preferred are intended to be illustrative and not limiting.

Unless specifically stated otherwise herein, references made in the singular may also include the plural. For example, "a" and "an" may refer to either one, or one or more.

Unless otherwise indicated, any heteroatom with unsatisfied valences is assumed to have hydrogen atoms sufficient to satisfy the valences.

The definitions set forth herein take precedence over definitions set forth in any patent, patent application, and/or patent application publication incorporated herein by reference.

Listed below are definitions of various terms used to describe the present invention. These definitions apply to the terms as they are used throughout the specification (unless they are otherwise limited in specific instances) either individually or as part of a larger group.

Throughout the specification, groups and substituents thereof may be chosen by one skilled in the field to provide stable moieties and compounds.

In accordance with a convention used in the art,

is used in structural formulas herein to depict the bond that is the point of attachment of the moiety or substituent to the core or backbone structure.

The terms "halo" and "halogen," as used herein, refer to F, Cl, Br, and I.

The term "alkyl" as used herein, refers to both branched and straight-chain saturated aliphatic hydrocarbon groups containing, for example, from 1 to 12 carbon atoms, from 1 to 6 carbon atoms, and from 1 to 4 carbon atoms. Examples of alkyl groups include, but are not limited to, methyl (Me), ethyl (Et), propyl (e.g., n-propyl and i-propyl), butyl (e.g., n-butyl, i-butyl, sec-butyl, and t-butyl), and pentyl (e.g., n-pentyl, isopentyl, neopentyl), n-hexyl, 2-methylpentyl, 2-ethylbutyl, 3-methylpentyl, and 4-methylpentyl. When numbers appear in a subscript after the symbol "C", the subscript defines with more specificity the number of carbon atoms that a particular group may contain. For example, "$C_1$-$C_6$ alkyl" denotes straight and branched chain alkyl groups with one to six carbon atoms.

The term "haloalkyl," as used herein, refers to an alkyl group in which one or more hydrogen atoms are replaced by halogen atom(s), the number of which can range from one up to the total number of hydrogen atoms that could otherwise exist in the parent alkyl group. Representative examples of haloalkyl groups include, but are not limited to, chloromethyl (—$CH_2Cl$), trifluoromethyl (—$CF_3$—, and 2,2,2-trifluoroethyl (—$CH_2CF_3$). When numbers appear in a subscript after the symbol "C", the subscript defines with more specificity the number of carbon atoms that a particular haloalkyl group may contain. For example, "$C_1$-$C_4$ haloalkyl" denotes straight and branched chain haloalkyl groups with one to four carbon atoms.

The term "fluoroalkyl" as used herein is intended to include both branched and straight-chain saturated aliphatic hydrocarbon groups substituted with one or more fluorine atoms. For example, "$C_{1-4}$ fluoroalkyl" is intended to include $C_1$, $C_2$, $C_3$, and $C_4$ alkyl groups substituted with one or more fluorine atoms. Representative examples of fluoroalkyl groups include, but are not limited to, —$CF_3$ and —$CH_2CF_3$.

The term "chloroalkyl" as used herein is intended to include both branched and straight-chain saturated aliphatic hydrocarbon groups substituted with one or more chlorine atoms. For example, "$C_{1-4}$ chloroalkyl" is intended to include $C_1$, $C_2$, $C_3$, and $C_4$ alkyl groups substituted with one or more chlorine atoms. Representative examples of chloroalkyl groups include, but are not limited to, —$CCl_3$ and —$CH_2CCl_3$.

The term "cyano" refers to the group —CN.

The term "cyanoalkyl" includes both branched and straight-chain saturated alkyl groups substituted with one or more cyano groups. For example, "cyanoalkyl" includes —$CH_2CN$, —$CH_2CH_2CN$, and $C_{1-4}$cyanoalkyl. "$C_{1-4}$cyanoalkyl" is intended to include $C_1$, $C_2$, $C_3$, and $C_4$ alkyl groups substituted with one or more cyano groups.

The term "cycloalkyl," as used herein, refers to a group derived from a non-aromatic monocyclic or polycyclic hydrocarbon molecule by removal of one hydrogen atom from a saturated ring carbon atom. Representative examples of cycloalkyl groups include, but are not limited to, cyclopropyl, cyclopentyl, and cyclohexyl. When numbers appear in a subscript after the symbol "C", the subscript defines with more specificity the number of carbon atoms that a particular cycloalkyl group may contain. For example, "$C_3$-$C_6$ cycloalkyl" denotes cycloalkyl groups with three to six carbon atoms.

The term "alkoxy," as used herein, refers to an alkyl group attached to the parent molecular moiety through an oxygen atom, for example, methoxy group (—$OCH_3$).

"Fluoroalkoxy" and "—O(fluoroalkyl)" represent a fluoroalkyl group as defined above attached through an oxygen linkage (—O—). For example, "$C_{1-4}$fluoroalkoxy" is intended to include $C_1$, $C_2$, $C_3$, and $C_4$ fluoroalkoxy groups.

The term "aryl," as used herein, refers to a group of atoms derived from a molecule containing aromatic ring(s) by removing one hydrogen that is bonded to the aromatic ring(s). Representative examples of aryl groups include, but are not limited to, phenyl, naphthyl, indanyl, indenyl, and 1,2,3,4-tetrahydronaphth-5-yl.

The term "benzyl," as used herein, refers to a methyl group in which one of the hydrogen atoms is replaced by a phenyl group.

The term "heteroatom" refers to oxygen (O), sulfur (S), and nitrogen (N).

The term "heterocyclo" or "heterocyclyl" may be used interchangeably and refer to non-aromatic 3- to 7-membered monocyclic groups and 6- to 11-membered bicyclic groups, in which at least one of the rings has at least one heteroatom (O, S or N), said heteroatom containing ring preferably having 1 to 3 heteroatoms independently selected from O, S, and/or N. Each ring of such a group containing a heteroatom can contain one or two oxygen or sulfur atoms and/or from one to four nitrogen atoms provided that the total number of heteroatoms in each ring is four or less, and further provided that the ring contains at least one carbon atom. The nitrogen and sulfur atoms may optionally be oxidized and the nitrogen atoms may optionally be quaternized. The fused rings completing the bicyclic group may contain only carbon atoms and may be saturated, partially saturated, or unsaturated. The heterocyclo group may be attached at any available nitrogen or carbon atom. The heterocyclo ring may be unsubstituted or may contain one or more substituents as valence allows.

Exemplary monocyclic heterocyclyl groups include oxetanyl, azetidinyl, pyrrolidinyl, imidazolinyl, oxazolidinyl, isoxazolinyl, thiazolidinyl, isothiazolidinyl, tetrahydrofuranyl, piperidinyl, piperazinyl, 2-oxopiperazinyl, 2-oxopiperidinyl, 2-oxopyrrolodinyl, 2-oxoazepinyl, azepinyl, 4-piperidonyl, tetrahydropyranyl, morpholinyl, thiamorpholinyl, thiamorpholinyl sulfoxide, thiamorpholinyl sulfone, 1,3-dioxolane and tetrahydro-1,1-dioxothienyl. Exemplary bicyclic heterocyclo groups include quinuclidinyl.

The term "heteroaryl" refers to substituted and unsubstituted aromatic 5- or 6-membered monocyclic groups and 9- or 10-membered bicyclic groups which have at least one heteroatom (O, S or N) in at least one of the rings, said heteroatom-containing ring preferably having 1, 2, or 3 heteroatoms independently selected from O, S, and/or N. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic group may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may be unsubstituted or may contain one or more substituents.

Exemplary monocyclic heteroaryl groups include pyrrolyl, pyrazolyl, pyrazolinyl, imidazolyl, oxazolyl, isoxazolyl, thiazolyl, thiadiazolyl, isothiazolyl, furanyl, thiophenyl, oxadiazolyl, pyridinyl, pyrazinyl, pyrimidinyl, pyridazinyl, and triazolyl.

Exemplary bicyclic heteroaryl groups include indolyl, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridyl, dihydroisoindolyl, and tetrahydroquinolinyl.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; and alkali or organic salts of acidic residues such as carboxylic acids. The pharmaceutically acceptable salts include the conventional non-toxic salts or the quaternary ammonium salts of the parent compound formed, for example, from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, nonaqueous media like ether, ethyl acetate, ethanol, isopropanol, or acetonitrile are preferred. Lists of suitable salts are found in *Remington's Pharmaceutical Sciences*, 17th ed., Mack Publishing Company, Easton, Pa., 1985, p. 1418, the disclosure of which is hereby incorporated by reference.

Salt(s) of the Formula (I) compounds can be formed by, for example, reacting a Formula (I) compound with, for example, an equivalent amount of acid or base in a medium that allows the newly formed salt to, for example, either be precipitated out, or be isolated via lyophilization. Exemplary acidic salt(s) that the compounds of Formula (I) can form with inorganic and/or organic acids include, but are not limited to, for example, include acetate, ascorbate, benzoate, benzenesulfonate, bisulfate, bitartrate, acid citrate, citrate, ethanesulfonate, formate, fumarate, gentisinate, gluconate, glucaronate, glutamate, hydrochloride, hydrobromide, hydroiodide, isonicotinate, maleate, mesylate, methanesulfonate, nitrate, pantothenate, phosphate, acid phosphate, saccharate, salicylate, succinate, sulfate, tartrate, p-toluenesulfonate, trifluoroacetate, lactate, and pamoate [i.e., 1,1'-methylene-bis-(2-hydroxy-3-naphthoate)] salts. Such salts can be formed in accordance with methods known to a person of ordinary skill in the art.

Exemplary basic salt(s) that the compounds of Formula (I) can form with inorganic and/or organic bases include, but are not limited to, for example, ammonium salts; alkali metal salts, such as, for example, sodium, lithium and potassium salts: alkaline earth metal salts, such as, for example, calcium and magnesium salts; salts formed with organic bases, such as, for example, benzathines, dicyclohexylamines, 2-amino-2-(hydroxymethyl)propane-1,3-diol (trisamine or tris), hydrabamines (such as, for example, N,N-bis(dehydroabietyl)ethylenediamine), N-methyl-D-glucamines, N-methyl-D-glycamides, and t-butyl amines; salts formed with amino acids, such as, for example, arginine and lysine; and salts formed by using agents, such as, for example, lower alkyl halides (e.g., methyl, ethyl, propyl, and butyl chlorides, bromides and iodides), dialkyl sulfates (e.g., dimethyl, diethyl, dibutyl, and diamyl sulfates), long chain halides (e.g., decyl, lauryl, myristyl and stearyl chlorides, bromides and iodides), and aralkyl halides (e.g., benzyl and phenethyl bromides) to quaternize basic nitrogen-containing groups. Such salts can be formed in accordance with methods known to a person of ordinary skill in the art.

In addition, compounds of Formula (I) are, subsequent to their preparation, preferably isolated and purified to obtain a composition containing an amount by weight equal to or greater than 99% of a compound of Formula (I) ("substantially pure"), which is then used or formulated as described herein. Such "substantially pure" compounds of Formula (I) are also contemplated herein as part of the present invention.

Any compound that can be converted in vivo to provide the bioactive agent (i.e., the compound of Formula (I)) is a prodrug within the scope and spirit of the invention.

The term "prodrugs" as employed herein includes amides and carbamates formed by reacting one or more amino groups of compounds of Formula (I) with alkyl, alkoxy, or aryl substituted acylating agents employing procedures known to those skilled in the art to generate amides, ureas, carbamates, and the like.

Various forms of prodrugs are well known in the art and are described in:

a) *The Practice of Medicinal Chemistry*, Camille G. Wermuth et al., Ch 31, (Academic Press, 1996);

b) *Design of Prodrugs*, edited by H. Bundgaard, (Elsevier, 1985);

c) *A Textbook of Drug Design and Development*, P. Krogsgaard-Larson and H. Bundgaard, eds. Ch 5, pgs 113-191 (Harwood Academic Publishers, 1991); and d) *Hydrolysis in Drug and Prodrug Metabolism*, Bernard Testa and Joachim M. Mayer, (Wiley-VCH, 2003).

In addition, compounds of the Formula (I) are, subsequent to their preparation, preferably isolated and purified to obtain a composition containing an amount by weight equal to or greater than 99% Formula (I) compound ("substantially pure" compound I), which is then used or formulated as described herein. Such "substantially pure" compounds of the Formula (I) are also contemplated herein as part of the present invention.

"Stable compound" and "stable structure" are meant to indicate a compound that is sufficiently robust to survive isolation to a useful degree of purity from a reaction mixture, and formulation into an efficacious therapeutic agent. The present invention is intended to embody stable compounds.

"Therapeutically effective amount" is intended to include an amount of a compound of the present invention alone or an amount of the combination of compounds claimed or an amount of a compound of the present invention in combination with other active ingredients effective to act as an antagonist of CYP17 enzyme, or effective to treat cancer.

As used herein, "treating" or "treatment" cover the treatment of a disease-state in a mammal, particularly in a human, and include: (a) preventing the disease-state from occurring in a mammal, in particular, when such mammal is predisposed to the disease-state but has not yet been diagnosed as having it; (b) inhibiting the disease-state, i.e., arresting it development; and/or (c) relieving the disease-state, i.e., causing regression of the disease state.

Compounds of the present invention may contain one or more additional asymmetric carbon atoms and therefore exist in two or more stereoisomeric forms. The present invention includes all of the possible individual stereoisomers, the individual tautomeric forms thereof, together with mixtures thereof. Separation of diastereoisomers may be achieved by conventional techniques, e.g., by fractional crystallization, chromatography or HPLC of a stereoisomeric mixture of a compound of the present invention, or a suitable salt or derivative thereof. An individual enantiomer of the compound may also be prepared from a corresponding optically pure intermediate or by resolution, such as by HPLC of the corresponding racemate using a suitable chiral support or by fractional crystallization of the diastereoisomeric salts formed by reaction of the corresponding racemate with a suitable optically active acid or base, as appropriate. All stereoisomers of the compounds of the instant invention are contemplated, either in admixture or in pure or substantially pure form.

The compounds of the present invention are intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed.

Also embraced within this invention is a class of pharmaceutical compositions comprising the compound of Formula (I) or a pharmaceutically acceptable salt thereof in association with one or more non-toxic, pharmaceutically-acceptable carriers and/or diluents and/or adjuvants (collectively referred to herein as "carrier" materials) and, if desired, other active ingredients. The compounds of Formula (I) may be administered by any suitable route, preferably in the form of a pharmaceutical composition adapted to such a route, and in a dose effective for the treatment intended. The compounds and compositions of the present invention may, for example, be administered orally, mucosally, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles. For example, the pharmaceutical carrier may contain a mixture of mannitol or lactose and microcrystalline cellulose. The mixture may contain additional components such as a lubricating agent, e.g., magnesium stearate and a disintegrating agent such as crospovidone. The carrier mixture may be filled into a gelatin capsule or compressed as a tablet.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a tablet, capsule, suspension, or liquid. The pharmaceutical composition is preferably made in the form of a dosage unit containing a particular amount of the active ingredient. Examples of such dosage units are tablets or capsules. For example, these may contain an amount of active ingredient from about 0.5 to 2000 mg, preferably from about 0.5 to 500 mg, more preferably from about 0.5 to 150 mg. A suitable daily dose for a human or other mammal may vary widely depending on the condition of the patient and other factors, but, once again, can be determined using routine methods.

The amounts of compounds that are administered and the dosage regimen for treating a disease condition with the compounds and/or compositions of this invention depends on a variety of factors, including the age, weight, sex, the medical condition of the subject, the type of disease, the severity of the disease, the route and frequency of administration, and the particular compound employed. Thus, the dosage regimen may vary widely, but can be determined routinely using standard methods. A daily dose of about 0.01 to 100 mg/kg body weight, preferably between about 0.05 and about 50 mg/kg body weight and most preferably between about 0.05 to 20 mg/kg body weight, may be appropriate. The daily dose can be administered in one to four doses per day.

For therapeutic purposes, the active compounds of this invention are ordinarily combined with one or more adjuvants appropriate to the indicated route of administration. If administered orally, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinyl alcohol, and/or polyvinylpyrrolidone, and then tableted or encapsulated for convenient administration. Such capsules or tablets may contain a controlled-release formulation as may be provided in a dispersion of active compound in hydroxypropylmethyl cellulose.

The oily phase of the emulsions comprising compounds of Formula (I) may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the so-called emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required. Alternatively, high melting point lipids such as white soft paraffin and/or liquid paraffin or other mineral oils can be used.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers. Other adjuvants and modes of administration are well and widely known in the pharmaceutical art. The active ingredient may also be administered by injection as a composition with suitable carriers including saline, dextrose, or water, or with cyclodextrin (i.e., Captisol), cosolvent solubilization (i.e., propylene glycol) or micellar solubilization (i.e., Tween 80).

The sterile injectable preparation may also be a sterile injectable solution or suspension in a non-toxic parenterally acceptable diluent or solvent, for example as a solution in propylene glycol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

The pharmaceutical compositions may be subjected to conventional pharmaceutical operations such as sterilization and/or may contain conventional adjuvants, such as preservatives, stabilizers, wetting agents, emulsifiers, and buffers. Tablets and pills can additionally be prepared with enteric coatings. Such compositions may also comprise adjuvants, such as wetting, sweetening, flavoring, and perfuming agents.

Pharmaceutical compositions of this invention comprise the compound of Formula (I), or a pharmaceutically acceptable salt thereof, and optionally an additional agent selected from any pharmaceutically acceptable carrier, adjuvant, and vehicle. Alternate compositions of this invention comprise a compound of the Formula (I) described herein, or a pharmaceutically acceptable salt thereof, and a pharmaceutically acceptable carrier, adjuvant, or vehicle.

Pharmaceutically acceptable carriers, adjuvants, and vehicles that may be used in the pharmaceutical compositions of this invention include, but are not limited to, ion exchangers, alumina, aluminum stearate, lecithin, self-emulsifying drug delivery systems (SEDDS) such as d-alpha-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as alpha-, beta-, and gamma-cyclodextrin, or chemically modified derivatives such as hydroxyalkylcyclodextrins, including 2- and 3-hydroxypropyl-cyclodextrins, or other solubilized derivatives may also be advantageously used to enhance delivery of compounds of the formulae described herein.

Utility

The compounds of Formula (I) are useful for the treatment of cancer, for example, cancers dependent upon androgen receptor signaling. These compounds inhibit the activity of the CYP17 enzyme, which is involved in biosynthesis of androgens and estrogens. Blocking this enzyme would inhibit the production of gonadal, adrenal, and tumoral androgens and offers a new treatment option for cancers dependent upon androgen receptor and estrogen receptor signaling, such as prostate cancer and estrogen receptor-positive breast cancer patients. Thus, the treatment comprises administering to the patient a compound of Formula (I) or a pharmaceutically acceptable salt or prodrug thereof.

In one embodiment, a method is provided for treating cancer comprising administering compound of Formula (I) or a pharmaceutically acceptable salt or prodrug thereof to a mammal in need thereof. The method of this embodiment can be used to treat a variety of cancers, including, but not limited to, breast cancer, ovarian cancer, and prostate cancer. Preferably, the method of this embodiment is used to treat prostate cancer or breast cancer. In one method of this embodiment, compound of Formula (I) is administered in a therapeutically effective amount.

In one embodiment, provided are methods for treating cancer in a patient wherein the cancer is dependent upon CYP17 activation, comprising administering to the patient in need thereof a compound of Formula (I) or a pharmaceutically acceptable salt or prodrug thereof. In one method of this embodiment, a compound of Formula (I) is administered to treat prostate cancer. In another method of this embodiment, a compound of Formula (I) is administered to treat breast cancer. Preferably, a therapeutically effective amount of Compound (I) is administered.

The amount of a compound of Formula (I) which is administered and the dosage regimen for treating a particular cancer depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A daily dose of about 0.01 to 500 mg/kg body weight, preferably between about 0.05 and about 50 mg/kg body weight and most preferably between about 0.05 to 20 mg/kg body weight, may be appropriate may be appropriate. The daily dose can be administered in one to four doses per day.

In treating cancer, a combination of chemotherapeutic agents and/or other treatments (e.g., radiation therapy) is often advantageous. The second (or third) agent may have the same or different mechanism of action than the primary therapeutic agent. It may be especially useful to employ cytotoxic drug combinations wherein the two or more drugs being administered act in different manners or in different phased of the cell cycle, and/or where the two or more drugs have overlapping toxicities or side effects, and/or where the drugs being combined each has a demonstrated efficacy in treating the particular disease state manifested by the patient.

Accordingly, a compound of Formula (I) may be administered in combination with other anti-cancer treatments useful in the treatment of cancer or other proliferative diseases. The invention herein further comprises use of a compound of Formula (I) in preparing medicaments for the treatment of cancer, and/or it comprises the packaging of a compound of Formula (I) herein together with instructions that the compound be used in combination with other anti-cancer or cytotoxic agents and treatments for the treatment of cancer. The present invention further comprises combinations of a compound of Formula (I) and one or more additional agents in kit form, e.g., where they are packaged together or placed in separate packages to be sold together as a kit, or where they are packaged to be formulated together.

The compound of Formula (I) can be formulated or co-administered with other therapeutic agents that are selected for their particular usefulness in addressing side effects associated with the aforementioned conditions. For example, the compound of Formula (I) may be formulated with agents to prevent nausea, hypersensitivity and gastric irritation, such as antiemetics, and $H_1$ and $H_2$ antihistaminics.

The phrase "anti-cancer treatment" includes but is not limited to, for example, radiation therapy and surgery.

The other anti-cancer agents may be selected from any one or more of the following: alkylating agents (including nitrogen mustards, alkyl sulfonates, nitrosoureas, ethylenimine derivatives, and triazenes); anti-angiogenics (including matrix metalloproteinase inhibitors); antimetabolites (including adenosine deaminase inhibitors, folic acid antagonists, purine analogues, and pyrimidine analogues); antibiotics or antibodies (including monoclonal antibodies, CTLA-4 antibodies, anthracyclines); aromatase inhibitors; cell-cycle response modifiers; enzymes; farnesyl-protein transferase inhibitors; hormonal and antihormonal agents and steroids (including synthetic analogs, glucocorticoids, estrogens/anti-estrogens [e.g., SERMs], androgens/anti-androgens, progestins, progesterone receptor agonists, and luteinizing hormone-releasing [LHRH] agonists and antagonists); insulin-like growth factor (IGF)/insulin-like growth factor receptor (IGFR) system modulators (including IGFR1 inhibitors); integrin-signaling inhibitors; kinase inhibitors (including multi-kinase inhibitors and/or inhibitors of Src kinase or Src/abl, cyclin dependent kinase [CDK] inhibitors, panHer, Her-1 and Her-2 antibodies, VEGF inhibitors, including anti-VEGF antibodies, EGFR inhibitors, mitogen-activated protein [MAP] inhibitors, MEK inhibitors, Aurora kinase inhibitors, PDGF inhibitors, and other tyrosine kinase inhibitors or serine/threonine kinase inhibitors; microtubule-disruptor agents, such as ecteinascidins or their analogs and derivatives; microtubule-stabilizing agents such as taxanes, and the naturally-occurring epothilones and their synthetic and semi-synthetic analogs; microtubule-binding, destabilizing agents (including vinca alkaloids); topoisomerase inhibitors; prenyl-protein transferase inhibitors; platinum coordination complexes; signal transduction inhibitors; and other agents used as anti-cancer and cytotoxic agents such as biological response modifiers, growth factors, and immune modulators.

The above other therapeutic agents, when employed in combination with a compound of Formula (I), can be used, for example, in those amounts indicated in the Physicians' Desk Reference (PDR) or as otherwise determined by one of ordinary skill in the art.

In one embodiment, a method is provided for treating cancer comprising administering to a mammal in need thereof a compound of Formula (I) or a pharmaceutically acceptable salt or prodrug thereof; administering a glucocorticoid; and optionally, one or more additional anticancer agent. Examples of suitable glucocorticoids include, but are not limited to, dexamethasone and prednisolone.

In one embodiment, a method is provided for treating cancer comprising administering to a mammal in need thereof a compound of Formula (I) or a pharmaceutically acceptable salt or prodrug thereof; administering a mineralocorticoid receptor antagonist; and optionally, one or more additional anticancer agent. Examples of suitable mineralocorticoid receptor antagonists include, but are not limited to, eplerenone.

In another embodiment, a compound of Formula (I) or a pharmaceutically acceptable salt thereof is used to treat prostate cancer.

In one embodiment, the patient is an animal.

In another embodiment, the patient is a mammalian species including, but not limited to, for example, humans and domestic animals, such as, for example, dogs, cats, and horses.

In one embodiment, the present invention provides a compound of Formula (I) or a pharmaceutically acceptable salt thereof for use in therapy.

In one embodiment, the use of a compound of Formula (I) or a pharmaceutically acceptable salt thereof in the manufacture of a medicament for the treatment of cancer, including prostate cancer, is provided.

In one embodiment, the use of a compound of Formula (I) or a pharmaceutically acceptable salt thereof in the manufacture of a medicament for the treatment of cancer, including breast cancer, is provided.

Methods of Preparation

The compounds of the present invention may be prepared by synthetic routes that include processes analogous to those well-known in the chemical arts, particularly in light of the description provided herein. For illustrative purposes, general Schemes 1-11 below show general methods for preparing the compounds of the present invention, as well as key intermediates. For a more detailed description of the individual reaction steps, see the Example section below. Those skilled in the art will appreciate that other synthetic routes may be used to synthesize the inventive compounds. Although specific starting materials and reagents are depicted in the Schemes and discussed below, other starting materials and reagents can easily be substituted to provide a variety of compounds of the present invention. In addition, many of the compounds prepared by the methods below can be further modified in light of this disclosure using conventional chemistry well known to those skilled in the art.

As shown in Scheme 1, for instance, the commercially available halogenated pyridine II can be condensed with various hydrazines of general formula III resulting in the formation of the intermediate hydrazone of general formula IV. Cyclization of the hydrazone can be promoted by heating to afford the 4-iodo-indazole of general structure V. Treatment of the iodide V with a Pd(II) species such as PdCl$_2$(dppf) in the presence of a diboronic ester, such as bis-(pinacolato) diboron, and an inorganic base such as potassium acetate, will afford the boronic ester of general structure VI. The boronic ester VI can be coupled to heteroaromatic halides of general structure VII under standard Suzuki coupling conditions to afford compounds of general structure (I).

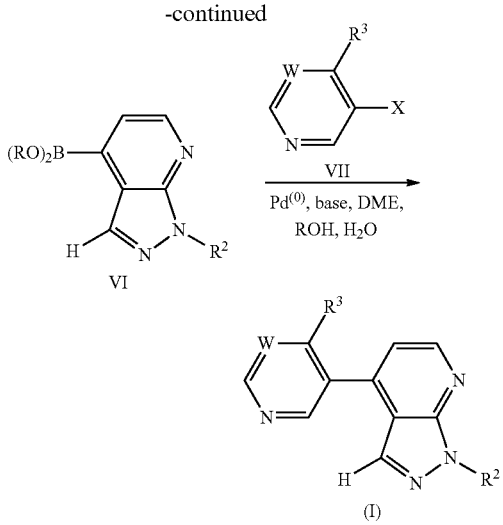

Alternatively, the aldehyde II can be treated with an alkyl or aryl lithium or Grignard reagent to afford the resulting benzylic alcohol which can subsequently be oxidized, by Dess-Martin periodinane for example, to afford the ketone of general structure VIII (Scheme 2). Treatment of the ketone with alkyl or aryl hydrazines III, will afford the intermediate hydrazone IX, which can cyclize to the indazole of general structure X. The indazole X coupled to a heteroaryl halide VII under standard Suzuki conditions as depicted in Scheme 1 to make compounds of general structure (I).

SCHEME 1

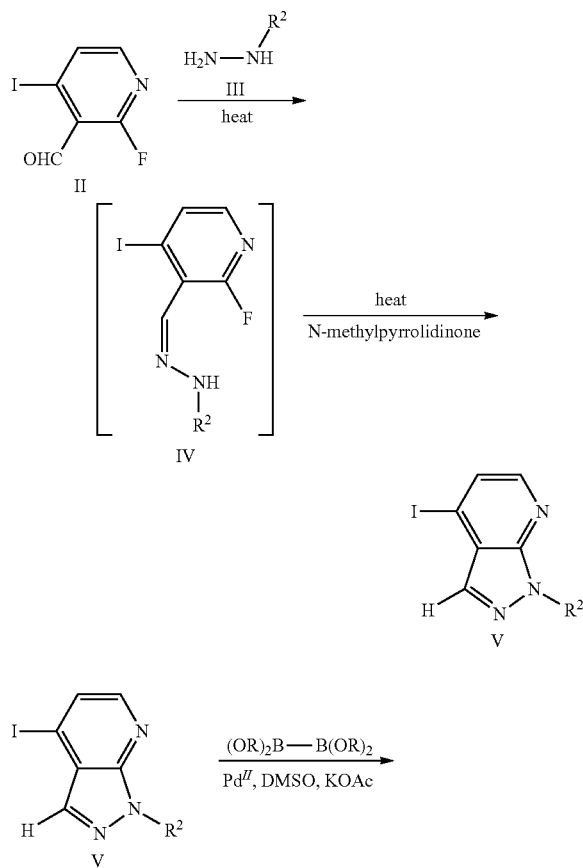

SCHEME 2

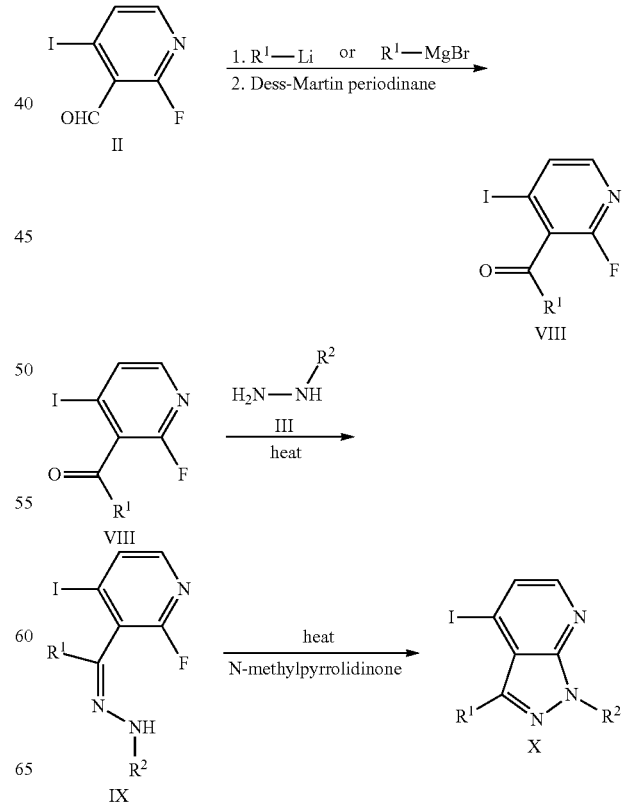

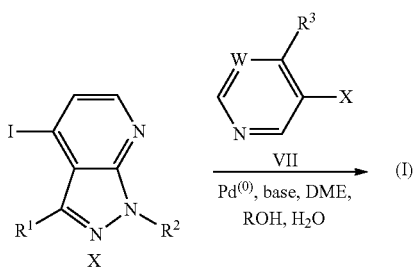

Additionally, halogenated heteroaromatics of general structure VII, can be treated with a Pd(II) species, such as PdCl$_2$(dppf) in the presence of a diboronic ester, such as bis-(pinacolato)diboron, and an inorganic base such as potassium acetate to afford the boronic ester of general structure XI (Scheme 3). The boronic ester can then be coupled to the aryl halide or triflate of general structure XII under standard Suzuki coupling conditions to afford compounds of general structure (I).

SCHEME 3

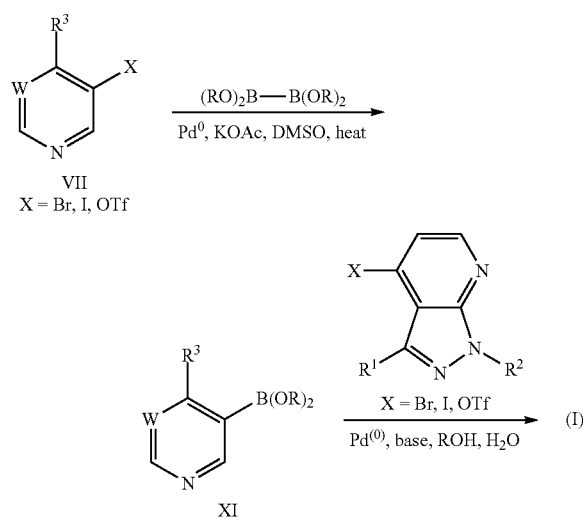

Scheme 4 depicts another method where N-1 of the indazole can be alkylated by treatment of a compound of general structure XIII with an inorganic base, such as cesium carbonate, and a primary or secondary alkyl halide to generate compounds of general structure (I).

SCHEME 4

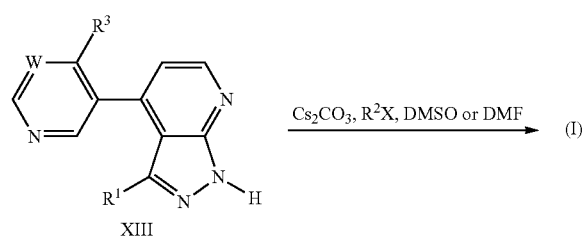

Alternatively, compounds of general structure XIII, which can be prepared from the compound of general structure II and hydrazine, can be treated with an aryl or heteroaryl bromide, iodide or chloride in the presence of Cu(I), an amine base such as 1,2-cyclohexyldiamine and an inorganic base such as potassium phosphate to afford analogs of general structure (I) as depicted in Scheme 5.

SCHEME 5

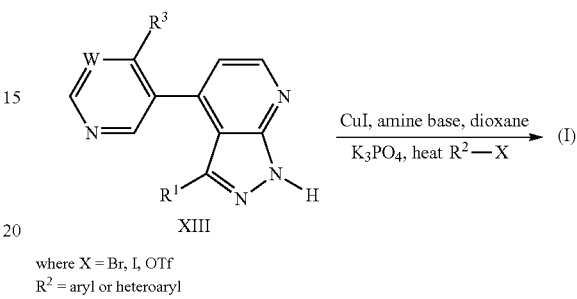

where X = Br, I, OTf
R$^2$ = aryl or heteroaryl

Compounds of structure V can be halogenated at C-3 of the indazole by treatment with, for example NCS as shown in Scheme 6, to give the compound of general structure XIV. This can then be converted to compounds of general structure (I) as described previously.

SCHEME 6

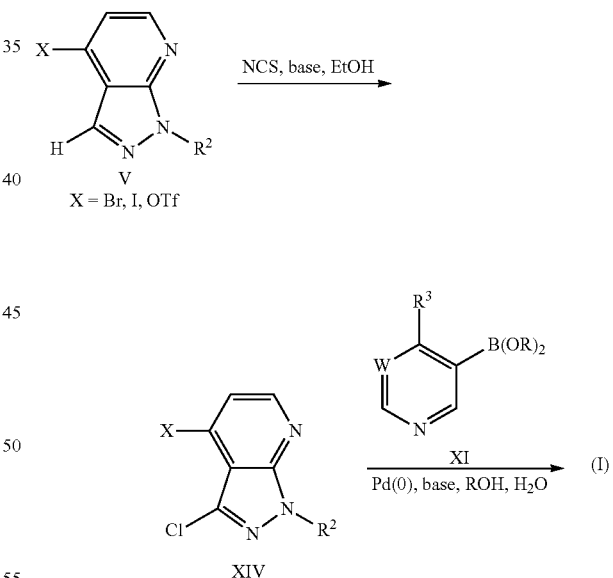

Preparation of 4-substituted pyrimidines can be done by many methods well known to those skilled in the art. Scheme 7 depicts one method for preparation of 4-amino and 4-alkoxy pyrimidines from commercially available 4-chloro-5-iodopyrimidine. Treatment of 4-chloro-5-iodopyrimidine with the desired alcohol or amine in the presence of a base such as NaH will afford the respective products of general structure XVI and XVII. These pyrimidines can then be converted to compounds of general structure (I) by standard Suzuki conditions as described previously.

SCHEME 7

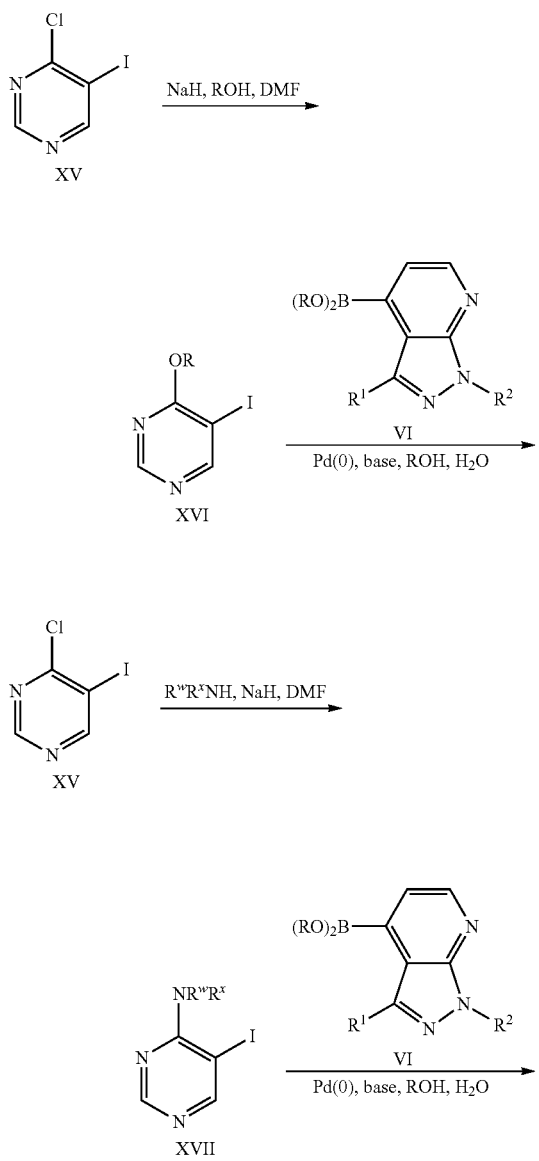

4-alkyl and 4-aryl substituted pyrimidines can be prepared by many methods well known to those skilled in the art. Scheme 8 depicts one such method where 5-bromopyrimidine can be treated with an alkyl or aryl lithium or a Grignard reagent to give the 4-substituted dihydropyrimidine. Subsequent oxidation by, for example, DDQ then gives the desired 4-substituted pyrimidine XIX. Subsequent Suzuki coupling as described previously then will give a compound of general structure (I).

SCHEME 8

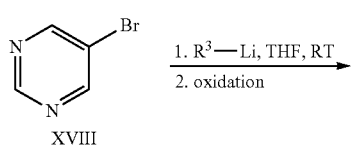

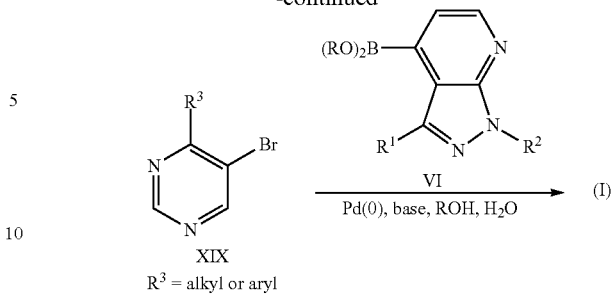

4-alkyl-3-halopyridines can be purchased or prepared by several methods well known to those skilled in the art. Scheme 9 depicts one possible method for preparing 4-alkyl-3-bromopyridines starting with the commercially available 3-bromopyridine XXII. Treatment with a strong base, such as LDA, to generate an anion at the 4-position, followed by addition of an aldehyde or ketone will give a carbinol of general structure XXI. The carbinol can then be converted to compounds of general structure (I) via standard Suzuki coupling conditions as described previously. Alternatively, the carbinol XXIII can be further modified, for example by de-oxygenation, by methods well known to those skilled in the art to give optionally substituted compounds of general structure (I).

SCHEME 9

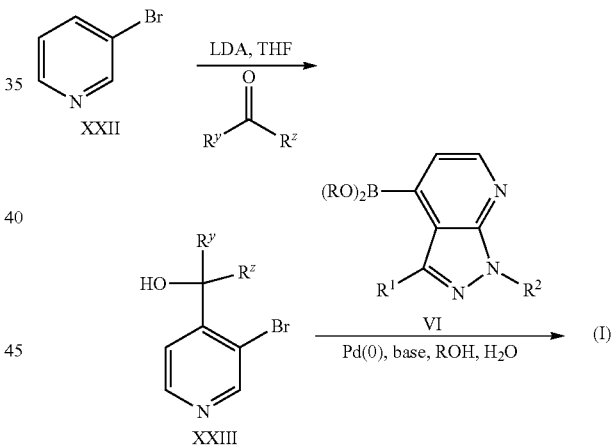

In addition C-linked heteroaromatics groups at C-4 of the indazole core, N-linked analogs can also be made by the method depicted in Scheme 11. Substituted imidazoles, for example, can be coupled with aryl halides of general structure XII by treatment with Cu(I) in the presence of an inorganic base and proline to afford compounds of general structure (I).

EXAMPLES

The present invention is further defined in the following examples. It should be understood that these examples are given by way of illustration only. From the above discussion and this example, one skilled in the art can ascertain the essential characteristics of this invention, and without departing from the spirit and scope thereof, can make various changes and modifications to the invention to adapt the invention to various uses and conditions. As a result, the present invention is not limited by the illustrative examples set forth herein below, but rather defined by the claims appended hereto.

All temperatures are in degrees Celsius (° C.) unless indicated otherwise herein.

All reactions were carried out with continuous magnetic stirring under an atmosphere of dry nitrogen. All evaporations and concentrations were carried out on a rotary evaporator under reduced pressure. Commercial reagents were used as received without additional purification. Solvents were commercial anhydrous grades and were used without further drying or purification. Flash chromatography was performed using silica gel (EMerck Kieselgel 60, 0.040-0.060 mm)

ABBREVIATIONS

AcOH acetic acid
$Ac_2O$ acetic anhydride
aq. aqueous
$CH_2Cl_2$ dichloromethane
DDQ 2,3-dichloro-5,6-dicyano-p-benzoquinone
DIEA diisopropylethylamine
DMAP dimethylaminopyridine
DME dimethyl ether
DMF dimethylformamide
DMSO dimethylsulfoxide
Et ethyl
$Et_3N$ triethylamine
$Et_2O$ diethyl ether
EtOAc ethyl acetate
EtOH ethanol
$Et_3SiH$ triethylsilane
g gram(s)
h hour
HCl hydrochloric acid
HPLC high performance liquid chromatography
iPr isopropyl
iPrOH isopropanol
KOAc potassium acetate
L liter
LC/MS liquid chromatography/mass spectrometry
LDA lithium diisopropylamine
Me methyl
MeOH methanol
mg milligram(s)
min minute
mL milliliter
mmol millimole(s)
mp melting point
mol moles
MS mass spectrometry
NaOMe sodium methoxide
NBS N-bromosuccinimide
n-BuLi n-butyl lithium
$NH_4OAc$ ammonium acetate
NMP N-methylpyrrolidinone
NMR nuclear magnetic resonance
OTf trifluoromethane sulfonate
$PdCl_2(dppf).CH_2Cl_2$ dichloro[1,1'-bis(diphenylphosphino)ferrocene]palladium(II) dichloromethane adduct
Prep HPLC preparative reverse phase HPLC
$PMe_3$ trimethyl phosphine
ret. T HPLC retention time (minutes)
RT or rt room temperature
sat or sat'd saturated
TBSCl tert-butyldimethylsilylchloride
TFA trifluoroacetic acid
$Tf_2O$ trifluoromethylsulfonic anhydride
THF tetrahydrofuran
TLC thin layer chromatography
VCD vibrational circular dichroism
μL microliter All final products were characterized by $^1$H NMR, HPLC, electrospray ionization (ESI MS) or atmospheric pressure ionization (API MS) mass spectrometry. $^1$H NMR spectra were obtained on either a 500 MHz JEOL or a 400 MHz Bruker instrument. $^{13}$C NMR spectra were recorded at 100 or 125 MHz. Field strengths are expressed in units of (parts per million, ppm) relative to the solvent peaks, and peak multiplicities are designated as follows: s, singlet; d, doublet; dd, doublet of doublets; dm, doublet of multiplets; t, triplet; q, quartet; br s, broad singlet; m, multiplet.

LC/MS Conditions:

Condition A: Waters X-Bridge 4.6×50 mm S10 column, 0% B-100% B with flow rate 4 mL/min and 3 min gradient time; Solvent A: 10% MeOH/90% water/0.1% TFA; Solvent B: 10% water/90% MeOH/0.1% TFA, wavelength 254 nM.

Condition B: Phenomenex-Luna 2.0×50 mm 3 μm column, 4 min gradient time, flow rate: 0.8 mL/min; Solvent A: 10% MeOH/90% water/0.1% TFA; Solvent B: 90% MeOH/10% water/0.1% TFA, wavelength 254 nM.

Condition C: Waters Acquity UPLC BEH C18, 2.1×50 mm, 1.7-μm particles; Mobile Phase A: 5:95 acetonitrile:water with 10 mM ammonium acetate; Mobile Phase B: 90:10 acetonitrile:water with 10 mM ammonium acetate; Temperature: 50° C.; Gradient: 0-100% B over 3 minutes, then a 0.75-minute hold at 100% B; Flow: 1.11 mL/min.

Condition D: LC-MS conditions: Column: Supelco Ascentis Express C18, 4.6×50 mm, 2.7-μm particles; Mobile Phase A: 5:95 acetonitrile:water with 10 mM ammonium acetate; Mobile Phase B: 90:10 acetonitrile:water with 10 mM ammonium acetate; Temperature: 35° C.; Gradient: 0-100% B over 4 minutes, then a 1-minute hold at 100% B; Flow: 4 mL/min.

Condition E: Phen-Luna C18 2.5 um 2.0×30 mm, 0% B-100% B with flow rate 4 mL/min and 3 min gradient time; Solvent A: 10% MeOH/90% water/0.1% TFA; Solvent B: 10% water/90% MeOH/0.1% TFA, wavelength 254 nM.

Condition F: Waters Acquity UPLC BEH C18, 2.1×50 mm, 1.7-μm particles; Mobile Phase A: 5:95 acetonitrile:water with 0.05% TFA; Mobile Phase B: 90:10 acetonitrile:water with 0.05% TFA; Temperature: 50° C.; Gradient: 0-100% B over 3 minutes, then a 0.75-minute hold at 100% B; Flow: 1.11 mL/min Preparative HPLC Conditions:

Condition A: Shimadzu preparative HPLC system using a gradient of Solvent A (10% MeOH/90% water/0.1% TFA) and Solvent B (90% MeOH/10% water/0.1% TFA), monitoring at a wavelength of 254 nM, with flow rate=36 mL/min (unless otherwise noted).

Analytical HPLC Conditions:

Condition A: Waters X-Bridge C18, 3.0×150 mm 3.5 μM (high pH), 10% B-100% B with flow rate 1 mL/min and gradient time 30 min. Solvent A: 95% water/5% MeOH/10 mM ammonium bicarbonate; Solvent B: 95% water/10 mM ammonium bicarbonate, wavelength 220/254 nM.

Condition B: Waters X-Bridge phenyl, 3.0×150 mm 3.5 μM (high pH), 10% B-100% B with flow rate 1 mL/min and gradient time 30 min. Solvent A: 95% water/5% MeOH/10 mM ammonium bicarbonate; Solvent B: 95% MeOH/5% water/10 mM ammonium bicarbonate, wavelength 220/254 nM.

Condition C: Waters Sunfire C18, 3.0×150 mm 3.5 μM (low pH), 10% B-100% B with flow rate 1 mL/min and gradient time 30 min. Solvent A: 5% ACN/95% water/0.1% TFA; Solvent B: 95% ACN/5% water/0.1% TFA, wavelength 220/254 nM.

Condition D: Waters X-Bridge phenyl, 3.0×150 mm 3.5 μM (low pH), 10% B-100% B with flow rate 1 mL/min and gradient time 30 min. Solvent A: 5% ACN/95% water/0.1% TFA; Solvent B: 95% ACN/5% water/0.1% TFA, wavelength 220/254 nM.

Example 1

3-(4-(4-methoxypyridin-3-yl)-1H-pyrazolo[3,4-b]pyridin-1-yl)benzenesulfonamide

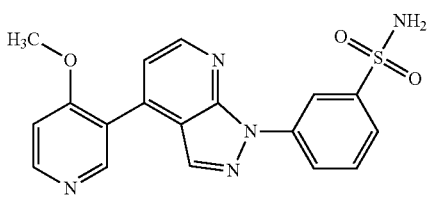

Intermediate 1A: 3-(4-iodo-1H-pyrazolo[3,4-b]pyridin-1-yl)benzenesulfonamide

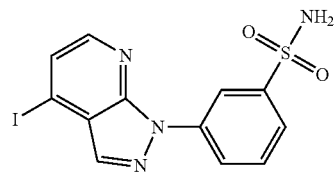

To a 45 mL pressure bottle was added 2-fluoro-4-iodonicotinaldehyde (1.05 g, 4.18 mmol), 3-hydrazinylbenzenesulfonamide (800 mg, 4.27 mmol), and anhydrous NMP (15 mL). The reaction mixture was flushed with argon, securely capped, and heated at 185° C. for 6.5 h. The reaction mixture was cooled to room temperature and slowly added to a rapidly stirred solution of diethyl ether (430 mL). The resulting solid material was filtered and the pale yellow Et$_2$O filtrate was allowed to stand for 18 h at room temperature. The yellow crystals precipitated out and were collected by vacuum filtration to give 425 mg (16.42%) of the title compound as a yellow solid as a "dot" 2 NMP complex by proton NMR. LC/MS (Condition B): ret. T=3.2 min, (M+H)$^+$ 400.83. $^1$H NMR (500 MHz, DMSO-d$_6$) δ ppm 7.56 (s, 2 H) 7.78-7.84 (m, 2 H) 7.89-7.92 (m, 1 H) 8.37-8.42 (m, 2 H) 8.57 (dt, J=4.81, 2.33 Hz, 1 H) 8.75 (s, 1 H). Second and third crops of yellow solid (300 mg, 11.7%; 246 mg, 9.4%) were identical to the first crop of material.

Intermediate 1B: 1-(3-sulfamoylphenyl)-1H-pyrazolo[3,4-b]pyridin-4-ylboronic acid

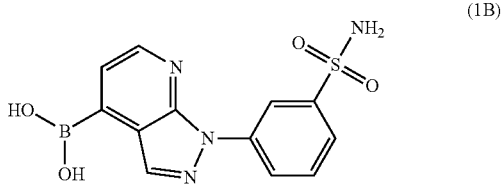 [SMILES: NS(=O)(=O)c1cccc(-n2ncc3c(B(O)O)ccnc32)c1]

To a 48 mL pressure bottle was added 3-(4-iodo-1H-pyrazolo[3,4-b]pyridin-1-yl)benzenesulfonamide, "dot" 2 1-methyl-2-pyrrolidinone complex (60 mg, 0.100 mmol), 4,4,4',4',5,5,5',5'-octamethyl-2,2'-bi(1,3,2-dioxaborolane) (94.7 mg, 0.373 mmol), potassium acetate (24.4 mg, 0.249 mmol) and anhydrous DMSO (Volume: 2 mL). The reaction mixture was purged well with argon and treated with PdCl$_2$(dppf).CH$_2$Cl$_2$ (12.5 mg, 0.017 mmol). The reaction mixture was then heated to 84° C. for 1 h to give the desired intermediate. LC/MS (Condition B): ret. T=2.4 min, (M+H)$^+$ 318.98.

Example 1

To the reaction mixture containing Intermediate 1B (31.8 mg, 0.1 mmol) was added 3-iodo-4-methoxypyridine (125.5 mg, 0.534 mmol), sodium carbonate (68.1 mg, 0.643 mmol) and EtOH:DME:H$_2$O (1.2:2.5:1.0 ratio) (1.5 mL). The reaction mixture was purged with argon, then treated with tetrakis(triphenylphosphine)palladium (0) (23 mg, 0.020 mmol). The reaction mixture was purged with argon again, securely capped, and placed in a 105° C. oil bath for 2 h 45 min. The reaction mixture was cooled to room temperature, then diluted with DMF (4 mL). The resulting solution was filtered through a 0.45 uM frit attached to a single-use Waters C-18 sep-pak light cartridge (part # WAT023501), and then purified by preparative HPLC (Condition A) using a Phenomenex Luna Axia 30×100 mm S10 column from 20% Solvent B to 85% Solvent B over 12 min, ret. T=4.84 min to afford the title compound (12 mg, 31%) as a white solid. $^1$H NMR (500 MHz, DMSO-d$_6$) δ ppm 3.91-3.97 (m, 3 H), 4.04 (d, J=7.93 Hz, 2 H), 7.35 (d, J=3.36 Hz, 1 H), 7.49-7.58 (m, 1 H), 7.79-7.86 (m, 2 H), 8.40-8.47 (m, 1 H), 8.59-8.68 (m, 3 H), 8.78-8.85 (m, 2 H). LC/MS (Condition B): ret. T=2.0 min, (M+H)$^+$ 382.04. Analytical HPLC: (Condition A): >97%, ret. T=16.13 min, (Condition B): >97%, ret. T=18.28 min, (Condition C): >98%, ret. T=5.96 min, (Condition D): >98%, ret. T=6.61 min.

Example 2

1-(4-fluorophenyl)-4-(4-methylpyrimidin-5-yl)-1H-pyrazolo[3,4-b]pyridine

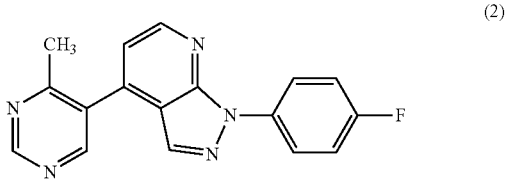 [SMILES: Cc1ncncc1-c1ccnc2c1cnn2-c1ccc(F)cc1]

Intermediate 2A: 1-(4-fluorophenyl)-4-iodo-1H-pyrazolo[3,4-b]pyridine

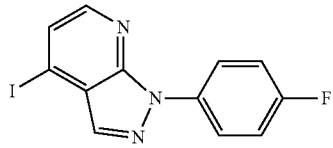

(2A)

To a dry 16×100 mm Chem-Glass reaction tube under N₂ was added 2-fluoro-4-iodonicotinaldehyde (600 mg, 2.390 mmol), (4-fluorophenyl)hydrazine (332 mg, 2.63 mmol) and anhydrous NMP (3.2 mL). The reaction mixture was flushed with argon, securely capped, stirred for 20 min at room temperature, and then placed in a 185° C. oil bath for 2 h. The reaction mixture was then allowed to stir at room temperature for 16 h. The reaction mixture was diluted with EtOAc (200 mL) and the organic layer was extracted with water (5×50 mL), brine (1×50 mL), dried over Na₂SO₄, filtered and evaporated to dryness. The residue was purified by Biotage Silica gel chromatography on a 90 g Thompson Single Step™ silica cartridge using a linear gradient from 100% hexanes to 100% dichloromethane over 12 column volumes to give 480 mg (59.2%) of the title compound, Intermediate 2A, as an off white solid. ¹H NMR (500 MHz, methanol-d₄) δ ppm 8.22-8.28 (3 H, m), 8.15 (1 H, s), 7.78 (1 H, d, J=4.88 Hz), 7.25-7.37 (2 H, m). LC/MS (Condition A): 100% purity; ret. T=2.9 min, (M+H)⁺ 339.97.

Intermediate 2B

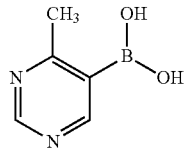

(2B)

To a pressure bottle were added 5-bromo-4-methylpyrimidine (0.8 g, 4.62 mmol), 4,4,4',4',5,5,5',5'-octamethyl-2,2'-bi(1,3,2-dioxaborolane) (1.409 g, 5.55 mmol), PdCl₂(dppf)-CH₂Cl₂Adduct (0.189 g, 0.231 mmol), potassium acetate (1.135 g, 11.56 mmol), and DMSO (8 mL). The reaction mixture was flushed with nitrogen and heated to 90° C. overnight. The reaction mixture was cooled to room temperature, quenched with water, and extracted with EtOAc. The combined organic layers were washed with water and brine, dried over Na₂SO₄, filtered, and concentrated to afford the title compound.

Example 2

A flask containing a mixture of tetrakis(triphenylphosphine)palladium(0) (15 mg, 0.013 mmol), Intermediate 2A (32.3 mg, 0.095 mmol), and sodium carbonate (60 mg, 0.566 mmol) was flushed with argon. To a vial containing Intermediate 2B (40 mg, 0.290 mmol) was added EtOH:DME:H₂O (1.2:2.5:1.0 ratio) (1.2 mL) and the resulting dark solution was flushed with Ar. This solution was transferred via glass pipette to the flask containing the Pd, base and Intermediate 2A. The reaction mixture was flushed with argon for 2-3 min, securely capped and placed in a 105° C. oil bath for 3 h. The reaction mixture was evaporated to dryness, the residue was dissolved in a mixture of DMSO/MeOH (8 mL), filtered through a 45μ frit, and purified by preparative HPLC (Condition A) using a Phenomenex Luna Axia 30×100 mm S10 column from 25% B to 100% B over 12 min, ret. T=10.61 min. The product fractions were applied to a Waters Oasys MCX 20 cc (1 g) LP extraction cartridge, eluted with additional MeOH (30 mL) and Aldrich 2.0M NH₃/MeOH (20 mL), followed by evaporation to dryness. The resulting residue was dissolved in a mixture of CH₂Cl₂ and EtOAc and applied to the head of a 12 g Thomson SINGLE StEP Silica cartridge. Elution with a liner gradient from 100% CH₂Cl₂ to 100% EtOAc over 12 column volumes, followed by evaporation of product-containing fractions afforded the title compound as a tan solid (5.7 mg, 19%). ¹H NMR (500 MHz, METHANOL-d₄) δ ppm 9.19 (1 H, s), 8.81 (1 H, s), 8.77 (1 H, d, J=4.58 Hz), 8.27-8.34 (2 H, m), 8.17-8.22 (1 H, m), 7.28-7.42 (3 H, m), 2.55 (3 H, s). LC/MS (Condition B): ret. T=3.45 min, (M+H)⁺ 306.06. Analytical HPLC: (Condition A): >94%, ret. T=20.62 min, (Condition B): >96%, ret. T=20.40 min, (Condition C): >98%, ret. T=16.43 min, (Condition D): >99%, ret. T=13.35 min.

Example 3

1-(4-fluorophenyl)-4-(4-methylpyridin-3-yl)-1H-pyrazolo[3,4-b]pyridine

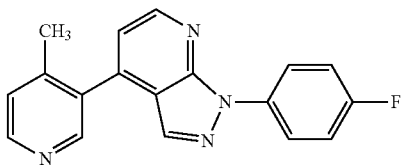

(3)

Example 3 was prepared according to the general procedure of Example 2. Intermediate 2A (0.32 mmol), potassium carbonate (140 mg, 1.01 mmol), 4-methylpyrimidin-5-ylboronic acid hydrochloride salt (78 mg, 0.45 mmol), NMP (1.0 mL), PdCl₂(dppf)·CH₂Cl₂ (45 mg, 0.056 mmol), and deoxygenated water (50 μL) were heated at 100° C. for 4 h to give 37.5 mg (63%) of the title compound as an off white solid. Purification was done by preparative HPLC (Condition A) using a Phenomenex Luna Axia 30×100 mm S10 column from 15% Solvent B to 85% Solvent B over 12 min, ret. T=9.3 min. ¹H NMR (500 MHz, MeOD) δ ppm 2.36 (s, 3 H) 7.29-7.35 (m, 3 H) 7.54 (d, J=5.19 Hz, 1 H) 8.10 (s, 1 H) 8.26-8.32 (m, 2 H) 8.55 (s, 1 H) 8.57 (d, J=5.19 Hz, 1 H) 8.74 (d, J=4.58 Hz, 1 H). LC/MS (Condition B): ret. T=1.82 min, (M+H)⁺ 305.09. Analytical HPLC: (Condition A): >99%, ret. T=23.46 min, (Condition B): >99%, ret. T=23.49 min, (Condition C): >98%, ret. T=10.4 min, (Condition D): >98%, ret. T=10.6 min.

Example 4

3-(4-(4-aminopyrimidin-5-yl)-1H-pyrazolo[3,4-b]pyridin-1-yl)benzenesulfonamide

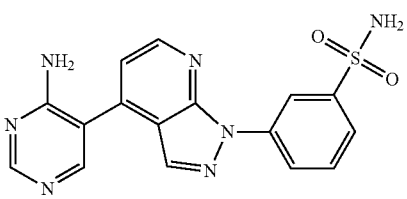

(4)

Example 4 was prepared according to the general procedure of Example 1, except heating at 105° C. for 18 h and using the following materials: Intermediate 1B (32 mg, 0.101 mmol), 4-amino-5-bromopyrimidine (38.6 mg, 0.222 mmol), sodium carbonate (41.8 mg, 0.394 mmol), EtOH:DME:H$_2$O (1.2:2.5:1.0 ratio) (1.0 mL) and tetrakis(triphenylphosphine)palladium(0) (18.6 mg, 0.016 mmol). The title compound was isolated as a white solid (4.3 mg, 11.6%). Purification was done by preparative HPLC (Condition A) using a Phenomenex Luna Axia 30×100 mm S10 column from 5% Solvent B to 100% Solvent B over 12 min, ret. T=4.7 min. $^1$H NMR (500 MHz, DMSO-d$_6$) δ ppm 8.75-8.87 (2 H, m), 8.62-8.71 (1 H, m), 8.52 (1 H, s), 8.42 (1 H, s), 8.28 (1 H, s), 7.79-7.84 (2 H, m), 7.57 (2 H, s), 7.47 (1 H, d, J=4.88 Hz), 6.97 (2 H, br. s.) LC/MS (Condition B): ret. T=1.6 min, (M+H)$^+$ 367.97. Analytical HPLC: (Condition A): >99%, ret. T=11.81 min, (Condition B): >99%, ret. T=13.74 min, (Condition C): >99%, ret. T=3.87 min, (Condition D): >99%, ret. T=4.18 min.

Example 5

1-(4-fluorophenyl)-4-(4-(trifluoromethyl)pyridin-3-yl)-1H-pyrazolo[3,4-b]pyridine

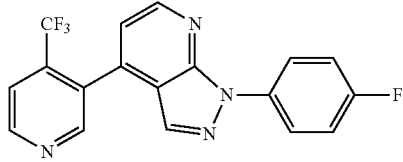

(5)

Intermediate 5A: 1-(4-fluorophenyl)-1H-pyrazolo[3,4-b]pyridin-4-ylboronic acid

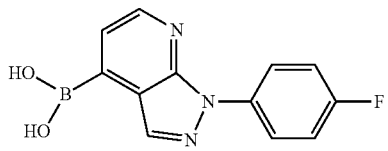

(5A)

To a 16×100 mm reaction vial was added Intermediate 2A (61.8 mg, 0.182 mmol), 4,4,4',4',5,5,5',5'-octamethyl-2,2'-bi(1,3,2-dioxaborolane) (85.5 mg, 0.337 mmol), potassium acetate (77 mg, 0.785 mmol), and DMSO (1 mL). Argon was bubbled into the reaction mixture for 5 minutes. Next, PdCl$_2$(dppf).CH$_2$Cl$_2$ (10 mg, 0.012 mmol) was added and the reaction mixture was heated at 84° C. for 18 h. The desired product was confirmed to be present by LC/MS (Condition B): 88.0%; ret. T=3.4 min; (M+H)$^+$ 258.04.

Example 5

Example 5 was prepared according to the general procedure of Example 1, except that the reaction mixture was heated at 105° C. for 2.25 h, and using the following materials: Intermediate 5A (38.0 mg, 0.148 mmol), 3-bromo-4-(trifluoromethyl)pyridine (76.5 mg, 0.339 mmol), sodium carbonate (59.6 mg, 0.562 mmol), degassed EtOH:DME:H$_2$O (1.2:2.5:1.0 ratio) (1.5 mL) and tetrakis(triphenylphosphine) palladium(0) (17 mg, 0.015 mmol). Example 5 was isolated as an off white solid (28.4 mg, 52.2%). Purification was done by preparative HPLC (Condition A) using a Phenomenex Luna Axia 30×100 mm S10 column from 205% Solvent B to 100% Solvent B over 12 min, ret. T=12.7 min. $^1$H NMR (500 MHz, METHANOL-d$_4$) δ ppm 9.00 (1 H, d, J=4.88 Hz), 8.84 (1 H, s), 8.72-8.78 (1 H, m), 8.26-8.35 (2 H, m), 8.04-8.08 (1 H, m), 7.98 (1 H, d, J=5.19 Hz), 7.29-7.37 (3 H, m). LC/MS (Condition B): ret. T=3.8 min, (M+H)$^+$ 359.04. Analytical HPLC: (Condition A): >99%, ret. T=22.52 min, (Condition B): >99%, ret. T=24.94 min, (Condition C): >99%, ret. T=22.20 min, (Condition D): >99%, ret. T=17.63 min.

Example 6

1-(4-fluorophenyl)-4-(4-methoxypyridin-3-yl)-1H-pyrazolo[3,4-b]pyridine

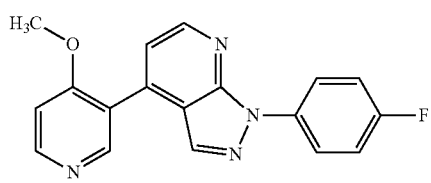

(6)

Example 6 was prepared according to the general procedure of Example 1, except that the reaction mixture was heated at 105° C. for 2.25 h and using the following materials: Intermediate 5A (38.0 mg, 0.148 mmol), 3-iodo-4-methoxypyridine (86.2 mg, 0.367 mmol), sodium carbonate (56.1 mg, 0.529 mmol), degassed EtOH:DME:H$_2$O (1.2:2.5:1.0 ratio) (1.5 mL) and tetrakis(triphenylphosphine)palladium(0) (17 mg, 0.015 mmol). Example 6 was isolated as an off white solid (14.9 mg, 31.1%). Purification was done by preparative HPLC (Condition A) using a Phenomenex Luna Axia 30×100 mm S10 column from 10% Solvent B to 95% Solvent B over 12 min, ret. T=8.6 min. $^1$H NMR (500 MHz, DMSO-d$_6$) δ ppm 8.75 (1 H, d, J=4.88 Hz), 8.64 (1 H, d, J=5.80 Hz), 8.59 (1 H, s), 8.27-8.36 (3 H, m), 7.42-7.51 (3 H, m), 7.35 (1 H, d, J=6.10 Hz), 3.93 (3 H, s). LC/MS (Condition B): ret. T=2.84 min, (M+H)$^+$ 321.05. Analytical HPLC: (Condition A): >99%, ret. T=22.96 min, (Condition B): >99%, ret. T=23.17 min, (Condition C): >99%, ret. T=9.33 min, (Condition D): >99%, ret. T=9.91 min.

Example 7

4-(4-cyclopropylpyrimidin-5-yl)-1-(4-fluorophenyl)-1H-pyrazolo[3,4-b]pyridine

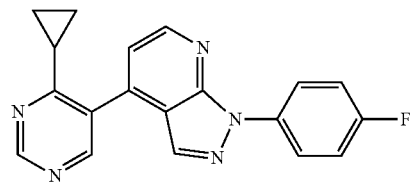

(7)

Intermediate 7A: 5-bromo-4-cyclopropylpyrimidine

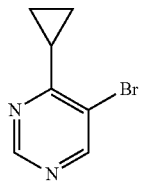

(7A)

To a solution of 5-bromopyrimidine (3 g, 18.87 mmol) in Et₂O (120 mL) and THF (20 ml) was added cyclopropylmagnesium bromide (39.6 mL, 19.81 mmol) at 0° C. The resulting white suspension was stirred at rt for 1 h and quenched with water (0.340 mL, 18.87 mmol) followed by addition of DDQ (4.28 g, 18.87 mmol) in THF (10 ml). The resulting black mixture was stirred at room temperature overnight. The reaction mixture was extracted with EtOAc. The aqueous layer was extracted with EtOAc and the combined organic layer was washed with NaOH (1N) and brine. The crude product was purified by Biotage (0-15% EtOAc/hexanes, 1.2 L) to afford the title compound (700 mg, 20%) as a yellow solid. $^1$H NMR (500 MHz, CCl₃D) δ ppm 8.87 (1 H, s), 8.66 (1 H, s), 2.40-2.56 (1 H, m), 1.13-1.32 (4 H, m).

Example 7

Example 7 was prepared according to the general procedure of Example 1, except that the reaction mixture was heated at 105° C. for 2.25 h, and using the following materials: Intermediate 5A (38.0 mg, 0.148 mmol), Intermediate 7A (55 mg, 0.276 mmol), sodium carbonate (61.5 mg, 0.580 mmol), degassed EtOH:DME:H₂O (1.2:2.5:1.0 ratio) (1.5 mL) and tetrakis(triphenylphosphine) palladium(0) (17 mg, 0.015 mmol). Example 7 was isolated as a tan solid (21.2 mg, 29.5%). Purification was done by preparative HPLC (Condition A) using a Phenomenex Luna 30×100 mm S10 column from 30% Solvent B to 100% Solvent B over 10 min, ret. T=11.1 min. $^1$H NMR (500 MHz, DMSO-d₆) δ ppm 1.05 (d, J=3.05 Hz, 2 H) 1.24 (s, 2 H) 1.89-1.97 (m, 1 H) 7.46 (d, J=8.55 Hz, 2 H) 7.53 (dd, J=9.31, 4.73 Hz, 1 H) 8.29-8.35 (m, 2 H) 8.35-8.43 (m, 1 H) 8.75-8.79 (m, 1 H) 8.79-8.86 (m, 1 H) 9.12-9.18 (m, 1 H). LC/MS (Condition B): ret. T=4.0 min, (M+H)⁺ 332.03. Analytical HPLC: (Condition A): >99%, ret. T=25.49 min, (Condition B): >99%, ret. T=25.41 min, (Condition C): >99%, ret. T=20.9 min, (Condition D): >99%, ret. T=16.45 min.

Example 8

5-(1-(4-fluorophenyl)-1H-pyrazolo[3,4-b]pyridin-4-yl)pyrimidin-4-amine

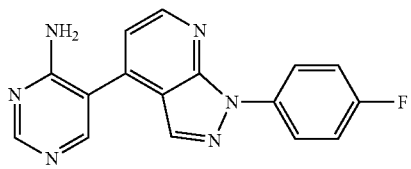

(8)

Example 8 was prepared according to the general procedure of Example 1, except that the reaction mixture was heated at 105° C. for 2.25 h, and using the following materials: Intermediate 5A (38.0 mg, 0.148 mmol), 5-bromopyrimidin-4-amine (55.2 mg, 0.317 mmol), sodium carbonate (59.2 mg, 0.559 mmol), degassed EtOH:DME:H₂O (1.2:2.5:1.0 ratio) (1.5 mL) and tetrakis(triphenylphosphine)palladium(0) (17 mg, 0.015 mmol). Example 8 was isolated as a white solid (15.2 mg, 33.0%). Purification was done by preparative HPLC (Condition A) using a Phenomenex Luna Axia 30×100 mm S10 column from 10% Solvent B to 90% Solvent B over 12 min, ret. T=7.4 min. $^1$H NMR (500 MHz, DMSO-d₆) δ ppm 8.65-8.85 (1 H, m), 8.44-8.60 (1 H, m), 8.21-8.39 (4 H, m), 7.36-7.52 (3 H, m), 6.95 (2 H, br. s.). LC/MS (Condition B): ret. T=2.22 min, (M+H)⁺ 307.05. Analytical HPLC: (Condition A): >98%, ret. T=18.63 min, (Condition B): >99%, ret. T=19.30 min, (Condition C): >99%, ret. T=7.15 min, (Condition D): >99%, ret. T=7.56 min.

Example 9

3-(3-(1-(4-fluorophenyl)-1H-pyrazolo[3,4-b]pyridin-4-yl)pyridin-4-yl)oxetan-3-ol

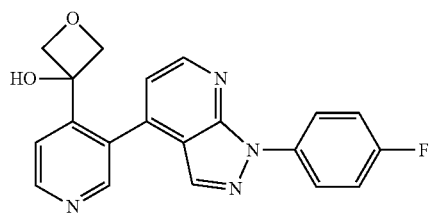

(9)

Intermediate 9A:
3-(3-bromopyridin-4-yl)oxetan-3-ol

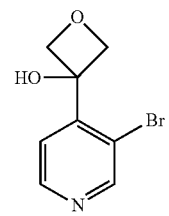

(9A)

To a magnetically stirred solution of 2,2,6,6-tetramethylpiperidine (2.50 g, 17.70 mmol) in dry THF (80 mL) under argon at −78° C. was slowly added over 2 min n-butyllithium (2.50 M in hexanes; 5.6 ml, 14.0 mmol). The reaction mixture was stirred at −78° C. for 5 min and then allowed to warm to about 0° C. over 10 min. The reaction mixture was cooled to −78° C. and slowly over 10 min was added dropwise neat 3-bromopyridine (1.335 ml, 13.61 mmol). The reaction mixture was stirred at −78° C. for 15 min, and then slowly treated with neat oxetan-3-one (870 mg, 12.07 mmol) over 2-3 min. The reaction mixture was then allowed to warm to room temperature slowly over 18 h. The reaction mixture was concentrated in vacuo, then partitioned with ethyl acetate/aqueous saturated NH₄Cl and solid sodium bicarbonate until pH ~8-9 was achieved. The aqueous layers were saturated with sodium chloride and back extracted with ethyl acetate. The organic layers were combined, washed with brine, dried over Na$_2$SO$_4$, filtered, and evaporated to dryness to give a red oil. The crude material was purified by Biotage Silica gel chromatography on a 80 g Thompson Single Step™ silica cartridge using a linear gradient from 100% CH$_2$Cl$_2$ to 100% ethyl acetate over 12 column volumes to give to give 860 mg (31%) of the title compound as a white solid. $^1$H NMR (500 MHz, CDCl$_3$) δ ppm 8.75 (1 H, s), 8.58 (1 H, d, J=5.0 Hz), 7.24 (1 H, d, J=5.0 Hz), 5.16 (2 H, m), 4.91 (2 H, m), 3.12 (1 H, br.s). LC/MS (Condition B): ret. T=1.1 min, (M+H)$^+$ 229.89, 231.89.

Example 9

Example 9 was prepared according to the general procedure of Example 1, except that the reaction mixture was heated at 110° C. for 4 h, and using the following materials: Intermediate 5A (122.9 mg, 0.478 mmol, Intermediate 9A (160 mg, 0.695 mmol), sodium carbonate (201 mg, 1.9 mmol), degassed EtOH:DME:H$_2$O (1.2:2.5:1.0 ratio) (2.5 mL) and tetrakis(triphenylphosphine)palladium(0) (37 mg, 0.067 mmol). Example 9 was isolated as an off-white solid (33.7 mg, 18.3%). Purification was done by preparative HPLC (Condition A) using a Phenomenex Luna Axia 30×100 mm S10 column from 20% Solvent B to 100% Solvent B over 12 min, ret. T=8.88 min. $^1$H NMR (500 MHz, DMSO-d$_6$) δ ppm 4.35 (brs, 2 H) 4.62 (brs, 2 H) 6.82 (s, 1 H) 7.46 (t, J=8.85 Hz, 2 H) 7.51-7.59 (m, 2 H) 8.31-8.37 (m, 3 H) 8.69 (s, 1 H) 8.73 (d, J=4.58 Hz, 1 H) 8.79 (d, J=5.19 Hz, 1 H). LC/MS (Condition B): ret. T=2.90 min, (M+H)$^+$ 363.08. Analytical HPLC: (Condition A): >93%, ret. T=19.64 min, (Condition B): >93%, ret. T=20.26 min, (Condition C): >99%, ret. T=8.15 min, (Condition D): >92%, ret. T=7.66 min.

Example 10

4-(4-chloropyridin-3-yl)-1-(4-fluorophenyl)-1H-pyrazolo[3,4-b]pyridine

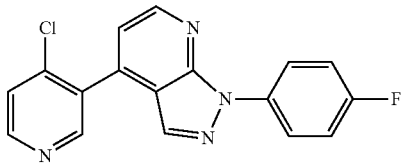

(10)

Example 10 was prepared according to the general procedure of Example 1, except that the reaction mixture was heated at 105° C. for 2 h, and using the following materials: Intermediate 5A (40 mg, 0.156 mmol), 3-bromo-4-chloropyridine (53.6 mg, 0.279 mmol), sodium carbonate (61.3 mg, 0.578 mmol), degassed EtOH:DME:H$_2$O (1.2:2.5:1.0 ratio) (1.5 mL) and tetrakis(triphenylphosphine)palladium(0) (25.3 mg, 0.022 mmol). Example 10 was isolated as an off-white solid (5.7 mg, 11%). Purification was done by preparative HPLC (Condition A) using a Phenomenex Luna Axia 30×100 mm S10 column from 35% Solvent B to 100% Solvent B over 12 min, ret. T=11.8 min. $^1$H NMR (500 MHz, DMSO-d$_6$) δ ppm 8.78-8.86 (2 H, m), 8.74 (1 H, d, J=5.19 Hz), 8.37 (1 H, s), 8.26-8.34 (2 H, m), 7.86 (1 H, d, J=5.19 Hz), 7.43-7.55 (3 H, m). LC/MS (Condition B): ret. T=3.8 min, (M+H)$^+$ 325.00, 326.98. Analytical HPLC: (Condition A): >98%, ret. T=24.69 min, (Condition B): >98%, ret. T=24.45 min, (Condition C): >98%, ret. T=18.88 min, (Condition D): >98%, ret. T=15.00 min.

Example 11

1-(4-fluorophenyl)-4-(pyridin-3-yl)-1H-pyrazolo[3,4-b]pyridine

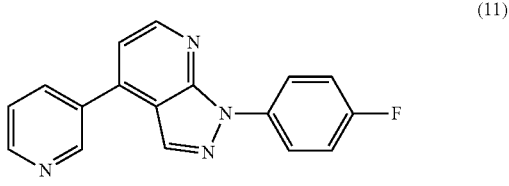 [SMILES: Fc1ccc(-n2ncc3c(-c4cccnc4)ccnc32)cc1]

(11)

Example 11 (3.7 mg, 8%) isolated from Example 10 as an off white solid, preparative HPLC (Condition A) ret. T=8.25 min. $^1$H NMR (500 MHz, DMSO-d$_6$) δ ppm 9.13 (1 H, d, J=2.44 Hz), 8.75-8.83 (2 H, m), 8.70 (1 H, s), 8.27-8.41 (3 H, m), 7.62-7.72 (2 H, m), 7.47 (2 H, t, J=8.85 Hz). LC/MS (Condition B): ret. T=3.0 min, (M+H)$^+$ 291.05. Analytical HPLC: (Condition A): >98%, ret. T=22.67 min, (Condition B): >98%, ret. T=22.54 min, (Condition C): >98%, ret. T=10.42 min, (Condition D): >98%, ret. T=9.66 min.

Example 12

Methyl 3-(1-(4-fluorophenyl)-1H-pyrazolo[3,4-b]pyridin-4-yl)isonicotinate

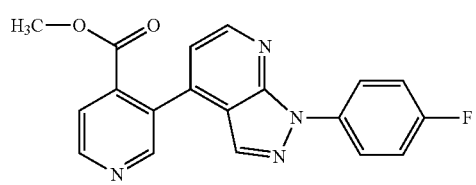

(12)

Example 12 was prepared according to the general procedure of Example 1, except that the reaction mixture was heated at 105° C. for 1 h in a mixture of NMP (1.0 mL) and water (50 μL) and using the following materials: Intermediate 5A (49.4 mg, 0.192 mmol), 3-bromopyridine-4-carboxylic acid methyl ester (0.035 mL, 0.268 mmol), potassium carbonate (93 mg, 0.671 mmol), and PdCl$_2$(dppf).CH$_2$Cl$_2$ (9 mg, 0.012 mmol). Example 12 was isolated as a tan solid (14.2 mg, 19.8%). Purification was done by preparative HPLC (Condition A) using a Phenomenex Luna Axia 30×100 mm S10 column from 30% Solvent B to 100% Solvent B over 12 min, ret. T=10.7 min. LC/MS (Condition B): ret. T=3.6 min, (M+H)$^+$ 349.14. Analytical HPLC: (Condition A): >90%, ret. T=22.18 min, (Condition B): >95%, ret. T=22.85 min, (Condition C): >95%, ret. T=17.14 min, (Condition D): >95%, ret. T=13.96 min.

Example 13

1-(2,4-difluorophenyl)-4-(4-methylpyridin-3-yl)-1H-pyrazolo[3,4-b]pyridine

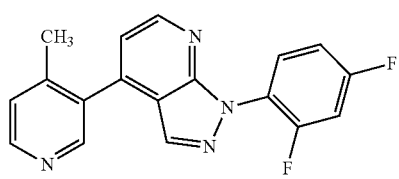

(13)

Intermediate 13A: 1-(2,4-difluorophenyl)-4-iodo-1H-pyrazolo[3,4-b]pyridine

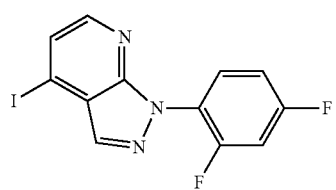

(13A)

To a dry 16×100 mm Chem-Glass reaction tube under N₂ was added 2-fluoro-4-iodonicotinaldehyde (5 g, 19.92 mmol), (2,4-difluorophenyl)hydrazine (3.01 g, 20.92 mmol) and anhydrous NMP (35 mL). The reaction mixture was flushed with argon, securely capped, stirred for 20 min at room temp, and then placed in a 180° C. oil bath for 4 h. The reaction mixture was then allowed to stir at room temperature for 72 h. The reaction mixture was diluted with EtOAc (1200 mL) and the organic layer was extracted with water (6×350 mL), brine (1×100 mL), dried over Na$_2$SO$_4$, filtered, and evaporated to dryness. The residue was purified by Biotage Silica gel chromatography on a 300 g Thompson Single Step™ silica cartridge using a linear gradient from 100% hexanes to 100% dichloromethane over 10 column volumes to give 4.53 g (44.6%) of Intermediate 13A, as a light yellow solid that contained 28% of the uncyclized hydrazone intermediate ((E)-3-(2-(2,4-difluorophenyl)hydrazono)methyl)-2-fluoro-4-iodopyridine). $^1$H NMR (500 MHz, CCl$_3$D) δ ppm 8.21 (1 H, d, J=4.58 Hz), 8.14 (1 H, s), 7.59-7.71 (2 H, m), 7.10 (2 H, td, J=7.55, 3.81 Hz). LC/MS (Condition A): T=3.7 min, (M+H)$^+$ 357.90.

Example 13

To a solution of Intermediate 13A (85 mg, 0.238 mmol) in NMP (1.0 mL) was added 4-methylpyridine-3-boronic acid (37.5 mg, 0.274 mmol) and potassium carbonate (109 mg, 0.785 mmol). The reaction mixture was degassed by bubbling with argon for 10 minutes. The reaction mixture was flushed with argon and then treated with PdCl$_2$(dppf).CH$_2$Cl$_2$ (19.44 mg, 0.024 mmol). The reaction mixture was again flushed with argon, securely capped and heated at 105° C. for 4 h. Following the general workup and purification procedures as described in Example 1, 26.2 mg (33.8%) of the title compound was obtained as an off white solid. Purification was done by preparative HPLC (Condition A) using a Phenomenex Luna Axia 30×100 mm S10 column from 15% Solvent B to 90% Solvent B over 12 min, ret. T=7.4 min. $^1$H NMR (500 MHz, METHANOL-d$_4$) δ ppm 8.68 (1 H, d, J=4.58 Hz), 8.50-8.61 (2 H, m), 8.19 (1 H, s), 7.70-7.82 (1 H, m), 7.55 (1 H, d, J=5.19 Hz), 7.29-7.40 (2 H, m), 7.19-7.28 (1 H, m), 2.38 (3 H, s). LC/MS (Condition B): ret. T=2.4 min, (M+H)$^+$ 323.07. Analytical HPLC: (Condition A): >99, ret. T=7.91 min, (Condition B): >99, ret. T=8.12 min, (Condition C): >99%, ret. T=6.96 min, (Condition D): >99, ret. T=7.36 min.

Examples 14-60

Examples 14 to 60 were prepared according to the following general procedure: To a 4 mL vial was added the desired hydrazine HCl salt (0.25 mmol), polymer bound MP carbonate resin (200 mg, 3.03 mmol/gram from Argonaut Tech (cat 800269)) and anhydrous NMP (0.5 mL). The vials were capped and placed on a shaker at room temperature for 2 h. The resulting solution was removed from the resin by pipette, rinsed with anhydrous NMP (2×250 μL) and added to a 16×100 mm reaction tube containing 2-fluoro-4-iodonicotinaldehyde (50 mg, 0.199 mmol). The resulting solution was flushed with argon, securely capped and heated at either 165° C. for 45 min to 1.5 h or 185° C. for 30 min to 5 h, depending on the hydrazine substitution pattern. After heating was complete, the reaction mixtures were cooled to room temperature, treated with 4-methylpyridin-3-ylboronic acid, 1.00HCl (45-55 mg, 0.260-0.317 mmol), potassium carbonate (85 mg, 0.615 mmol), water (50 μL, 2.78 mmol) and PdCl$_2$(dppf).CH$_2$Cl$_2$ (15 mg, 0.018 mmol), flushed with argon and heated to 105° C. for 4 h. The reaction mixtures were diluted with DMF (400 mL), filtered through either a 0.45 uM frit attached to a single-use Waters C-18 sep-pak light cartridge (part # WAT023501), or a StratoSpheres™ SPE PL-Thiol MP SPE resin cartridge (500 mg/6 mL tube, 1.5 mmol, nominal, part # PL3582-CM89FL, batch # SPEMP THIOL 004), diluted to a total volume of 1.8 mL with DMF. The compounds were purified on a Dionex APS-3000 Reverse Phase Preparative HPLC system on a Waters X-Bridge 19×150 mm S10 C18 column using a gradient from 30% solvent B/70% solvent A to 100% solvent B over 29 min with a flow rate of 20 mL/min, monitoring at a wavelength of 220 nM. Solvent A: 5% MeOH/95% water/20 mM NH$_4$OAc and Solvent B: 95% MeOH/5% water/20 mM NH$_4$OAc.

TABLE 1

| Ex. | R | Compound Name | LC/MS* ret. T (min.) | [M + H]+ |
|---|---|---|---|---|
| 14 | (2-pyridyl) | 4-(4-methylpyridin-3-yl)-1-(pyridin-2-yl)-1H-pyrazolo[3,4-b]pyridine | 2.58 | 288.12 |

TABLE 1-continued

| Ex. | R | Compound Name | LC/MS* ret. T (min.) | [M + H]+ |
|---|---|---|---|---|
| 15 | 2,5-dichlorophenyl | 1-(2,5-dichlorophenyl)-4-(4-methylpyridin-3-yl)-1H-pyrazolo[3,4-b]pyridine | 3.91 | 355.04 |
| 16 | 2,4,6-trifluorophenyl | 4-(4-methylpyridin-3-yl)-1-(2,4,6-trifluorophenyl)-1H-pyrazolo[3,4-b]pyridine | 3.01 | 340.84 |
| 17 | 2,5-difluorophenyl | 1-(2,5-difluorophenyl)-4-(4-methylpyridin-3-yl)-1H-pyrazolo[3,4-b]pyridine | 3.46 | 323.11 |
| 18 | 3-chloro-4-fluorophenyl | 1-(3-chloro-4-fluorophenyl)-4-(4-methylpyridin-3-yl)-1H-pyrazolo[3,4-b]pyridine | 4.67 | 339.06 |
| 19 | 2-chloro-5-(trifluoromethyl)phenyl | 1-(2-chloro-5-(trifluoromethyl)phenyl)-4-(4-methylpyridin-3-yl)-1H-pyrazolo[3,4-b]pyridine | 4.06 | 389.06 |
| 20 | 3-fluoro-2-methoxyphenyl | 1-(3-fluoro-2-methoxyphenyl)-4-(4-methylpyridin-3-yl)-1H-pyrazolo[3,4-b]pyridine | 3.98 | 335.28 |
| 21 | tert-butyl | 1-tert-butyl-4-(4-methylpyridin-3-yl)-1H-pyrazolo[3,4-b]pyridine | 3.39 | 267.53 |
| 22 | 3-CO$_2$H phenyl | 3-(4-(4-methylpyridin-3-yl)-1H-pyrazolo[3,4-b]pyridin-1-yl)benzoic acid | 1.98 | 331.12 |
| 23 | 3-(trifluoromethyl)pyridin-2-yl | 4-(4-methylpyridin-3-yl)-1-(3-(trifluoromethyl)pyridin-2-yl)-1H-pyrazolo[3,4-b]pyridine | 2.95 | 356.11 |
| 24 | cyclohexylmethyl | 1-(cyclohexylmethyl)-4-(4-methylpyridin-3-yl)-1H-pyrazolo[3,4-b]pyridine | 4.22 | 307.17 |
| 25 | 3-chloropyridin-2-yl | 1-(3-chloropyridin-2-yl)-4-(4-methylpyridin-3-yl)-1H-pyrazolo[3,4-b]pyridine | 2.65 | 322.09 |
| 26 | 3-chloro-2-methylphenyl | 1-(3-chloro-2-methylphenyl)-4-(4-methylpyridin-3-yl)-1H-pyrazolo[3,4-b]pyridine | 3.95 | 335.10 |
| 27 | cyclohexyl | 1-cyclohexyl-4-(4-methylpyridin-3-yl)-1H-pyrazolo[3,4-b]pyridine | 3.50 | 292.95 |
| 28 | isobutyl | 1-isobutyl-4-(4-methylpyridin-3-yl)-1H-pyrazolo[3,4-b]pyridine | 3.37 | 267.17 |
| 29 | 4-fluorobenzyl | 1-(4-fluorobenzyl)-4-(4-methylpyridin-3-yl)-1H-pyrazolo[3,4-b]pyridine | 3.47 | 319.12 |
| 30 | 3-chloro-5-fluorophenyl | 1-(3-chloro-5-fluorophenyl)-4-(4-methylpyridin-3-yl)-1H-pyrazolo[3,4-b]pyridine | 6.18 | 339.22 |

TABLE 1-continued

Common structure: 4-(4-methylpyridin-3-yl)-1-R-1H-pyrazolo[3,4-b]pyridine

| Ex. | R | Compound Name | LC/MS* ret. T (min.) | [M + H]+ |
|---|---|---|---|---|
| 31 | 2-morpholinoethyl | 4-(2-(4-(4-methylpyridin-3-yl)-1H-pyrazolo[3,4-b]pyridin-1-yl)ethyl)morpholine | 3.93 | 324.21 |
| 32 | 5-chloropyridin-2-yl | 1-(5-chloropyridin-2-yl)-4-(4-methylpyridin-3-yl)-1H-pyrazolo[3,4-b]pyridine | 3.24 | 322.09 |
| 33 | tetrahydro-2H-pyran-4-yl | 4-(4-methylpyridin-3-yl)-1-(tetrahydro-2H-pyran-4-yl)-1H-pyrazolo[3,4-b]pyridine | 2.61 | 295.15 |
| 34 | benzo[d]thiazol-2-yl | 2-(4-(4-methylpyridin-3-yl)-1H-pyrazolo[3,4-b]pyridin-1-yl)benzo[d]thiazole | 4.28 | 344.26 |
| 35 | 2-(trifluoromethyl)phenyl | 4-(4-methylpyridin-3-yl)-1-(2-(trifluoromethyl)phenyl)-1H-pyrazolo[3,4-b]pyridine | 3.04 | 354.79 |
| 36 | 2-methylpyridin-4-yl | 4-(4-methylpyridin-3-yl)-1-(2-methylpyridin-4-yl)-1H-pyrazolo[3,4-b]pyridine | 3.15 | 302.17 |
| 37 | cyclobutyl | 1-cyclobutyl-4-(4-methylpyridin-3-yl)-1H-pyrazolo[3,4-b]pyridine | 3.97 | 265.24 |
| 38 | 6-fluoropyridin-2-yl | 1-(6-fluoropyridin-2-yl)-4-(4-methylpyridin-3-yl)-1H-pyrazolo[3,4-b]pyridine | 3.47 | 306.25 |
| 39 | 5-(trifluoromethyl)pyridin-2-yl | 4-(4-methylpyridin-3-yl)-1-(5-(trifluoromethyl)pyridin-2-yl)-1H-pyrazolo[3,4-b]pyridine | 4.22 | 356.24 |
| 40 | 2-methyl-4-cyanooxazol-5-yl | 2-methyl-5-(4-(4-methylpyridin-3-yl)-1H-pyrazolo[3,4-b]pyridin-1-yl)oxazole-4-carbonitrile | 2.61 | 317.14 |
| 41 | 3-methoxyphenyl | 1-(3-methoxyphenyl)-4-(4-methylpyridin-3-yl)-1H-pyrazolo[3,4-b]pyridine | 3.42 | 317.38 |
| 42 | 4-methoxybenzyl | 1-(4-methoxybenzyl)-4-(4-methylpyridin-3-yl)-1H-pyrazolo[3,4-b]pyridine | 4.14 | 331.29 |
| 43 | 2-methoxybenzyl | 1-(2-methoxybenzyl)-4-(4-methylpyridin-3-yl)-1H-pyrazolo[3,4-b]pyridine | 4.26 | 331.28 |
| 44 | 3-methoxybenzyl | 1-(3-methoxybenzyl)-4-(4-methylpyridin-3-yl)-1H-pyrazolo[3,4-b]pyridine | 4.13 | 331.28 |
| 45 | benzyl | 1-benzyl-4-(4-methylpyridin-3-yl)-1H-pyrazolo[3,4-b]pyridine | 4.99 | 301.18 |
| 46 | 3-bromopyridin-2-yl | 1-(3-bromopyridin-2-yl)-4-(4-methylpyridin-3-yl)-1H-pyrazolo[3,4-b]pyridine | 2.59 | 366 |
| 47 | o-tolyl | 4-(4-methylpyridin-3-yl)-1-o-tolyl-1H-pyrazolo[3,4-b]pyridine | 4.99 | 301.19 |

TABLE 1-continued

| Ex. | R | Compound Name | LC/MS* ret. T (min.) | [M + H]+ |
|---|---|---|---|---|
| 48 | 2-methoxyphenyl | 1-(2-methoxyphenyl)-4-(4-methylpyridin-3-yl)-1H-pyrazolo[3,4-b]pyridine | 4.39 | 317.23 |
| 49 | 4-SO₂NH₂ phenyl | 4-(4-(4-methylpyridin-3-yl)-1H-pyrazolo[3,4-b]pyridin-1-yl)benzenesulfonamide | 366.12 | 4.11 |
| 50 | 5-fluoro-2-methylphenyl | 1-(5-fluoro-2-methylphenyl)-4-(4-methylpyridin-3-yl)-1H-pyrazolo[3,4-b]pyridine | 5.21 | 319.15 |
| 51 | 3-(trifluoromethyl)phenyl | 4-(4-methylpyridin-3-yl)-1-(3-(trifluoromethyl)phenyl)-1H-pyrazolo[3,4-b]pyridine | 6.48 | 355.14 |
| 52 | 3,4-difluorophenyl | 1-(3,4-difluorophenyl)-4-(4-methylpyridin-3-yl)-1H-pyrazolo[3,4-b]pyridine | 6.11 | 323.18 |
| 53 | 2-isopropylphenyl | 1-(2-isopropylphenyl)-4-(4-methylpyridin-3-yl)-1H-pyrazolo[3,4-b]pyridine | 5.64 | 329.22 |
| 54 | 2-ethoxyphenyl | 1-(2-ethoxyphenyl)-4-(4-methylpyridin-3-yl)-1H-pyrazolo[3,4-b]pyridine | 4.78 | 331.23 |
| 55 | 2-chloro-6-fluorobenzyl | 1-(2-chloro-6-fluorobenzyl)-4-(4-methylpyridin-3-yl)-1H-pyrazolo[3,4-b]pyridine | 5.38 | 353.12 |
| 56 | 1,1-dioxidotetrahydrothiophen-3-yl | 1-(1,1-dioxidotetrahydrothiophen-3-yl)-4-(4-methylpyridin-3-yl)-1H-pyrazolo[3,4-b]pyridine | 2.77 | 329.12 |
| 57 | 2,6-difluorophenyl | 1-(2,6-difluorophenyl)-4-(4-methylpyridin-3-yl)-1H-pyrazolo[3,4-b]pyridine | 3.81 | 323.1 |
| 58 | 5-chloro-2-fluorophenyl | 1-(5-chloro-2-fluorophenyl)-4-(4-methylpyridin-3-yl)-1H-pyrazolo[3,4-b]pyridine | 4.57 | 339.09 |
| 59 | 2-bromophenyl | 1-(2-bromophenyl)-4-(4-methylpyridin-3-yl)-1H-pyrazolo[3,4-b]pyridine | 3.98 | 365.06 |
| 60 | 3-bromophenyl | 1-(3-bromophenyl)-4-(4-methylpyridin-3-yl)-1H-pyrazolo[3,4-b]pyridine | 5.83 | 365.05 |

*LC/MS retention times for Compounds 20-66 were obtained on a Waters Analytical LC/MS system using a Supelco Ascentis Express 4.6 × 50 mm S2.7 C18 column with a gradient from 100% solvent A to 100% solvent B over 10 min with a flow rate of 2 mL/min, monitoring at a wavelength of 220 nM. Solvent A: 5% ACN/95% water/10 mM NH₄OAc and Solvent B: 95% ACN/5% water/10 mM NH₄OAc.

Example 61

4-(4-(dichloromethyl)pyridin-3-yl)-1-(2,4-difluorophenyl)-1H-pyrazolo[3,4-b]pyridine

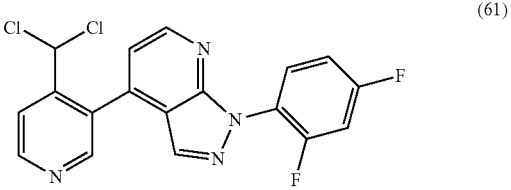 [SMILES: Fc1ccc(-n2ncc3c(-c4cnccc4C(Cl)Cl)ccnc32)c(F)c1]

(61)

To a solution of the compound of Example 13 (11.5 mg, 0.036 mmol) in acetonitrile (2.0 mL) was added N-chlorosuccinimide (5.24 mg, 0.039 mmol). The reaction mixture was flushed with nitrogen and heated at 80° C. for 60 h. Additional N-chlorosuccinimide (10.4 mg, 0.0789 mmol) was added and the reaction mixture was heated at 90° C. for 7 h. Purification was done by preparative HPLC (Condition A) using a Phenomenex Luna Axia 30×100 mm S10 column from 45% Solvent B to 100% Solvent B over 12 min, ret. T=9.7 min to give 3.5 mg (24.7%) of the title compound as a light tan solid. LC/MS (Condition B): ret. T=3.76 min, (M+H)+ 390.98, 392.95, 394.95. Analytical HPLC: (Condition A): >99%, ret. T=22.70 min, (Condition B): >99%, ret. T=23.14 min, (Condition C): >99%, ret. T=18.76 min, (Condition D): >99%, ret. T=15.98 min.

Example 62

3-(1-(2,4-difluorophenyl)-1H-pyrazolo[3,4-b]pyridin-4-yl)pyridin-4-amine

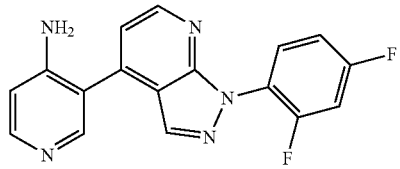

(62)

Intermediate 62A: 4-aminopyrimidin-5-ylboronic acid

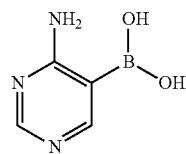

(62A)

To a vial was added 5-bromopyrimidin-4-amine (0.200 g, 1.149 mmol), bis(pinacolato)diboron (0.438 g, 1.724 mmol), and potassium acetate (0.338 g, 3.45 mmol). The vial was capped with a rubber septum and then evacuated and backfilled with $N_2$. Dioxane (0.120 ml) was added via syringe through the septum. The reaction mixture was sparged with $N_2$, then $PdCl_2(dppf).CH_2Cl_2$ (0.042 g, 0.057 mmol) was added. The septum was then replaced with a Teflon screw valve and the vial was sealed. The reaction mixture was heated at 105° C. in a metal pie block. After 18 h, reaction mixture was allowed to cool to room temperature. The reaction mixture was filtered through a disposable fritted funnel and the filter cake washed with EtOAc. The filtrate was concentrated to afford a brown solid. MS (ESI): m/z=140.0 [M+H]+ HPLC Peak ret. T=0.24 minutes was product (HPLC conditions: Column:Luna C18 4.6×30 mm 3 u A:10:90 $H_2O$:ACN $NH_4OAc$/B:10:90 $H_2O$:ACN $NH_4OAc$; 0%-95% B in 2 min; 4 mL/min flow).

Example 62

Example 62 was prepared according to the general procedure in Example 2, except that the reaction mixture was heated at 105° C. for 1.5 h, and using Intermediate 13A (40 mg, 0.112 mmol), sodium carbonate (41.6 mg, 0.392 mmol), Intermediate 62A (61.8 mg, 0.448 mmol), EtOH:DME:$H_2O$ (1.2:2.5:1.0 ratio) (1.5 mL), and tetrakis(triphenylphosphine) palladium(0) (12.9 mg, 0.011 mmol). Example 62 was isolated as an off white solid (11.5 mg, 31.4%). Purification was done by preparative HPLC (Condition A) using a Phenomenex Luna Axia 30×100 mm S10 column from 10% Solvent B to 90% Solvent B over 12 min, ret. T=6.86 min. $^1$H NMR (500 MHz, METHANOL-$d_4$) δ ppm 8.58-8.70 (1 H, m), 8.24-8.30 (1 H, m), 8.20 (1 H, br. s.), 8.12 (1 H, d, J=5.80 Hz), 7.69-7.80 (1 H, m), 7.37-7.46 (1 H, m), 7.28-7.36 (1 H, m), 7.19-7.27 (1 H, m), 6.81-6.90 (1 H, m). LC/MS (Condition B): ret. T=2.36 min, (M+H)+ 324.02. Analytical HPLC: (Condition A): >98%, ret. T=17.77 min, (Condition B): >98%, ret. T=16.68 min, (Condition C): >98%, ret. T=6.26 min, (Condition D): >98%, ret. T=6.76 min.

Example 63

2-(3-(1-(2,4-difluorophenyl)-1H-pyrazolo[3,4-b]pyridin-4-yl)pyridin-4-yl)acetonitrile

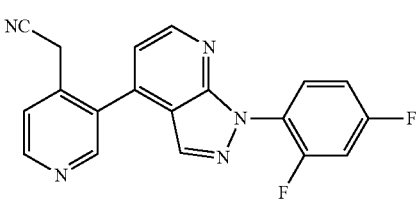

(63)

Intermediate 63A: 1-(2,4-difluorophenyl)-1H-pyrazolo[3,4-b]pyridin-4-ylboronic acid

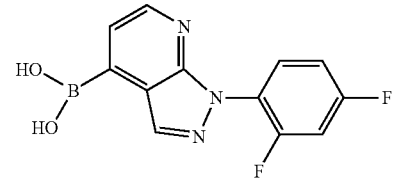

(63A)

Intermediate 63A was prepared according to the general procedure described in Intermediate 5A, except that the reaction mixture was heated at 85° C. for 75 min, using Intermediate 13A (100 mg, 0.280 mmol), 4,4,4',4',5,5,5',5'-octamethyl-2,2'-bi(1,3,2-dioxaborolane) (133.1 mg, 0.524 mmol), potassium acetate (115.0 mg, 1.172 mmol), and DMSO (1.5 mL). The desired product was confirmed to be present by LC/MS (Condition B): 76%; ret. T=2.9 min; (M+H)+ 276.00.

Example 63

Example 63 was prepared according to the general procedure in Example 1, except heating at 115° C. for 3 h, and using the following materials: Intermediate 63A (77.0 mg, 0.280 mmol), 2-(3-bromopyridin-4-yl)acetonitrile (55.2 mg, 0.280 mmol), sodium carbonate (248.6 mg, 2.34 mmol), EtOH:DME:$H_2O$ (1.2:2.5:1.0 ratio) (1.75 mL) and tetrakis(triphenylphosphine) palladium(0) (47.1 mg, 0.041 mmol). Example 63 was isolated as a dark tan solid (23.6 mg, 23.9%).

Purification was done by preparative HPLC (Condition A) using a Phenomenex Luna Axia 30×100 mm S10 column from 15% Solvent B to 100% Solvent B over 12 min, ret. T=8.3 min. $^1$H NMR (500 MHz, DMSO-$d_6$) δ ppm 8.81 (1 H, d, J=5.19 Hz), 8.69-8.76 (2 H, m), 8.37 (1 H, s), 7.78-7.88 (1 H, m), 7.72 (1 H, d, J=4.88 Hz), 7.61-7.70 (1 H, m), 7.45 (1 H, d, J=4.58 Hz), 7.32-7.41 (1 H, m), 4.16 (2 H, s). LC/MS (Condition B): ret. T=2.69 min, (M+H)$^+$ 347.97. Analytical HPLC: (Condition A): >98%, ret. T=18.83 min, (Condition B): >97%, ret. T=17.29 min, (Condition C): >97%, ret. T=11.24 min, (Condition D): >97%, ret. T=10.35 min.

Example 64

1-(2,4-difluorophenyl)-4-(4-methylpyrimidin-5-yl)-1H-pyrazolo[3,4-b]pyridine (64)

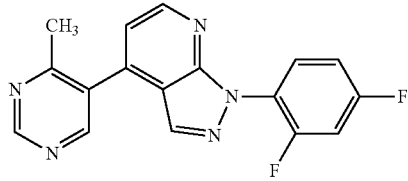

Example 64 was prepared according to the general procedure in Example 1, except heating at 90° C. for 18 h, and using the following materials: Intermediate 63A (35.0 mg, 0.127 mmol), 5-bromo-4-methylpyrimidine (41.2 mg, 0.238 mmol), sodium carbonate (58.9 mg, 0.556 mmol), EtOH:DME:H$_2$O (1.2:2.5:1.0 ratio) (1.0 mL) and tetrakis(triphenylphosphine) palladium(0) (17.5 mg, 0.0151 mmol). Example 64 was isolated as a white solid (25.1 mg, 60.7%). Purification was done by preparative HPLC (Condition A) using a Phenomenex Luna Axia 30×100 mm S10 column from 18% Solvent B to 100% Solvent B over 12 min, ret. T=9.2 min, followed by Biotage Silica gel chromatography on a 4 g Thompson Single Step™ silica cartridge using a linear gradient from 100% hexanes to 100% (1:1 acetone/hexanes) over 10 column volumes. $^1$H NMR (500 MHz, CCl$_3$D) δ ppm 9.27 (1 H, s), 8.68-8.79 (2 H, m), 8.09 (1 H, s), 7.71 (1 H, td, J=8.62, 5.95 Hz), 7.21 (1 H, d, J=4.58 Hz), 7.13 (2 H, td, J=7.86, 5.65 Hz), 2.58 (3 H, s). LC/MS (Condition B): ret. T=3.22 min, (M+H)$^+$ 324.13. Analytical HPLC: (Condition A): >99%, ret. T=18.26 min, (Condition B): >99%, ret. T=18.09 min, (Condition C): >99%, ret. T=12.33 min, (Condition D): >99%, ret. T=10.15 min.

Example 65

4-(4-(Azetidin-1-yl)pyridin-3-yl)-1-(2,4-difluorophenyl)-1H-pyrazolo[3,4-b]pyridine (65)

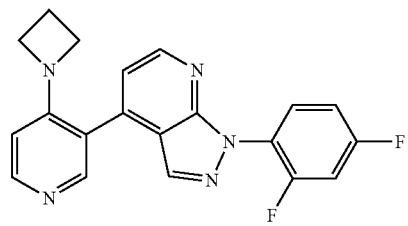

Intermediate 65A: 4-(azetidin-1-yl)-3-bromopyridine (65A)

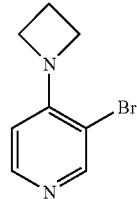

To a 16×100 mm reaction tube under N$_2$ was added, 3-bromo-4-chloropyridine (320 mg, 1.663 mmol), cesium carbonate (1.65 g, 5.06 mmol), and 1,2-dimethoxyethane (3 mL). The reaction mixture was flushed with nitrogen and then treated with azetidine (210 µL, 3.12 mmol). The reaction mixture was securely capped, stirred at room temperature for 5 min, then heated at 90° C. for 18 h. The reaction mixture was filtered through a small Celite plug by gravity, washed with dichloromethane (30 mL) and the volatiles were evaporated in vacuo to give 350 mg (99%) of the title compound as a pale yellow solid.

Example 65

Example 65 was prepared according to the general procedure in Example 1, except heating at 90° C. for 18 h, and using the following materials: Intermediate 65A (35.2 mg, 0.128 mmol), Intermediate 63A (50.7 mg, 0.238 mmol), sodium carbonate (50 mg, 0.472 mmol), EtOH:DME:H$_2$O (1.2:2.5:1.0 ratio) (1.0 mL) and tetrakis(triphenylphosphine) palladium(0) (14 mg, 0.012 mmol). Example 65 was isolated as a white solid (20.8 mg, 44.7%). Purification was done by preparative HPLC (Condition A) using a Phenomenex Luna Axia 30×100 mm S10 column from 20% Solvent B to 85% Solvent B over 12 min, ret. T=6.9 min. $^1$H NMR (500 MHz, CCl$_3$D) δ ppm 8.60 (1 H, d, J=4.58 Hz), 8.22-8.37 (2 H, m), 8.18 (1 H, s), 7.68 (1 H, td, J=8.70, 5.80 Hz), 7.19 (1 H, d, J=4.58 Hz), 7.03-7.14 (2 H, m), 6.49 (1 H, d, J=5.80 Hz), 3.66 (4 H, brs), 2.10-2.30 (2 H, m). LC/MS (Condition B): ret. T=2.39 min, (M+H)$^+$ 364.01. Analytical HPLC: (Condition A): >99%, ret. T=20.74 min, (Condition B): >99%, ret. T=22.80 min, (Condition C): >99%, ret. T=7.73 min, (Condition D): >99%, ret. T=8.82 min.

Example 66

4-(4-(azetidin-1-yl)pyrimidin-5-yl)-1-(2,4-difluorophenyl)-1H-pyrazolo[3,4-b]pyridine (66)

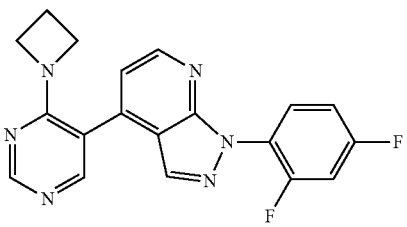

Intermediate 66A:
4-(azetidin-1-yl)-5-iodopyrimidine

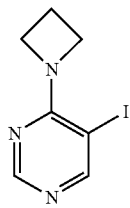

(66A)

To a 16×100 mm reaction tube under $N_2$ was added 4-chloro-5-iodopyrimidine (200 mg, 0.832 mmol), cesium carbonate (817 mg, 2.508 mmol) and 1,2-dimethoxyethane (5 mL). The reaction mixture was flushed with nitrogen and then treated with azetidine (112 µL, 1.662 mmol). The reaction mixture was securely capped, stirred at room temperature for 5 min, and then heated at 90° C. for 18 h. The reaction mixture was filtered through a small Celite plug by gravity, washed with dichloromethane (70 mL) and the solvent was evaporated off in vacuo to give 200 mg (92%) of the title compound as a pale yellow solid.

Example 66

Example 66 was prepared according to the general procedure in Example 1, except heating at 105° C. for 2.5 h, and using the following materials: Intermediate 63A (35 mg, 0.127 mmol), Intermediate 66A (65.8 mg, 0.252 mmol), sodium carbonate (59.9 mg, 0.565 mmol), EtOH:DME:H$_2$O (1.2:2.5:1.0 ratio) (1.0 mL), and tetrakis(triphenylphosphine)palladium(0) (15 mg, 0.013 mmol). Example 66 was isolated as a colorless film (22.5 mg, 48%). Purification was done by preparative HPLC (Condition A) using a Phenomenex Luna Axia 30×100 mm S10 column from 10% Solvent B to 90% Solvent B over 12 min, ret. T=7.5 min. $^1$H NMR (500 MHz, CCl$_3$D) δ ppm 8.74 (1 H, s), 8.66 (1 H, d, J=4.88 Hz), 8.31 (1 H, s), 8.23 (1 H, s), 7.63-7.77 (1 H, m), 7.20 (1 H, d, J=4.88 Hz), 7.08-7.16 (2 H, m), 3.85 (4 H, br. s.), 2.27 (2 H, quin, J=7.7 Hz). LC/MS (Condition B): ret. T=2.31 min, (M+H)$^+$ 365.00. Analytical HPLC: (Condition A): >99%, ret. T=18.74 min, (Condition B): >99%, ret. T=21.04 min, (Condition C): >99%, ret. T=7.17 min, (Condition D): >99%, ret. T=8.11 min.

Example 67

5-(1-(2,4-difluorophenyl)-1H-pyrazolo[3,4-b]pyridin-4-yl)pyrimidin-4-amine

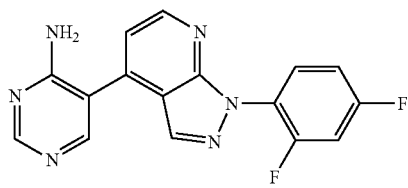

(67)

Example 67 was prepared according to the general procedure in Example 1, except heating at 110° C. for 4.5 h, and using the following materials: Intermediate 63A (308 mg, 1.120 mmol), 5-bromopyrimidin-4-amine (297 mg, 1.707 mmol), sodium carbonate (484 mg, 4.57 mmol), EtOH:DME:H$_2$O (1.2:2.5:1.0 ratio) (5.0 mL) and tetrakis(triphenylphosphine) palladium(0) (81 mg, 0.07 mmol). Example 67 was isolated as a white solid (124.2 mg, 32.3%). Purification was done by preparative HPLC (Condition A) using a Phenomenex Luna Axia 30×100 mm S10 column from 15% Solvent B to 80% Solvent B over 12 min, ret. T=6.0 min. $^1$H NMR (500 MHz, DMSO-d$_6$) δ ppm 8.65 (1 H, d, J=4.88 Hz), 8.51 (1 H, s), 8.37 (1 H, s), 8.28 (1 H, s), 7.77 (1 H, td, J=8.70, 6.10 Hz), 7.60-7.70 (1 H, m), 7.31-7.45 (2 H, m), 6.98 (2 H, br. s.). LC/MS (Condition B): ret. T=1.99 min, (M+H)$^+$ 325.04. Analytical HPLC: (Condition A): >99%, ret. T=15.36 min, (Condition B): >99%, ret. T=16.81 min, (Condition C): >99%, ret. T=5.47 min, (Condition D): >99%, ret. T=5.81 min.

Example 68

1-(5-(1-(2,4-difluorophenyl)-1H-pyrazolo[3,4-b]pyridin-4-yl)pyrimidin-4-yl)azetidin-3-ol

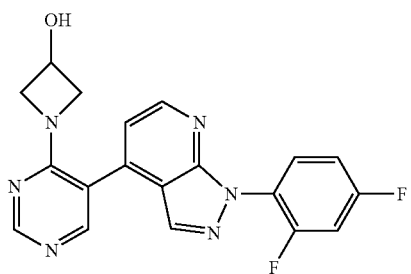

(68)

Intermediate 68A:
1-(5-iodopyrimidin-4-yl)azetidin-3-ol

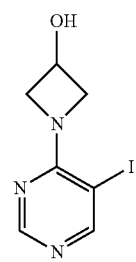

(68A)

To a 150 mL pressure reaction bottle under $N_2$ was added 4-chloro-5-iodopyrimidine (884 mg, 3.68 mmol), azetidin-3-ol, HCl (1.29 g, 11.8 mmol), cesium carbonate (8.40 g, 25.8 mmol), and 1,2-dimethoxyethane (19 mL). The reaction mixture was stirred, flushed with argon for 5 min, securely capped and heated at 120° C. for 2 h. The reaction mixture was filtered reaction through small Celite plug by gravity, washed with dichloromethane (125 mL) and the volatiles evaporated in vacuo to give 950 mg (93%) of the title compound as a white solid.

Example 68

Example 68 was prepared according to the general procedure in Example 1, except heating at 100° C. for 8 h, and using the following materials: Intermediate 63A (217 mg, 0.793 mmol), Intermediate 68A (380 mg, 1.372 mmol), sodium carbonate (350 mg, 3.30 mmol), EtOH:DME:H₂O (1.2:2.5:1.0 ratio) (3.0 mL) and tetrakis(triphenylphosphine)palladium(0) (40 mg, 0.035 mmol). Example 68 was isolated as a white solid (63 mg, 20.8%). Purification was done by preparative HPLC (Condition A) using a Phenomenex Luna Axia 30×100 mm S10 column from 15% Solvent B to 85% Solvent B over 11 min, ret. T=5.6 min. ¹H NMR (500 MHz, CCl₃D) δ ppm 8.64 (1 H, s), 8.61 (1 H, d, J=4.88 Hz), 8.26 (1 H, s), 8.20 (1 H, s), 7.62-7.69 (1 H, m), 7.15 (1 H, d, J=4.88 Hz), 7.02-7.11 (2 H, m), 4.54 (1 H, tt, J=6.60, 4.39 Hz), 3.99 (2 H, brs), 3.65 (2 H, brs). LC/MS (Condition B): ret. T=2.05 min, (M+H)⁺ 381.00. Analytical HPLC: (Condition A): >99%, ret. T=15.91 min, (Condition B): >99%, ret. T=17.76 min, (Condition C): >98%, ret. T=5.65 min, (Condition D): >99%, ret. T=6.05 min.

Example 69

5-(1-(2,3,5,6-tetrafluorophenyl)-1H-pyrazolo[3,4-b]pyridin-4-yl)pyrimidin-4-amine

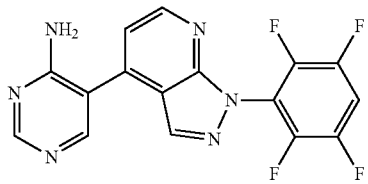

(69)

Intermediate 69A: 4-iodo-1-(2,3,5,6-tetrafluorophenyl)-1H-pyrazolo[3,4-b]pyridine

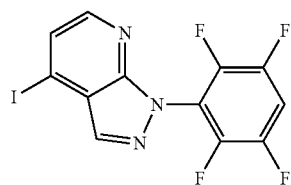

(69A)

To a 15 mL pressure bottle was added 2-fluoro-4-iodonicotinaldehyde (710 mg, 2.83 mmol), (2,3,5,6-tetrafluorophenyl)hydrazine (509 mg, 2.83 mmol), and anhydrous NMP (4 mL). The reaction mixture was flushed with argon, securely capped, and heated at 184° C. for 2.75 h. The reaction mixture was partitioned with ethyl acetate (300 mL), water (125 mL), and brine (50 mL). The organic layer was washed with water (4×40 mL) and brine (75 mL) and the combined aqueous layers were extracted with additional ethyl acetate (300 mL). The second organic layer was washed with water (4×60 mL), and brine (100 mL), and the combined organic layers were dried over sodium sulfate, and evaporated in vacuo to give 1.16 g (quantitative yield) of the title compound as a tan solid. LC/MS (Condition B): ret. T=3.92 min, (M+H)⁺ 393.89.

Intermediate 69B: 1-(2,3,5,6-tetrafluorophenyl)-1H-pyrazolo[3,4-b]pyridin-4-ylboronic acid

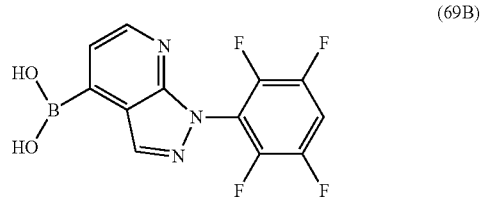 [SMILES: OB(O)c1ccnc2c1cnn2-c1c(F)c(F)cc(F)c1F]

(69B)

To a 48 mL pressure bottle under N₂ was added the compound from Intermediate 69A (1.1 g, 2.8 mmol), 4,4,4',4',5,5,5',5'-octamethyl-2,2'-bi(1,3,2-dioxaborolane (1.17 g, 4.61 mmol), potassium acetate (1.15 g, 11.72 mmol), and anhydrous DMSO (8 mL). Argon was bubbled into the reaction mixture for 5 min and then PdCl₂(dppf).CH₂Cl₂ (71 mg, 0.097 mmol) was added. The reaction mixture was flushed with argon, securely capped, and heated at 105° C. for 75 min. After adding 30 mg more palladium catalyst and 60 mg more 4,4,4',4',5,5,5',5'-octamethyl-2,2'-bi(1,3,2-dioxaborolane, the reaction mixture was heated at 115° C. in an oil bath for an additional 75 min to give the desired intermediate. LC/MS (Condition B): ret. T=3.2 min, (M+H)⁺ 312.03.

Example 69

Example 69 was prepared according to the general procedure in Example 1, except heating at 105° C. for 18 h, and using the following materials: Intermediate 69B (871 mg, 2.8 mmol), 5-bromopyrimidin-4-amine (660 mg, 3.79 mmol), sodium carbonate (1.24 g, 11.70 mmol), EtOH:DME:H₂O (1.2:2.5:1.0 ratio) (8.0 mL) and tetrakis(triphenylphosphine)palladium(0) (50 mg, 0.043 mmol). Example 69 was isolated as a tan solid (33.4 mg, 3.3%). Purification was done by preparative HPLC (Condition A) using a Phenomenex Luna Axia 30×100 mm S10 column from 15% Solvent B to 85% Solvent B over 11 min, ret. T=6.6 min. ¹H NMR (500 MHz, MeOD) δ ppm 7.49 (dd, J=4.73, 1.37 Hz, 1 H) 7.76-7.84 (m, 1 H) 8.33 (s, 1 H) 8.44 (s, 1 H) 8.54 (s, 1 H) 8.71 (dd, J=4.73, 1.37 Hz, 1 H). LC/MS (Condition B): ret. T=2.15 min, (M+H)⁺ 361.03. Analytical HPLC: (Condition A): >99%, ret. T=16.00 min, (Condition B): >99%, ret. T=17.36 min, (Condition C): >97%, ret. T=6.52 min, (Condition D): >98%, ret. T=6.99 min.

Example 70

5-(1-(2,3,4-trifluorophenyl)-1H-pyrazolo[3,4-b]pyridin-4-yl)pyrimidin-4-amine

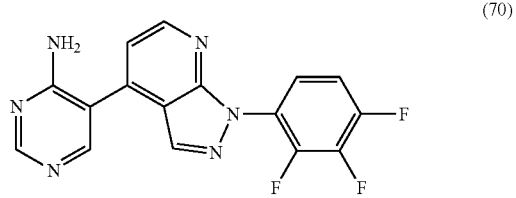 [SMILES: Nc1ncncc1-c1ccnc2c1cnn2-c1ccc(F)c(F)c1F]

(70)

Intermediate 70A: 4-iodo-1-(2,3,4-trifluorophenyl)-1H-pyrazolo[3,4-b]pyridine

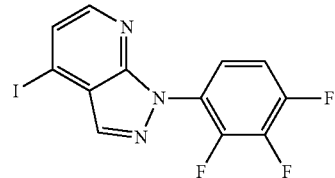

(70A)

To a dry 15 mL ChemGlass pressure bottle under N₂ was added (2,3,4-trifluorophenyl)hydrazine (359 mg, 2.212 mmol), 4-iodo-2-fluoro-3-formylpyridine (555.1 mg, 2.212 mmol), and anhydrous NMP (5 mL). The reaction mixture was flushed with argon, securely capped, and heated at 185° C. for 3 h. The reaction mixture was worked up according to the procedure described in Intermediate 69A. The product was purified by Biotage Silica gel chromatography using a 25 g Thompson Single Step™ silica cartridge with a linear gradient from 100% hexanes to 100% $CH_2Cl_2$ over 12 column volumes gave 162.9 mg (20.4%) of the title compound as a yellow solid. LC/MS (Condition B): ret. T=4.0 min, $(M+H)^+$ 375.93.

Intermediate 70B: 1-(2,3,4-trifluorophenyl)-1H-pyrazolo[3,4-b]pyridin-4-ylboronic acid

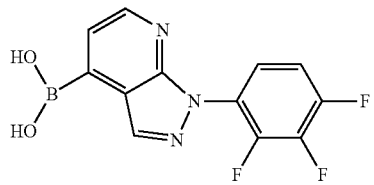

(70B)

To a 48 mL pressure bottle under N₂ was added Intermediate 70A (169.2 mg, 0.451 mmol), 4,4,4',4',5,5,5',5'-octamethyl-2,2'-bi(1,3,2-dioxaborolane) (217 mg, 0.855 mmol), potassium acetate (206 mg, 2.099 mmol) and anhydrous DMSO (4.5 mL). The reaction mixture was flushed with argon, then treated with $PdCl_2(dppf)\cdot CH_2Cl_2$ (28.3 mg, 0.039 mmol). The reaction mixture was again flushed with argon, securely capped and heated at 85° C. for 1 h to give complete conversion to the desired product. LC/MS (Condition B): ret. T=3.3 min, $(M+H)^+$ 294.03.

Example 70

Example 70 was prepared according to the general procedure in Example 1, except heating at 105° C. for 4 h, and using the following materials: Intermediate 70B (132 mg, 0.450 mmol), 5-bromopyrimidin-4-amine (131.4 mg, 0.755 mmol), sodium carbonate (215.1 mg, 2.03 mmol), $EtOH:DME:H_2O$ (1.2:2.5:1.0 ratio) (4.0 mL) and tetrakis(triphenylphosphine)palladium(0) (35.6 mg, 0.031 mmol). Example 70 was isolated as an off white solid (33 mg, 20.3%). Purification was done by preparative HPLC (Condition A) using a Phenomenex Luna Axia 30×100 mm S10 column from 15% Solvent B to 85% Solvent B over 11 min, ret. T=7.0 min. ¹H NMR (500 MHz, METHANOL-d₄) δ ppm 8.69 (1 H, d, J=4.58 Hz), 8.53 (1 H, s), 8.35 (1 H, s), 8.31 (1 H, s), 7.53-7.63 (1 H, m), 7.36-7.48 (2 H, m). LC/MS (Condition B): ret. T=2.3 min, $(M+H)^+$ 343.04. Analytical HPLC: (Condition A): >94%, ret. T=17.54 min, (Condition B): >94%, ret. T=18.79 min, (Condition C): >99%, ret. T=7.35 min, (Condition D): >96%, ret. T=7.85 min.

Example 71

5-(1-(3-bromopyridin-2-yl)-1H-pyrazolo[3,4-b]pyridin-4-yl)pyrimidin-4-amine

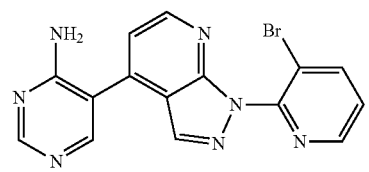

(71)

Intermediate 71A: 1-(3-bromopyridin-2-yl)-4-iodo-1H-pyrazolo[3,4-b]pyridine

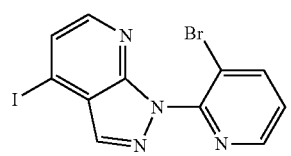

(71A)

To a dry 15 mL ChemGlass pressure bottle under N₂ was added 2-fluoro-4-iodonicotinaldehyde (725 mg, 2.89 mmol), 3-bromo-2-hydrazinylpyridine (543 mg, 2.89 mmol) and anhydrous NMP (Volume: 4.0 mL). The reaction mixture was flushed with argon, securely capped, and heated to 185° C. for 45 min. The reaction mixture was worked up according to the procedure described in Intermediate 69A and the crude product was purified by Biotage Silica gel chromatography using a 12 g Thompson Single Step™ silica cartridge with a linear gradient from 100% $CH_2Cl_2$ to 100% ethyl acetate over 11 column volumes to give 867.4 mg (74.9%) of the title compound as a yellow solid. ¹H NMR (500 MHz, $CCl_3D$) δ ppm 8.64 (1 H, dd, J=4.58, 1.53 Hz), 8.09-8.25 (3 H, m), 7.65 (1 H, d, J=4.58 Hz), 7.37 (1 H, dd, J=7.93, 4.58 Hz). LC/MS (Condition B): ret. T=3.2 min, $(M+H)^+$ 400.81, 402.81.

Example 71

Example 71 was prepared according to the general procedure in Example 1, except that the reaction mixture was heated at 105° C. for 3 h, and the following materials were used: Intermediate 71A (400 mg, 0.998 mmol), Intermediate 62A (399 mg, 2.88 mmol), sodium carbonate (435.3 mg, 4.11 mmol), degassed $EtOH:DME:H_2O$ (1.2:2.5:1.0 ratio) (10 mL) and tetrakis(triphenylphosphine)palladium(0) (55.2 mg, 0.048 mmol). Example 71 was isolated as a white solid (12.1 mg, 3.13%). Purification was done by preparative HPLC (Condition A) using a Phenomenex Luna Axia 30×100 mm S10 column from 0% Solvent B to 45% Solvent B over 11 min, ret. T=7.37 min, followed by Biotage silica gel purification on a 4 g Thompson Single Step™ silica cartridge using a linear gradient form 100% $CH_2Cl_2$ to 100% (15% MeOH/ $CH_2Cl_2$) over 12 column volumes. $^1H$ NMR (500 MHz, METHANOL-$d_4$) δ ppm 8.62-8.73 (2 H, m), 8.54 (1 H, s), 8.29-8.46 (3 H, m), 7.62 (1 H, dd, J=8.09, 4.73 Hz), 7.47 (1 H, d, J=4.88 Hz). LC/MS (Condition B): ret. T=1.7 min, (M+H)$^+$ 367.94, 369.94. Analytical HPLC: (Condition A): 90%, ret. T=12.92 min, (Condition B): >98%, ret. T=12.54 min, (Condition C): >90%, ret. T=3.39 min, (Condition D): >90%, ret. T=3.78 min.

Example 72

5-(1-(pyridin-2-yl)-1H-pyrazolo[3,4-b]pyridin-4-yl) pyrimidin-4-amine

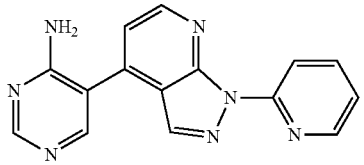

(72)

Example 72 (75.5 mg, 25.9%) was isolated from Example 71 as an off white solid, preparative HPLC (Condition A) ret. T=6.41 min. $^1H$ NMR (500 MHz, DMSO-$d_6$) δ ppm 8.74 (1 H, d, J=4.58 Hz), 8.62-8.69 (1 H, m), 8.52 (1 H, s), 8.34 (1 H, d, J=0.61 Hz), 8.28 (1 H, s), 8.23 (1 H, dd, J=8.24, 0.61 Hz), 8.03-8.16 (1 H, m), 7.39-7.52 (2 H, m), 6.96 (2 H, br. s.). LC/MS (Condition B): ret. T=1.90 min, (M+H)$^+$ 290.21. Analytical HPLC: (Condition A): >99%, ret. T=12.28 min, (Condition B): >99%, ret. T=12.64 min, (Condition C): >95%, ret. T=3.12 min, (Condition D): >99%, ret. T=3.39 min.

Example 73

5-(1-(3-(trifluoromethyl)pyridin-2-yl)-1H-pyrazolo [3,4-b]pyridin-4-yl)pyrimidin-4-amine

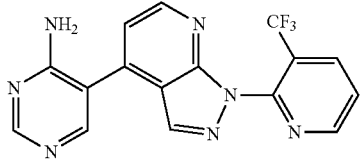

(73)

Intermediate 73A: 4-iodo-1-(3-(trifluoromethyl)pyridin-2-yl)-1H-pyrazolo[3,4-b]pyridine

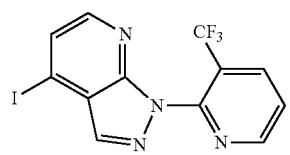

(73A)

To a dry 15 mL ChemGlass pressure bottle under nitrogen was added 3-(trifluoromethyl)pyrid-2-ylhydrazine (499 mg, 2.82 mmol), 4-iodo-2-fluoro-3-formylpyridine (706.8 mg, 2.82 mmol) and anhydrous NMP (4.5 mL). The reaction mixture was flushed with argon, securely capped and heated to 185° C. for 1.5 h. The reaction mixture was worked up according to the procedure described in Intermediate 69A to give 982 mg (89%) of the title compound as an oil. LC/MS (Condition B): ret. T=3.4 min, (M+H)$^+$ 390.94.

Intermediate 73B: 1-(3-(trifluoromethyl)pyridin-2-yl)-1H-pyrazolo[3,4-b]pyridin-4-ylboronic acid

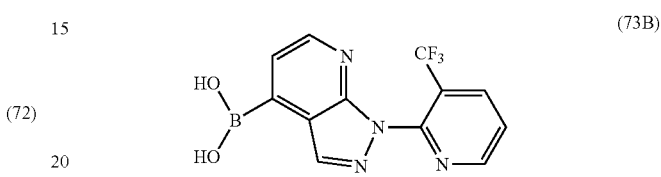

(73B)

To a 48 mL pressure bottle containing Intermediate 73A (495 mg, 1.269 mmol) was added 4,4,4',4',5,5,5',5'-octamethyl-2,2'-bi(1,3,2-dioxaborolane) (569 mg, 2.241 mmol), potassium acetate (571 mg, 5.82 mmol) and anhydrous DMSO (10 mL). The reaction mixture was purged with argon, treated with PdCl$_2$(dppf).CH$_2$Cl$_2$ (56 mg, 0.077 mmol), and heated to 85° C. for 2 h 15 min to give conversion to the desired product. LC/MS (Condition B): ret. T=2.5 min, (M+H)$^+$ 309.07.

Example 73

Example 73 was prepared according to the general procedure in Example 1, except heating at 108° C. for 4 h, and using the following materials: Intermediate 73B (391 mg, 1.269 mmol), 5-bromopyrimidin-4-amine (335.5 mg, 1.928 mmol), sodium carbonate (567 mg, 5.35 mmol), EtOH:DME:H$_2$O (1.2:2.5:1.0 ratio) (10.0 mL) and tetrakis(triphenylphosphine) palladium(0) (52.4 mg, 0.045 mmol). Example 73 was isolated as a light yellow solid (32.6 mg, 7.1%). Purification was done by preparative HPLC (Condition A) using a Phenomenex Luna Axia 30×100 mm S10 column from 15% Solvent B to 75% Solvent B over 11 min, ret. T=4.7 min. $^1H$ NMR (500 MHz, DMSO-$d_6$) δ ppm 8.99 (1 H, d, J=4.58 Hz), 8.57-8.64 (2 H, m), 8.52 (1 H, s), 8.38 (1 H, s), 8.30 (1 H, s), 7.94 (1 H, dd, J=7.78, 4.73 Hz), 7.43 (1 H, d, J=4.88 Hz), 7.01 (2 H, br. s.). LC/MS (Condition B): ret. T=2.21 min, (M+H)$^+$ 358.20. Analytical HPLC: (Condition A): >99%, ret. T=13.26 min, (Condition B): >99%, ret. T=15.20 min, (Condition C): >96%, ret. T=4.08 min, (Condition D): >99%, ret. T=4.38 min.

Example 74

5-(1-(2,6-difluorophenyl)-1H-pyrazolo[3,4-b]pyridin-4-yl)pyrimidin-4-amine

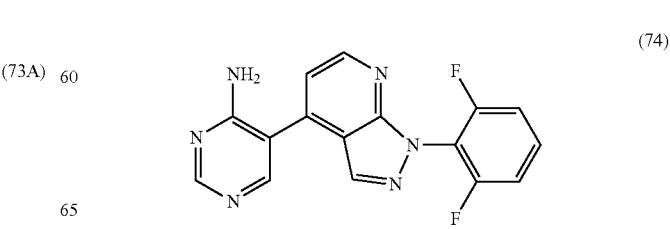

(74)

Intermediate 74A: 1-(2,6-difluorophenyl)-4-iodo-1H-pyrazolo[3,4-b]pyridine

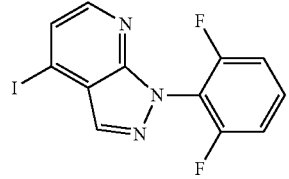
(74A)

To a dry 15 mL ChemGlass pressure bottle under $N_2$ was added (2,6-difluorophenyl)hydrazine (431 mg, 2.99 mmol), 2-fluoro-4-iodonicotinaldehyde (750 mg, 2.99 mmol) and anhydrous NMP (4.5 mL). The reaction mixture was flushed with argon, securely capped and heated to 185° C. for 1.5 h. The reaction mixture was worked up according to the general procedure described in Intermediate 69A to give 1.19 g (quantitative yield) of the title compound (contains approximately 50% of the hydrazone intermediate) as thick, dark oil. LC/MS (Condition B): ret. T=3.5 min, $(M+H)^+$ 357.91.

Intermediate 74B: 1-(2,6-difluorophenyl)-1H-pyrazolo[3,4-b]pyridin-4-ylboronic acid

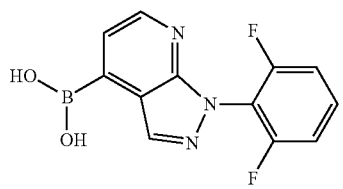
(74B)

To a 48 mL pressure bottle containing Intermediate 74A (1.19 g, 3.24 mmol) was added 4,4,4',4',5,5,5',5'-octamethyl-2,2'-bi(1,3,2-dioxaborolane) (1.35 g, 13.86 mmol), potassium acetate (1.36 g, 13.86 mmol), and anhydrous DMSO (12.5 mL). The reaction mixture was purged with argon and treated with $PdCl_2(dppf).CH_2Cl_2$ (56 mg, 0.077 mmol). The reaction mixture was heated to 85° C. for 1 h, then at 105° C. for 1 h to give conversion to the desired product. LC/MS (Condition B): ret. T=2.7 min, $(M+H)^+$ 276.01.

Example 74

Example 74 was prepared according to the general procedure in Example 1, except heating at 108° C. for 4.5 h, and using the following materials: Intermediate 74B (892 mg, 3.24 mmol), 5-bromopyrimidin-4-amine (790 mg, 4.54 mmol), sodium carbonate (1.37 g, 12.97 mmol), EtOH:DME:$H_2O$ (1.2:2.5:1.0 ratio) (12.5 mL), and tetrakis(triphenylphosphine) palladium(0) (187 mg, 0.162 mmol). Example 74 was isolated as a light tan solid (30.1 mg, 2.8%). Purification was done by preparative HPLC (Condition A) using a Phenomenex Luna Axia 30×100 mm S10 column from 15% Solvent B to 75% Solvent B over 11 min, ret. T=5.0 min. $^1H$ NMR (500 MHz, DMSO-$d_6$) δ ppm 8.63 (1 H, d, J=4.58 Hz), 8.51 (1 H, s), 8.43 (1 H, s), 8.31 (1 H, s), 7.68-7.81 (1 H, m), 7.41-7.51 (3 H, m), 7.01 (2 H, br. s.). LC/MS (Condition B): ret. T=1.86 min, $(M+H)^+$ 325.10. Analytical HPLC: (Condition A): >99%, ret. T=13.98 min, (Condition B): >99%, ret. T=15.96 min, (Condition C): >98%, ret. T=4.79 min, (Condition D): >99%, ret. T=5.17 min.

Example 75

5-(1-(3-chloro-5-fluorophenyl)-1H-pyrazolo[3,4-b]pyridin-4-yl)pyrimidin-4-amine

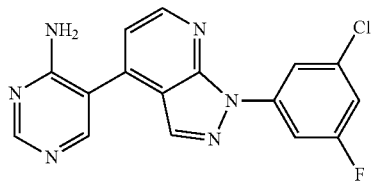
(75)

Intermediate 75A: 1-(3-chloro-5-fluorophenyl)-4-iodo-1H-pyrazolo[3,4-b]pyridine

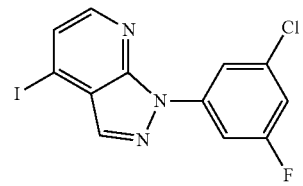
(75A)

To a dry 15 mL ChemGlass pressure bottle under $N_2$ was added 4-iodo-2-fluoro-3-formylpyridine (714.6 mg, 2.85 mmol), (3-chloro-5-fluorophenyl)hydrazine (457.6 mg, 2.85 mmol) and anhydrous NMP (8.5 mL). The reaction mixture was flushed with argon, securely capped and heated to 185° C. for 1 h, 45 min. The reaction mixture was worked up according to the procedure described in Intermediate 69A to give 839 mg (76.9%) of the title compound (contains approximately 45% of the hydrazone intermediate) as a dark red solid. LC/MS (Condition B): ret. T=4.8 min, $(M+H)^+$ 373.87.

Intermediate 75B: 1-(3-chloro-5-fluorophenyl)-1H-pyrazolo[3,4-b]pyridin-4-ylboronic acid

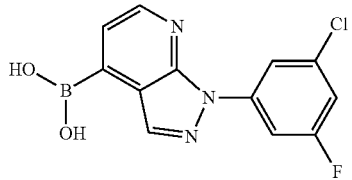
(75B)

To a 48 mL pressure bottle containing Intermediate 75A (558.6 mg, 1.46 mmol) was added 4,4,4',4',5,5,5',5'-octamethyl-2,2'-bi(1,3,2-dioxaborolane) (569.2 mg, 2.24 mmol), potassium acetate (584.3 mg, 5.95 mmol), and anhydrous DMSO (11 mL). The reaction mixture was flushed with argon and treated with $PdCl_2(dppf).CH_2Cl_2$ (59.1 mg, 0.081 mmol). The reaction mixture was heated to 85° C. for 1 h and then at 105° C. for 1.5 h to give conversion to the desired product. LC/MS (Condition B): ret. T=4.29 min, (M+H)+ 291.99, 292.99.

Example 75

Example 75 was prepared according to the general procedure in Example 1, except heating at 108° C. for 4.25 h, and using the following materials: Intermediate 75B (426 mg, 1.46 mmol), 5-bromopyrimidin-4-amine (379.5 mg, 2.18 mmol), sodium carbonate (636.7 mg, 6.01 mmol), EtOH:DME:H$_2$O (1.2:2.5:1.0 ratio) (10 mL) and tetrakis(triphenylphosphine)palladium(0) (83.5 mg, 0.072 mmol). Example 75 was isolated as a light tan solid (47.2 mg, 9.1%). Purification was done by preparative HPLC (Condition A) using a Phenomenex Luna Axia 30×100 mm S10 column from 33% Solvent B to 100% Solvent B over 11 min, ret. T=7.32 min. $^1$H NMR (500 MHz, METHANOL-d$_4$) δ ppm 8.80 (1 H, t, J=4.73 Hz), 8.53 (1 H, d, J=4.58 Hz), 8.46 (1 H, br. s.), 8.25-8.35 (3 H, m), 7.45 (1 H, t, J=4.88 Hz), 7.18 (1 H, d, J=8.24 Hz) LC/MS (Condition B): ret. T=3.00 min, (M+H)+ 341.00, 343.00. Analytical HPLC: (Condition A): >95%, ret. T=24.52 min, (Condition B): >95%, ret. T=24.09 min, (Condition C): >95%, ret. T=10.18 min, (Condition D): >97%, ret. T=10.74 min.

Example 76

5-(1-(2-(trifluoromethyl)phenyl)-1H-pyrazolo[3,4-b]pyridin-4-yl)pyrimidin-4-amine

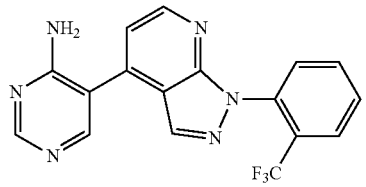

(76)

Intermediate 76A: 4-iodo-1-(2-(trifluoromethyl)phenyl)-1H-pyrazolo[3,4-b]pyridine

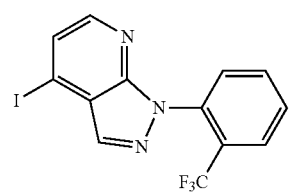

(76A)

To a dry 15 mL ChemGlass pressure bottle under N$_2$ was added 4-iodo-2-fluoro-3-formylpyridine (750 mg, 2.99 mmol), (2-(trifluoromethyl)phenyl)hydrazine (526 mg, 2.99 mmol), DMAP (200 mg, 1.637 mmol), and anhydrous NMP (4 mL). The reaction mixture was flushed with argon, securely capped and heated at 185° C. for 3.75 h. The reaction mixture was worked up according to the procedure described in Intermediate 69A to give 535 mg (44%) of the title compound (contains approximately 88% of the hydrazone intermediate) as a brown solid. LC/MS (Condition B): ret. T=4.19 min, (M+H)+ 389.90.

Intermediate 76B: 1-(2-(trifluoromethyl)phenyl)-1H-pyrazolo[3,4-b]pyridin-4-ylboronic acid

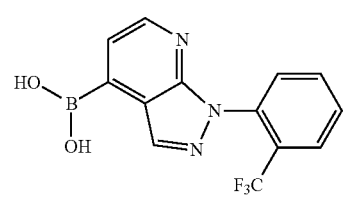

(76B)

To a 48 mL pressure bottle containing Intermediate 76A (535 mg, 1.32 mmol) was added 4,4,4',4',5,5,5',5'-octamethyl-2,2'-bi(1,3,2-dioxaborolane) (500 mg, 1.97 mmol), potassium acetate (520 mg, 5.30 mmol), and anhydrous DMSO (10 mL). The reaction mixture was flushed with argon, treated with PdCl$_2$(dppf).CH$_2$Cl$_2$ (60 mg, 0.082 mmol), and heated to 105° C. for 1.25 h to give the desired product.

Example 76

Example 76 was prepared according to the general procedure in Example 1, except heating at 105° C. for 4 h, and using the following materials: Intermediate 76B (350 mg, 1.14 mmol), 5-bromopyrimidin-4-amine (260 mg, 1.49 mmol), sodium carbonate (500 mg, 4.72 mmol), EtOH:DME:H$_2$O (1.2:2.5:1.0 ratio) (8 mL), and tetrakis(triphenylphosphine)palladium(0) (60 mg, 0.052 mmol). Example 76 was isolated as a tan solid (20.0 mg, 4.9%). Purification was done by preparative HPLC (Condition A) using a Phenomenex Luna Axia 30×100 mm S10 column from 15% Solvent B to 85% Solvent B over 11 min, ret. T=6.29 min. 500 MHz $^1$H NMR (500 MHz, MeOD) δ ppm 7.44 (d, J=4.88 Hz, 1 H) 7.65 (d, J=7.93 Hz, 1 H) 7.83 (t, J=7.63 Hz, 1 H) 7.90 (t, J=7.17 Hz, 1 H) 8.01 (d, J=7.63 Hz, 1 H) 8.33 (d, J=12.51 Hz, 2 H) 8.54 (s, 1 H) 8.62 (d, J=4.88 Hz, 1 H) LC/MS (Condition B): ret. T=2.13 min, (M+H)+ 357.10. Analytical HPLC: (Condition A): >99%, ret. T=15.98 min, (Condition B): >99%, ret. T=17.36 min, (Condition C): >97%, ret. T=6.19 min, (Condition D): >99%, ret. T=6.54 min.

Example 77

5-(1-(2,4,6-trifluorophenyl)-1H-pyrazolo[3,4-b]pyridin-4-yl)pyrimidin-4-amine

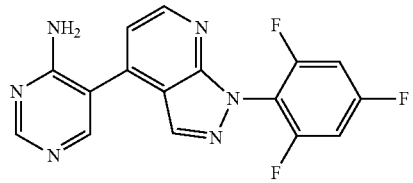

(77)

Intermediate 77A: 4-Iodo-1-(2,4,6-trifluorophenyl)-1H-pyrazolo[3,4-b]pyridine

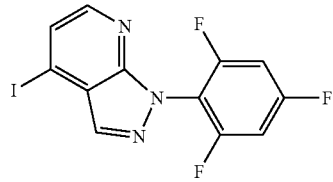

(77A)

To a 15 mL pressure bottle was added 2-fluoro-4-iodonicotinaldehyde (530 mg, 2.112 mmol), (2,4,6-trifluorophenyl)hydrazine (359 mg, 2.215 mmol), DMAP (53 mg, 0.434 mmol), and anhydrous NMP (4 mL). The reaction mixture was flushed with argon, securely capped, and heated to 185° C. for 1.75 h. The reaction mixture was worked up according to the procedure described in Intermediate 69A and the product was purified by Biotage Silica gel chromatography using a 40 g Thompson Single Step™ silica cartridge with a linear gradient from 100% hexanes to 100% $CH_2Cl_2$ over 14 column volumes to give 133 mg (16.8%) of the title compound as a yellow solid. LC/MS (Condition B): ret. T=3.7 min, $(M+H)^+$ 375.90 and 230 mg (27.6%) of the hydrazone intermediate as a pale yellow solid, LC/MS (Condition B): ret. T=3.7 min, $(M+H)^+$ 395.90.

Intermediate 77B: 1-(2,4,6-trifluorophenyl)-1H-pyrazolo[3,4-b]pyridin-4-ylboronic acid

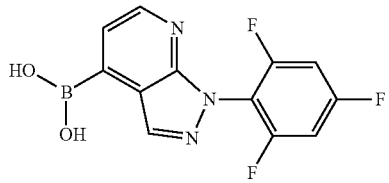

(77B)

To a 48 mL pressure bottle containing (E)-2-fluoro-4-iodo-3-((2-(2,4,6-trifluorophenyl)hydrazono)methyl)pyridine (230 mg, 0.582 mmol), were added Intermediate 77A (133 mg, 0.355 mmol), 4,4,4',4',5,5,5',5'-octamethyl-2,2'-bi(1,3,2-dioxaborolane) (330 mg, 1.30 mmol), potassium acetate (350 mg, 3.57 mmol), and anhydrous DMSO (8 mL). The reaction mixture was purged with argon, treated with $PdCl_2$(dppf).$CH_2Cl_2$(64 mg, 0.087 mmol), and heated to 85° C. for 1.25 h to give the desired intermediate. LC/MS (Condition B): ret. T=2.9 min, $(M+H)^+$ 294.03.

Example 77

Example 77 was prepared according to the general procedure in Example 1, except heating at 105° C. for 4 h, and using the following materials: Intermediate 77B (272 mg, 0.93 mmol), 5-bromopyrimidin-4-amine (240 mg, 1.38 mmol), sodium carbonate (400 mg, 3.77 mmol), EtOH:DME:$H_2O$ (1.2:2.5:1.0 ratio) (5 mL) and tetrakis(triphenylphosphine)palladium(0) (40 mg, 0.037 mmol). Example 77 was isolated as a white solid (36.2 mg, 11.3%). Purification was done by preparative HPLC (Condition A) using a Phenomenex Luna Axia 30×100 mm S10 column from 12% Solvent B to 85% Solvent B over 11 min, ret. T=6.16 min. $^1$H NMR (500 MHz, DMSO-$d_6$) δ ppm 8.66 (1 H, d, J=4.8 Hz), 8.57 (1 H, s), 8.46 (1 H, s), 8.35 (1 H, br. s.), 7.62 (2 H, t, J=8.70 Hz), 7.45 (1 H, d, J=4.6 Hz), 7.29 (2 H, br. s.) LC/MS (Condition B): ret. T=2.0 min, $(M+H)^+$ 343.06. Analytical HPLC: (Condition A): >96%, ret. T=15.38 min, (Condition B): >96%, ret. T=16.94 min, (Condition C): >98%, ret. T=5.63 min, (Condition D): >99%, ret. T=5.97 min.

Example 78

5-(1-(2-chloro-4-fluorophenyl)-1H-pyrazolo[3,4-b]pyridin-4-yl)pyrimidin-4-amine

(78)

Intermediate 78A: 1-(2-chloro-4-fluorophenyl)-4-iodo-1H-pyrazolo[3,4-b]pyridine

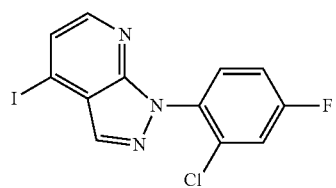

(78A)

To a dry 15 mL ChemGlass pressure bottle under $N_2$ was added 4-iodo-2-fluoro-3-formylpyridine (314 mg, 1.25 mmol), (2-chloro-4-fluorophenyl)hydrazine (210 mg, 1.31 mmol), and anhydrous NMP (5 mL). The reaction mixture was purged with argon, heated at 185° C. for 2 h, and then at 140° C. for 36 h. The reaction mixture was worked up according to the procedure described in Intermediate 69A and the crude product was purified by Biotage Silica gel chromatography using a 80 g Thompson Single Step™ silica cartridge with a linear gradient from 100% hexanes to 100% $CH_2Cl_2$ over 12 column volumes to give 63.5 mg (13.6%) of the title compound as a pale yellow solid, LC/MS (Condition B): ret. T=3.7 min, $(M+H)^+$ 373.88, 375.88 and 149.3 mg (30.3%) of the hydrazone intermediate as a pale yellow solid, LC/MS (Condition B): ret. T=4.2 min, $(M+H)^+$ 393.90, 395.90.

Intermediate 78B: 1-(2-chloro-4-fluorophenyl)-1H-pyrazolo[3,4-b]pyridin-4-ylboronic acid

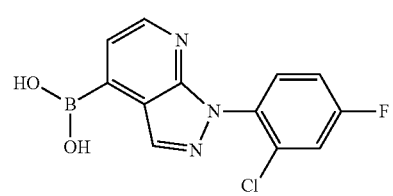

(78B)

To a 48 mL pressure bottle containing 1-(2-chloro-4-fluorophenyl)-4-iodo-1H-pyrazolo[3,4-b]pyridine (68.5 mg, 0.183 mmol) was added 4,4,4',4',5,5,5',5'-octamethyl-2,2'-bi (1,3,2-dioxaborolane) (81.7 mg, 0.322 mmol), potassium acetate (85.1 mg, 0.867 mmol), and anhydrous DMSO (1 mL). The reaction mixture was purged with argon, then treated with PdCl$_2$(dppf).CH$_2$Cl$_2$ (11.5 mg, 0.016 mmol). The reaction mixture was again purged with argon, securely capped, and heated to 85° C. for 1 h to give the desired intermediate. LC/MS (Condition B): ret. T=3.0 min, (M+H)$^+$ 292.01.

Example 78

Example 78 was prepared according to the general procedure in Example 1, except heating at 105° C. for 3 h, and using the following materials: Intermediate 78B (all material from above synthesis), 5-bromopyrimidin-4-amine (51.1 mg, 0.293 mmol), sodium carbonate (78 mg, 0.733 mmol), EtOH: DME:H$_2$O (1.2:2.5:1.0 ratio) (1 mL) and tetrakis(triphenylphosphine)palladium(0) (14.8 mg, 0.013 mmol). Example 78 was isolated as a white solid (7.4 mg, 11.5%). Purification was done by preparative HPLC (Condition A) using a Phenomenex Luna Axia 30×100 mm S10 column from 15% Solvent B to 85% Solvent B over 12 min, ret. T=6.64 min. $^1$H NMR (500 MHz, DMSO-d$_6$) δ ppm 9.23 (1 H, s), 8.86 (1 H, s), 8.72 (1 H, d, J=4.58 Hz), 8.46 (1 H, s), 7.84 (1 H, td, J=8.70, 6.10 Hz), 7.58-7.74 (1 H, m), 7.49 (1 H, d, J=4.58 Hz), 7.26-7.43 (1 H, m), 2.49 (2 H, s) LC/MS (Condition B): ret. T=2.5 min, (M+H)$^+$ 341.13, 343.13. Analytical HPLC: (Condition A): >97%, ret. T=16.23 min, (Condition B): >97%, ret. T=17.57 min, (Condition C): >96%, ret. T=5.64 min, (Condition D): >96%, ret. T=5.98 min.

Example 79

3-(4-(4-aminopyridin-3-yl)-1H-pyrazolo[3,4-b]pyridin-1-yl)benzenesulfonamide

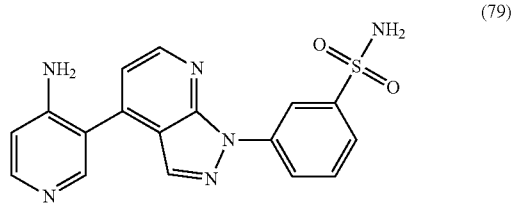 [SMILES: Nc1ccncc1-c1ccnc2c1cnn2-c1cccc(S(N)(=O)=O)c1]

(79)

Example 79 was prepared according to the general procedure in Example 2, except heating at 105° C. for 2.25 h, and using the following materials: Intermediate 1A (50 mg, 0.084 mmol), 4-aminopyridin-3-ylboronic acid (81 mg, 0.59 mmol), sodium carbonate (31 mg, 0.292 mmol), EtOH:DME: H$_2$O (1.2:2.5:1.0 ratio) (1.5 mL) and tetrakis(triphenylphosphine)palladium(0) (9.65 mg, 8.35 μmol). Example 79 was isolated as a yellow solid (10.2 mg, 32.3%). Purification was done by preparative HPLC (Condition A) using a Phenomenex Luna Axia 30×100 mm S10 column from 5% Solvent B to 85% Solvent B over 12 min, ret. T=5.7 min. $^1$H NMR (500 MHz, METHANOL-d$_4$) δ ppm 8.93-9.00 (1 H, m), 8.71-8.79 (1 H, m), 8.60-8.67 (1 H, m), 8.22-8.27 (1 H, m), 8.18 (1 H, s), 8.09-8.14 (1 H, m), 7.84-7.93 (1 H, m), 7.69-7.80 (1 H, m), 7.37-7.47 (1 H, m), 6.79-6.92 (1 H, m) LC/MS (Condition B): ret. T=1.75 min, (M+H)$^+$ 366.98. Analytical HPLC: (Condition A): >97%, ret. T=13.51 min, (Condition B): >97%, ret. T=15.81 min, (Condition C): >99%, ret. T=4.54 min, (Condition D): >97%, ret. T=4.87 min.

Example 80

3-(4-(4-methylpyridin-3-yl)-1H-pyrazolo[3,4-b]pyridin-1-yl)benzenesulfonamide

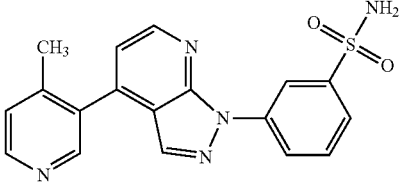

(80)

Example 80 was prepared according to the general procedure in Example 2, except heating at 105° C. for 4 h followed by heating at 115° C. for 5.25 h, and using the following materials: Intermediate 1A (32.8 mg, 0.189 mmol), potassium carbonate (149.6 mg, 1.08 mmol), 4-methylpyrimidin-5-ylboronic acid hydrochloride salt (62.8 mg, 0.362 mmol), NMP (1.1 mL), deoxygenated water (100 μL), and PdCl$_2$ (dppf).CH$_2$Cl$_2$ (29.7 mg, 0.036 mmol). Example 80 was isolated as an off white solid (16.5 mg, 24.6%). Purification was done by preparative HPLC (Condition A) using a Phenomenex Luna Axia 30×100 mm S10 column from 5% Solvent B to 85% Solvent B over 12 min, ret. T=7.04 min, followed by purification by preparative HPLC (Condition B) using a Phenomenex Luna 30×100 mm S10 column from 15% Solvent B to 100% Solvent B over 12 min, ret. T=7.06 min. $^1$H NMR (500 MHz, METHANOL-d$_4$) δ ppm 8.97-9.02 (1 H, m), 8.80 (1 H, d, J=4.58 Hz), 8.68 (1 H, ddd, J=8.09, 2.14, 1.07 Hz), 8.53-8.61 (2 H, m), 8.17 (1 H, s), 7.87-7.95 (1 H, m), 7.76 (1 H, t, J=7.93 Hz), 7.55 (1 H, d, J=5.19 Hz), 7.38 (1 H, d, J=4.58 Hz), 2.37 (3 H, s) LC/MS (Condition B): ret. T=2.20 min, (M+H)$^+$ 366.01. Analytical HPLC: (Condition A): >98%, ret. T=18.43 min, (Condition B): >98%, ret. T=16.85 min, (Condition C): >97%, ret. T=5.64 min, (Condition D): >98%, ret. T=5.92 min.

Example 81

1-(3-fluorophenyl)-4-(4-methylpyridin-3-yl)-1H-pyrazolo[3,4-b]pyridine

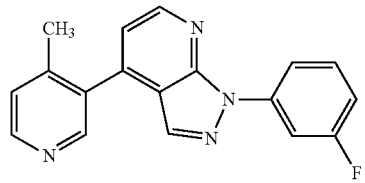

(81)

Example 81 was prepared according to the general procedure outlined for Examples 14-60 in Table 1 and was isolated as a dark solid (10.6 mg, 21.2%). Purification was done by preparative HPLC (Condition A) using a Phenomenex Luna Axia 30×100 mm S10 column from 25% Solvent B to 100% Solvent B over 12 min, ret. T=8.20 min. $^1$H NMR (500 MHz, METHANOL-d$_4$) δ ppm 8.71-8.82 (1 H, m), 8.49-8.61 (2 H, m), 8.18-8.29 (2 H, m), 8.08-8.15 (1 H, m), 7.49-7.64 (2 H, m), 7.29-7.40 (1 H, m), 7.04-7.18 (1 H, m), 2.35 (3 H, s). LC/MS (Condition B): ret. T=2.89 min, (M+H)$^+$ 305.08. Analytical HPLC: (Condition A): >97%, ret. T=24.58 min, (Condition B): >96%, ret. T=24.00 min, (Condition C): >98%, ret. T=10.41 min, (Condition D): >94%, ret. T=10.71 min.

Example 82

1-(2-chloro-4-fluorophenyl)-4-(4-methylpyridin-3-yl)-1H-pyrazolo[3,4-b]pyridine

(82)

Example 82 was prepared according to the general procedure outlined for Examples 14-60 in Table 1. LC/MS*ret. time=3.09 min, (M+H)$^+$ 339.09.

Example 83

2-(4-(4-methylpyridin-3-yl)-1H-pyrazolo[3,4-b]pyridin-1-yl)ethanol

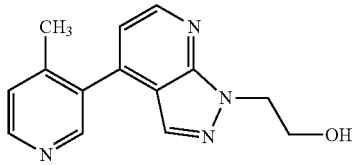
(83)

Example 83 was prepared according to the general procedure outlined for Examples 14-60 in Table 1 and isolated as a tan solid (8.2 mg, 14.7%). Purification was done by preparative HPLC (Condition A) using a Phenomenex Luna Axia 30×100 mm S10 column from 0% Solvent B to 65% Solvent B over 12 min, ret. T=5.08 min. $^1$H NMR (500 MHz, METHANOL-d$_4$) δ ppm 8.66 (1 H, d, J=4.58 Hz), 8.54 (1 H, d, J=4.88 Hz), 8.50 (1 H, s), 7.92 (1 H, s), 7.52 (1 H, d, J=5.19 Hz), 7.23 (1 H, d, J=4.58 Hz), 4.70 (2 H, t, J=5.65 Hz), 4.08 (2 H, t, J=5.65 Hz), 2.33 (3 H, s) LC/MS (Condition B): ret. T=1.29 min, (M+H)$^+$ 255.16. Analytical HPLC: (Condition A): >99%, ret. T=11.18 min, (Condition B): >99%, ret. T=11.58 min, (Condition C): >96%, ret. T=2.44 min, (Condition D): >98%, ret. T=2.55 min.

Example 84

4-(4-methylpyridin-3-yl)-1-(2,2,2-trifluoroethyl)-1H-pyrazolo[3,4-b]pyridine

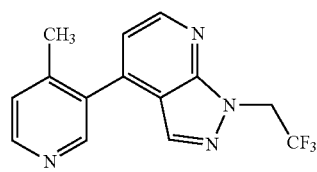
(84)

Example 84 was prepared according to the general procedure outlined for Examples 14-60 in Table 1 and isolated as an amber glassy solid (23.8 mg, 40.3%). Purification was done by preparative HPLC (Condition A) using a Phenomenex Luna Axia 30×100 mm S10 column from 10% Solvent B to 80% Solvent B over 12 min, ret. T=6.69 min. $^1$H NMR (500 MHz, CCl$_3$D) δ ppm 2.40 (s, 3 H), 5.18 (d, J=8.24 Hz, 2 H), 7.14 (d, J=4.58 Hz, 1 H), 7.58 (d, J=5.19 Hz, 1 H), 7.89 (s, 1 H), 8.62 (s, 1 H), 8.69 (dd, J=16.17, 4.88 Hz, 2 H). LC/MS (Condition A): ret. T=1.22 min, (M+H)$^+$ 293.08. Analytical HPLC: (Condition A): >99%, ret. T=16.66 min, (Condition B): >99%, ret. T=16.45 min, (Condition C): >98%, ret. T=6.57 min, (Condition D): >98%, ret. T=6.57 min.

Example 85

4-(4-methylpyridin-3-yl)-1-phenyl-1H-pyrazolo[3,4-b]pyridine

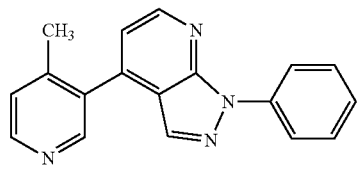
(85)

Example 85 was prepared according to the general procedure outlined for Examples 14-60 in Table 1 and isolated as a tan film (21.6 mg, 80%). Purification was done by preparative HPLC (Condition A) using a Phenomenex Luna Axia 30×100 mm S10 column from 15% Solvent B to 100% Solvent B over 12 min, ret. T=8.00 min. $^1$H NMR (500 MHz, METHANOL-d$_4$) δ ppm 8.72-8.77 (1 H, m), 8.52-8.61 (2 H, m), 8.28 (2 H, d, J=7.63 Hz), 8.06-8.15 (1 H, m), 7.51-7.62 (3 H, m), 7.36-7.45 (1 H, m), 7.28-7.36 (1 H, m), 2.37 (3 H, s). LC/MS (Condition A): ret. T=1.71 min, (M+H)$^+$ 287.11. Analytical HPLC: (Condition A): >99%, ret. T=21.76 min, (Condition B): >99%, ret. T=20.74 min, (Condition C): >98%, ret. T=9.41 min, (Condition D): >98%, ret. T=9.59 min.

Examples 86-88

Examples 86-88 shown below in Table 2 were prepared using the same general procedure as outlined for Examples 14-60 in Table 1, with the following exceptions:
Purifications were done using a Shimadzu preparative HPLC system using a gradient of Solvent A (10% MeOH/90% water/0.1% TFA) and Solvent B (90% MeOH/10% water/0.1% TFA), monitoring at a wavelength of 254 nM, with flow rate=36 mL/min and; LC/MS analysis, including retention times, was done using LC/MS (Condition B) as described above.

TABLE 2

| Ex. | R | Compound Name | LC/MS ret. T (min.) | [M + H]$^+$ |
|---|---|---|---|---|
| 86 | ![pyridyl-CH3] | 1-(5-methylpyridin-2-yl)-4-(4-methylpyridin-3-yl)-1H-pyrazolo[3,4-b]pyridine | 2.32 | 302.10 |

TABLE 2-continued

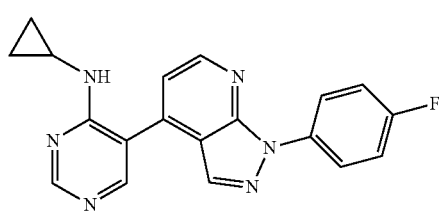

| Ex. | R | Compound Name | LC/MS ret. T (min.) | [M + H]+ |
|---|---|---|---|---|
| 87 | ![thiazole] | 2-(4-(4-methylpyridin-3-yl)-1H-pyrazolo[3,4-b]pyridin-1-yl) thiazole | 2.42 | 294.15 |
| 88 | ![methylthiazole] | 4-methyl-2-(4-(4-methylpyridin-3-yl)-1H-pyrazolo[3,4-b]pyridin-1-yl) thiazole | 2.44 | 308.03 |

Example 89

N-cyclopropyl-5-(1-(4-fluorophenyl)-1H-pyrazolo[3,4-b]pyridin-4-yl)pyrimidin-4-amine

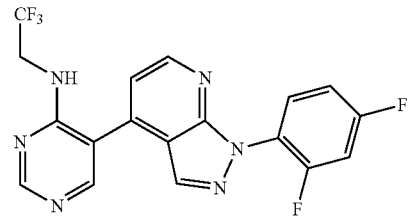

(89)

A vial was charged with tetrakis(triphenylphosphine)palladium(0) (5.78 mg, 5.00 mmol), Intermediate 5A (25.7 mg, 0.100 mmol), sodium carbonate (42.4 mg, 0.400 mmol), and Intermediate 108A. The mixture was stirred at room temperature for 10 min under N₂, then DME (Ratio: 2.0, Volume: 373 μl), EtOH (Ratio: 1.000, Volume: 187 μl), and water (Ratio: 1.000, Volume: 187 μl) were added sequentially. The resultant mixture was heated at 90° C. overnight. After 13 h, the reaction mixture was allowed to cool to room temperature, then quenched with water and diluted with EtOAc. The layers were separated and the aqueous phase was extracted with EtOAc (3×10 ml). The organic phases were combined, dried over Na₂SO₄, filtered, and concentrated to afford a yellow residue. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 20 mL/min. Fractions containing the Example 89 were combined and dried via centrifugal evaporation to give 19 mg (53%) of the title compound. LC/MS (condition D): purity=99%, ret time=2.197 min, MS (ES): m/z=347.1 [M+H]+.

Example 90

5-(1-(2,4-difluorophenyl)-1H-pyrazolo[3,4-b]pyridin-4-yl)-N-(2,2,2-trifluoroethyl) pyrimidin-4-amine

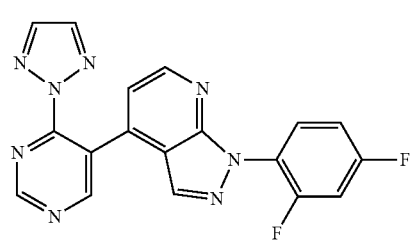

(90)

A vial was charged with tetrakis(triphenylphosphine)palladium(0) (5.78 mg, 5.00 μmol), Intermediate 63A (27.5 mg, 0.1 mmol), sodium carbonate (42.4 mg, 0.400 mmol), and Intermediate 107A (30.3 mg, 0.100 mmol). The mixture was stirred at room temperature for 10 min under N₂, then DME (Ratio: 2.0, Volume: 373 μl), EtOH (Ratio: 1.000, Volume: 187 μl), and water (Ratio: 1.000, Volume: 187 μl) were added sequentially. The resultant mixture was heated at 90° C. overnight. After 17 h, the reaction mixture was allowed to cool to room temperature, then quenched with water and diluted with EtOAc. The layers were separated and the aqueous phase was extracted with EtOAc (3×10 ml). The organic phases were combined, dried over Na₂SO₄, filtered, and concentrated to afford a brown residue. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 20 mL/min. Fractions containing Example 90 were combined and dried via centrifugal evaporation to give 5.4 mg (12%) of the title compound. LC/MS (condition D): purity=94%, ret time=1.77 min, MS (ES): m/z=407.1 [M+H]+.

Example 91

4-(4-(2 H-1,2,3-triazol-2-yl)pyrimidin-5-yl)-1-(2,4-difluorophenyl)-1H-pyrazolo[3,4-b]pyridine (91)

Intermediate 91A: 5-iodo-4-(2 H-1,2,3-triazol-2-yl)pyrimidine

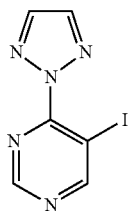

(91A)

To a solution of 1H-1,2,3-triazole (63.2 mg, 0.915 mmol) in THF (2.4 mL), was added, portionwise, at 0° C., NaH (39.9 mg, 0.998 mmol). After 30 minutes of stirring, 4-chloro-5-iodopyrimidine (200 mg, 0.832 mmol) was added and the reaction mixture was allowed to come to room temperature, and stirred until judged complete by LCMS. To this was added aqueous saturated NH$_4$Cl, and the mixture was allowed to stir for 5 min at which time it was determined that the reaction was complete by LC-MS analysis. This reaction mixture was diluted with ethyl acetate and extracted twice. The combined organics were washed with brine and dried over Na$_2$SO$_4$, filtered and concentrated in vacuo. The crude material was dissolved in a minimal amount of hexanes and loaded onto a silica gel column, the column was subsequently eluted as a gradient from 0-15% EtOAc/hexanes. The desired isomer was thus separated from the regioisomeric triazole adduct. The white solid attained (90 mg, 39.6%) was determined to be the desired material by $^1$HNMR and LC/MS. MS (ES): m/z=274.0 [M+H]$^+$. $^1$H NMR (400 MHz, CCl$_3$D) δ ppm 9.34 (1 H, s), 9.15 (1 H, s), 8.03 (2 H, s).

Example 91

Example 91 was prepared according to the procedure described for Example 2 using Intermediates 63A and 91A. The crude material was purified via preparative HPLC (Column: Waters XBridge C18, 19×250 mm, 5-μm particles; Guard Column: Waters XBridge C18, 19×10 mm, 5-μm particles; Mobile Phase A: 5:95 methanol:water with 10-mM ammonium acetate; Mobile Phase B: 95:5 methanol:water with 10-mM ammonium acetate; Gradient: 15-100% B over 25 minutes, then a 5-minute hold at 100% B; Flow: 20 mL/min. The collected fractions were combined and dried via centrifugal evaporation to yield the title compound (1.0 mg, 2.6%). LC/MS (conditions D): ret time=1.825 min, MS (ES): m/z=376.97 [M+H]$^+$. $^1$H NMR (400 MHz, MeOD) δ ppm 9.35 (1 H, s), 9.08 (1 H, s), 8.63 (1 H, d, J=4.62 Hz), 7.79-7.84 (2 H, m), 7.72 (1 H, s), 7.59-7.68 (1 H, m), 7.27 (1 H, d, J=4.62 Hz), 7.07-7.20 (2 H, m).

Example 92

5-(3-chloro-1-(4-fluorophenyl)-1H-pyrazolo[3,4-b]pyridin-4-yl)pyrimidin-4-amine

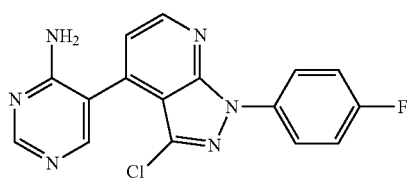

(92)

Intermediate 92A: 3-Chloro-1-(4-fluorophenyl)-4-iodo-1H-pyrazolo[3,4-b]pyridine

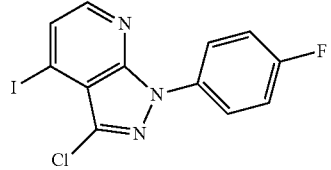

(92A)

To a solution of Intermediate 2A (33.9 mg, 0.1 mmol) in DMF (Volume: 1 mL) under argon at room temp was added N-chlorosuccinimide (107 mg, 0.800 mmol). The reaction mixture was allowed to stir overnight. The reaction mixture was diluted with ethyl acetate and washed (2×15 mL) with 10% LiCl, once with brine, dried over Na$_2$SO$_4$, filtered and concentrated. The crude product was dissolved in a small amount of dichloromethane and charged to a 4 g silica gel cartridge which was eluted with a 20 min gradient from 0% to 100% of ethyl acetate in dichloromethane. The resulting brown solid (23 mg, 61.6%) was determined to be the desired material by $^1$HNMR and LCMS. MS (ES): m/z=274.0 [M+H]$^+$. $^1$H NMR (400 MHz, CCl$_3$D) δ ppm 8.58-8.60 (1 H, m), 8.24 (1 H, s), 8.14-8.20 (2 H, m), 7.18-7.26 (2 H, m).

Intermediate 92B: Methyl hydrogen 3-chloro-1-(4-fluorophenyl)-1H-pyrazolo[3,4-b]pyridin-4-ylboronate

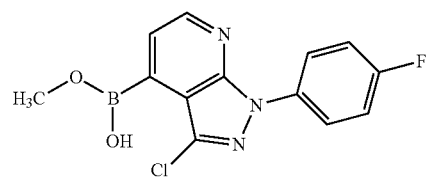

(92B)

To a scintillation vial with a Teflon screw cap was added Intermediate 92A (0.023 g, 0.062 mmol), potassium acetate (0.026 g, 0.270 mmol), and 4,4,4',4',5,5,5',5'-octamethyl-2,2'-bi(1,3,2-dioxaborolane) (0.030 g, 0.117 mmol). The mixture was dissolved in DMSO (1 mL) and then purged with argon followed by degassing three times. To this was added PdCl$_2$(dppf).CH$_2$Cl$_2$ (5.03 mg, 6.16 mmol) and the mixture was again purged with argon. The sealed system was heated to 90° C. for 75 min. Observed MS was that of the monomethoxy boronic hemiacetal.

Example 92

Example 92 was prepared according to the procedure described for Example 2 using 5-bromopyrimidin-4-amine and Intermediate 92B. Example 92 was purified according the procedure described for Example 91. The collected fractions were evaporated to yield the title compound (3.3 mg, 15.73%). LC/MS (condition D): ret time=1.960 min, MS (ES): m/z=341.1 [M+H]$^+$. $^1$H NMR (400 MHz, DMSO-d$_6$) δ ppm 8.82 (1 H, d, J=4.62 Hz), 8.63 (1 H, s), 8.23-8.26 (1 H, m), 8.18-8.23 (2 H, m), 7.95 (1 H, s), 7.43-7.50 (2 H, m), 7.40 (1 H, d, J=4.62 Hz).

Example 93

1-(2,4-difluorophenyl)-4-(4-(trifluoromethyl)pyrimidin-5-yl)-1H-pyrazolo[3,4-b]pyridine

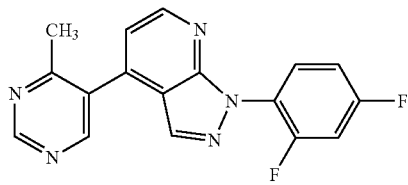

(93)

Example 93 was prepared according to the procedure described for Example 2 using Intermediates 63A and 5-bromo-4-(trifluoromethyl)pyrimidine. Example 93 was purified according the procedure described for Example 91. The collected fractions were evaporated to yield the title compound (15.3 mg, 40.1%). MS (ES): m/z=378.2 [M+H]+. $^1$H NMR (400 MHz, MeOD) δ ppm 9.50 (1 H, s), 9.08 (1 H, s), 8.68 (1 H, d, J=4.84 Hz), 8.10 (1 H, s), 7.70 (1 H, td, J=8.36, 5.72 Hz), 7.61 (1 H, s), 7.30 (1 H, d, J=4.62 Hz), 7.10-7.23 (2 H, m). Retention time using column conditions H was 1.25 min.

Intermediates 94A-98A

Intermediates 94A-98A were prepared and purified by the general procedure described for the preparation of Intermediate 2A using the appropriate commercially available hydrazine or hydrazine HCl salt.

TABLE 3

| Int. No. | Structure | Name | [M + H]+ observed |
|---|---|---|---|
| 94A | 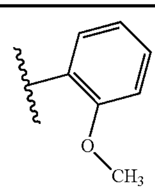 | 4-iodo-1-(2-methoxyphenyl)-1H-pyrazolo[3,4-b]pyridine | 352.0 |
| 95A | 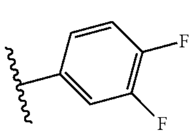 [SMILES: *c1ccc(F)c(F)c1] | 1-(3,4-difluorophenyl)-4-iodo-1H-pyrazolo[3,4-b]pyridine | 358.0 |

TABLE 3-continued

| Int. No. | Structure | Name | [M + H]+ observed |
|---|---|---|---|
| 96A | 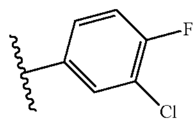 [SMILES: *c1ccc(F)c(Cl)c1] | 1-(3-chloro-4-fluorophenyl)-4-iodo-1H-pyrazolo[3,4-b]pyridine | 374.0 |
| 97A | 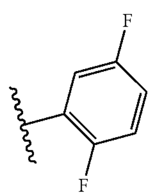 [SMILES: *c1cc(F)ccc1F] | 1-(2,5-difluorophenyl)-4-iodo-1H-pyrazolo[3,4-b]pyridine | 358.0 |
| 98A | 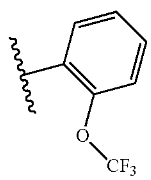 [SMILES: *c1ccccc1OC(F)(F)F] | 4-iodo-1-(2-(trifluoromethoxy)phenyl)-1H-pyrazolo[3,4-b]pyridine | 405.8 |

Intermediates 94B-97B

Intermediates 94B-97B were prepared by the general procedure described for the preparation of Intermediate 5A from Intermediate 2A, using Intermediates 94A-97A.

TABLE 4

| Int. No. | Structure | Name | [M + H]+ observed |
|---|---|---|---|
| 94B | 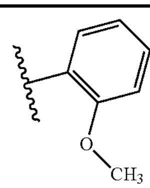 | methyl hydrogen 1-(2-methoxyphenyl)-1H-pyrazolo[3,4-b]pyridin-4-ylboronate | 284.14 |
| 95B | 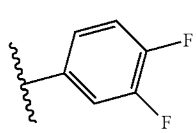 | methyl hydrogen 1-(3,4-difluorophenyl)-1H-pyrazolo[3,4-b]pyridin-4-ylboronate | 290.1 |
| 96B | 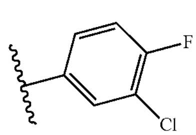 | methyl hydrogen 1-(3-chloro-4-fluorophenyl)-1H-pyrazolo[3,4-b]pyridin-4-ylboronate | 306.4 |

TABLE 4-continued

[structure: methyl boronate-substituted pyrazolo[3,4-b]pyridine with H3C-O-B(OH)- group and N-R]

| Int. No. | Structure | Name | [M + H]+ observed |
|---|---|---|---|
| 97B | 2,5-difluorophenyl | methyl hydrogen 1-(2,5-difluorophenyl)-1H-pyrazolo[3,4-b]pyridin-4-ylboronate | 290.13 |

Examples 94-98

Examples 94-97 were prepared according to the general procedure described for the preparation of Example 2 using Intermediates 94B to 97B and 5-bromopyrimidin-4-amine. Example 98 was prepared according to the general procedure described for the coupling of Intermediate 98A and Intermediate 62A. Examples 94-98 were purified by the general procedure described in Example 91.

TABLE 5

[structure: 4-amino-pyrimidine linked to pyrazolo[3,4-b]pyridine with N-R]

| Ex. | R | Name | [M + H]+ observed | Retention time |
|---|---|---|---|---|
| 94 | 2-methoxyphenyl | 5-(1-(2-methoxyphenyl)-1H-pyrazolo[3,4-b]pyridin-4-yl)-4-pyrimidinamine | 319.09 | 1.695 D |
| 95 | 3,4-difluorophenyl | 5-(1-(3,4-difluorophenyl)-1H-pyrazolo[3,4-b]pyridin-4-yl)-4-pyrimidinamine | 325.2 | 1.49 C |
| 96 | 3-chloro-4-fluorophenyl | 5-(1-(3-chloro-4-fluorophenyl)-1H-pyrazolo[3,4-b]pyridin-4-yl)-4-pyrimidinamine | 340.98 | 2.32 D |

TABLE 5-continued

| Ex. | R | Name | [M + H]+ observed | Retention time |
|---|---|---|---|---|
| 97 | 2,5-difluorophenyl | 5-(1-(2,5-difluorophenyl)-1H-pyrazolo[3,4-b]pyridin-4-yl)-4-pyrimidinamine | 325.2 | 1.11C |
| 98 | 2-(trifluoromethoxy)phenyl | 5-(1-(2-(trifluoromethoxy)phenyl)-1H-pyrazolo[3,4-b]pyridin-4-yl)-4-pyrimidinamine | 373.2 | 1.32C |

Examples 99-101

Example 99-101 were prepared according to the general procedure described for the preparation of Example 2 using Intermediates 5A, 95B, and 97, and 5-bromo-4-(trifluoromethyl)pyrimidine. Examples 99-101 were purified by the general procedure described in Example 91

TABLE 6

[structure: 4-trifluoromethyl-pyrimidine linked to pyrazolo[3,4-b]pyridine with N-R]

| Ex. | R | Name | [M + H]+ observed | Retention time |
|---|---|---|---|---|
| 99 | 4-fluorophenyl | 1-(4-fluorophenyl)-4-(4-(trifluoromethyl)-5-pyrimidinyl)-1H-pyrazolo[3,4-b]pyridine | 360.2 | 1.95F |
| 100 | 3,4-difluorophenyl | 1-(3,4-difluorophenyl)-4-(4-(trifluoromethyl)-5-pyrimidinyl)-1H-pyrazolo[3,4-b]pyridine | 378.2 | 2.09F |

TABLE 6-continued

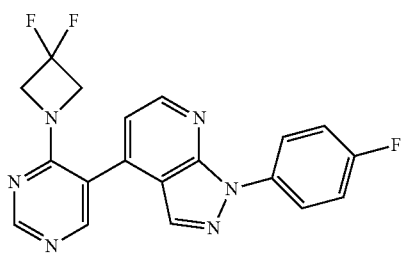

| Ex. | R | Name | [M + H]+ observed | Retention time |
|---|---|---|---|---|
| 101 | (structure: 2,5-difluorophenyl) | 1-(2,5-difluorophenyl)-4-(4-(trifluoromethyl)-5-pyrimidinyl)-1H-pyrazolo[3,4-b]pyridine | 378.2 | 1.73F |

Example 102

4-(4-(3,3-difluoroazetidin-1-yl)pyrimidin-5-yl)-1-(4-fluorophenyl)-1H-pyrazolo[3,4-b]pyridine (102)

Intermediate 102A:
4-(3,3-difluoroazetidin-1-yl)-5-iodopyrimidine

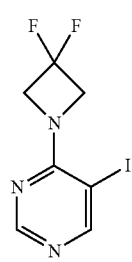

(102A)

To a suspension of sodium hydride (0.062 g, 1.560 mmol) in THF (Volume: 10 mL) was added 3,3-difluoroazetidine (0.097 g, 1.040 mmol) resulting in vigorous gas evolution. After 15 minutes at room temperature, 4-chloro-5-iodopyrimidine (0.25 g, 1.040 mmol) was added as a solution in THF. After 1 h at room temperature, the reaction appeared to have proceeded only about 10%. Next, 5 mL of DMF was added and the reaction mixture was stirred at room temperature overnight. Water was carefully added to quench the reaction, followed by the addition of EtOAc. The mixture was washed once with water and then twice with brine. Next, the mixture was dried over $MgSO_4$, filtered and concentrated to afford a brown solid. The crude material was purified by flash chromatography on silica using an ISCO machine (12 g column, 40 mL/min, 0-8% MeOH in $CH_2Cl_2$ over 15 minutes) to give Intermediate 102A (0.125 g, 0.417 mmol, 40.1% yield) as a tan solid.

Example 102

To a solution of Intermediate 5A (0.034 g, 0.1 mmol) and Intermediate 102A (0.045 g, 0.150 mmol) in a mixture of DME (1 mL), ethanol (0.5 mL) and water (0.5 mL) was added $Na_2CO_3$ (0.042 g, 0.400 mmol). The suspension was degassed with a stream of $N_2$ for 10 minutes and then tetrakis(triphenylphosphine)palladium(0) (5.78 mg, 5.00 µmol) was added followed by degassing for 10 minutes. The tube was sealed and heated at 90° C. for 14 hours. The reaction mixture was cooled to room temperature and diluted with MeOH. The contents of the tube were filtered, rinsed with MeOH, and concentrated to afford a brown solid. The crude material was purified via preparative LC/MS with the following conditions: Column: Waters XBridge C18, 19×250 mm, 5-µm particles; Guard Column: Waters XBridge C18, 19×10 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 35-75% B over 25 minutes, then a 15-minute hold at 75% B; Flow: 20 mL/min. Fractions containing the desired product were combined and dried via centrifugal evaporation. The material was further purified via preparative LC/MS with the following conditions: Column: Waters XBridge C18, 19×250 mm, 5-µm particles; Guard Column: Waters XBridge C18, 19×10 mm, 5-µm particles; Mobile Phase A: 5:95 acetonitrile:water with 0.05% TFA; Mobile Phase B: 95:5 acetonitrile:water with 0.05% TFA; Gradient: 5-40% B over 25 minutes, then a 15-minute hold at 40% B; Flow: 20 mL/min. Fractions containing the desired product were combined and dried via centrifugal evaporation. The yield of Example 103 was 12.4 mg, and its purity was 98%. LC/MS (condition C): ret time=1.50 min, MS (ES): m/z=383.1 $[M+H]^+$.

Example 103

4-(4-(3,3-difluoroazetidin-1-yl)pyrimidin-5-yl)-1-(2,4-difluorophenyl)-1H-pyrazolo[3,4-b]pyridine

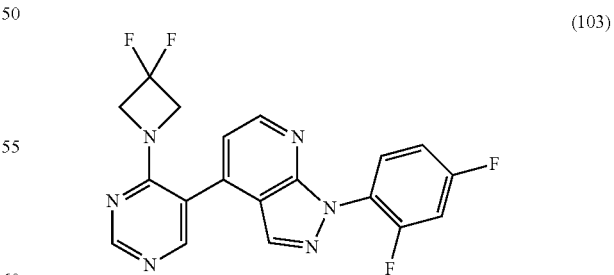

(103)

To a solution of Intermediate 63A (35.7 mg, 0.1 mmol) and Intermediate 102A (44.6 mg, 0.150 mmol) in a mixture of DME (1 mL), ethanol (0.5 mL) and water (0.5 mL) was added $Na_2CO_3$ (0.042 g, 0.400 mmol). This suspension was degassed with a stream of $N_2$ for 10 minutes and then tetrakis(triphenylphosphine)palladium(0) (5.78 mg, 5.00 mmol) was added followed by degassing for 10 minutes. The tube was then sealed, heated at 90° C. for 14 hours, and cooled to room temperature. The contents of the tube were diluted with MeOH, filtered, rinsed with MeOH, and concentrated to a brown sludge. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammonium acetate; Mobile Phase B: 95:5 acetonitrile:water with 10-mM ammonium acetate; Gradient: 15-100% B over 25 minutes, then a 5-minute hold at 100% B; Flow: 20 mL/min. Fractions containing the desired product were combined and dried via centrifugal evaporation. The yield of Example 103 was 6.0 mg, and its purity was approximately 100%. LC/MS (condition C): ret time=1.52 min, MS (ES): m/z=401.01 [M+H]$^+$.

Example 104

5-(1-(4-fluoro-2-(trifluoromethyl)phenyl)-1H-pyrazolo[3,4-b]pyridin-4-yl)pyrimidin-4-amine

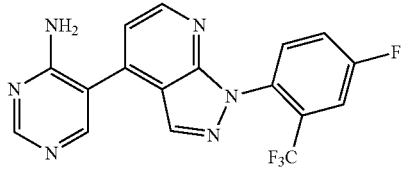

(104)

Intermediate 104A: 1-(4-fluoro-2-(trifluoromethyl)phenyl)-4-iodo-1H-pyrazolo[3,4-b]pyridine

(104A)

1-(4-fluoro-2-(trifluoromethyl)phenyl)-4-iodo-1H-pyrazolo[3,4-b]pyridine (0.20 g, 1.03 mmol) and 2-fluoro-4-iodonicotinaldehyde (0.284 g, 1.13 mmol) were dissolved in N-methylpyrrolidinone (3 mL) and heated at 185° C. for 3 hours. After cooling to room temperature, the mixture was then diluted with EtOAc (100 mL) and washed once with water (20 mL) and once with brine (20 mL). The organics were then dried over anhydrous magnesium sulfate, filtered and concentrated to give a brown solid. The crude material was purified by flash chromatography on silica using an ISCO system (12 g column, 40 mL/min, 0-25% ethyl acetate in hexanes over 20 minutes, rt=13 minutes) to give Intermediate 104A (0.050 g, 0.122 mmol, 11.80% yield) as a white solid. $^1$H NMR (500 MHz, CDCl$_3$) δ ppm 7.47 (dt, J=3, 8.1 Hz, 1 H); 7.58-7.65 (m, 2 H); 7.67 (d, J=4.8 Hz, 1 H); 8.14 (s, 1 H); 8.17 (d, J=5.1 Hz, 1 H).

Example 104

To a suspension of potassium acetate (0.060 g, 0.614 mmol) in DMSO (1 mL) in a 2 dram vial was added 4,4,4',4',5,5,5',5'-octamethyl-2,2'-bi(1,3,2-dioxaborolane) (0.062 g, 0.246 mmol) followed by Example 104A (0.050 g, 0.123 mmol). This mixture was then sparged with N$_2$ gas for 15 minutes. PdCl2(dppf) (8.99 mg, 0.012 mmol) was then added followed by degassing for 5 additional minutes. The vial was sealed and then heated at 85° C. for 3 hours. The reaction mixture was cooled to room temperature and then Na$_2$CO$_3$ (0.065 g, 0.614 mmol) was added followed by DME (1.0 mL), EtOH (0.5 mL) and water (0.5 mL). Next, 5-bromopyrimidin-4-amine (0.028 g, 0.160 mmol) was then added followed by degassing with N$_2$ for 10 minutes. Then, tetrakis(triphenylphosphine) palladium(0) (0.014 g, 0.012 mmol) was added followed by degassing for 5 additional minutes. The vial was then sealed and the mixture heated at 100° C. for 3 hours, cooled to room temperature and diluted with MeOH (5 mL). Filtration of this mixture and concentration gave the crude product as a brown solid. The crude material was purified by flash chromatography on silica using an ISCO system (12 g column, 40 mL/min, 0-7% MeOH in EtOAc over 20 minutes, rt=11 minutes) to give Example 104 (23 mg, 0.061 mmol, 49.5% yield) as an off-white solid. LC/MS (condition C): ret time=1.39 min, MS (ES): m/z=375.1 [M+H]$^+$. $^1$H NMR (500 MHz, DMSO-d6) δ ppm 6.98 (bs, 2 H); 7.41 (d, J=4.6 Hz, 1 H); 7.75 (dd, J=5.0, 8.8 Hz, 1 H); 7.84 (dt, J=2.9, 9.0 Hz, 1 H); 8.00 (dd, J=2.9, 9 Hz, 1 H); 8.31 (s, 1 H); 8.37 (s, 1 H); 8.53 (s, 1 H); 8.61 (d, J=4.6 Hz, 1 H).

Example 105

4-(5-(1-(4-fluorophenyl)-1H-pyrazolo[3,4-b]pyridin-4-yl)pyrimidin-4-yl)morpholine

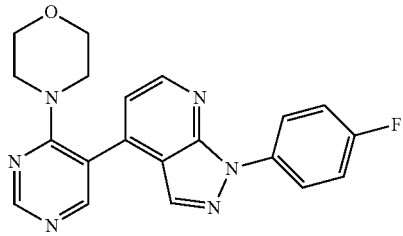

(105)

Intermediate 105A:
4-(5-iodopyrimidin-4-yl)morpholine

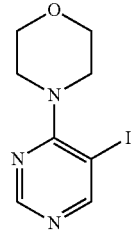

(105A)

To a vial containing a solution of 4-chloro-5-iodopyrimidine (0.200 g, 0.832 mmol) in DMF (1.333 mL) was added morpholine (0.291 mL, 3.33 mmol) followed by cesium carbonate (0.542 g, 1.664 mmol). The vial was sealed with a Teflon cap and heated at 90° C. for 80 min, then allowed to cool to room temperature. The reaction mixture was filtered through a disposable fritted funnel and the filter cake washed with $CH_2Cl_2$. The filtrate was concentrated, then further dried under high vacuum. Intermediate 105A: MS (ESI): m/z=292.0 $[M+H]^+$ HPLC Peak ret. T=1.23 minutes was product. (HPLC conditions: Column:Luna C18 4.6×30 mm 3 u A:10:90 $H_2O$:ACN $NH_4OAc$/B:10:90 $H_2O$:ACN $NH_4OAc$; 0%-95% B in 2 min; 4 mL/min flow).

Intermediate 105B: 1-(4-fluorophenyl)-4-(4,4,5,5-tetramethyl-1,3,2-dioxaborolan-2-yl)-1H-pyrazolo[3,4-b]pyridine

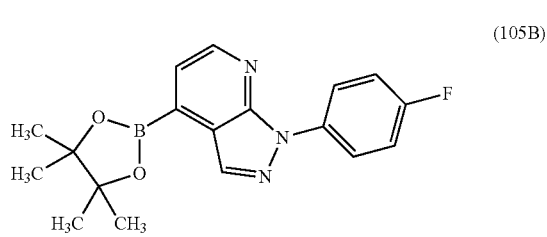 [SMILES: CC1(C)OB(c2ccnc3c2cnn3-c2ccc(F)cc2)OC1(C)C]

(105B)

A vial was charged with bis(acetonitrile)palladium(II) chloride (1.038 mg, 4.00 μmol), dicyclohexyl(2',6'-dimethoxybiphenyl-2-yl)phosphine (3.28 mg, 8.00 μmol), and Intermediate 2A (0.068 g, 0.200 mmol). The vial was capped with a rubber septum and then evacuated and back-filled with $N_2$ (this sequence was carried out a total of 2 times). Dioxane (0.120 mL) was added via syringe, through the septum, followed by the addition of triethylamine (0.084 mL, 0.600 mmol) and 4,4,5,5-tetramethyl-1,3,2-dioxaborolane (0.044 mL, 0.300 mmol) dropwise. The septum was then replaced with a Teflon screw valve, and the vial sealed. The reaction mixture was heated at 110° C. After 14 h, the reaction mixture was allowed to cool to room temperature. The reaction mixture was filtered through a disposable fritted funnel and the filter cake washed with $CH_2Cl_2$. The filtrate was concentrated to afford the title compound as a yellow solid. Intermediate 105B: MS (ESI): m/z=340.2 $[M+H]^+$ HPLC Peak ret. T=2.00 minutes was product. (HPLC conditions: Column:Luna C18 4.6×30 mm 3 u A:10:90 $H_2O$:ACN $NH_4OAc$/B:10:90 $H_2O$:ACN $NH_4OAc$; 0%-95% B in 2 min; 4 mL/min flow).

Example 105

A reaction flask was charged with tetrakis(triphenylphosphine)palladium(0) (5.78 mg, 5.00 μmol), Intermediate 105B (33.9 mg, 0.100 mmol), sodium carbonate (42.4 mg, 0.400 mmol), and Intermediate 105A (30.6 mg, 0.105 mmol). The mixture was stirred at room temperature for 10 min under $N_2$, then DME (Ratio: 2.0, Volume: 373 μl), EtOH (Ratio: 1.000, Volume: 187 μl), and water (Ratio: 1.000, Volume: 187 μl) were added sequentially. The resultant mixture was heated at 90° C. overnight. After 16 h, the reaction mixture was allowed to cool to room temperature, then quenched with water and diluted with EtOAc. The layers were separated and the aqueous phase was extracted with EtOAc (3×). The organic phases were combined, dried over $Na_2SO_4$, filtered, and concentrated to afford a residue. The crude material was purified via preparative LC/MS with the following conditions: Column: Waters XBridge C18, 19×250 mm, 5-μm particles; Guard Column: Waters XBridge C18, 19×10 mm, 5-μm particles; Mobile Phase A: 5:95 acetonitrile:water with 10-mM ammo-nium acetate; Mobile Phase B: 95:5 acetonitrile:water with 10-mM ammonium acetate; Gradient: 20-55% B over 25 minutes, then a 5-minute hold at 100% B; Flow: 20 mL/min. Fractions containing Example 105 were combined and dried via centrifugal evaporation to give 8.1 mg (21%) of the title compound. LC/MS (condition D): purity=99%, ret time=2.182 min, MS (ES): m/z=377.1 $[M+H]^+$.

Example 106

1-(4-fluorophenyl)-4-(4-(2,2,2-trifluoroethoxy)pyrimidin-5-yl)-1H-pyrazolo[3,4-b]pyridine

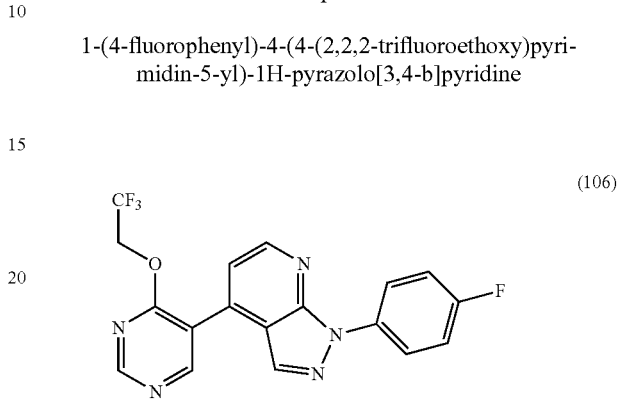

(106)

Intermediate 106A:
5-iodo-4-(2,2,2-trifluoroethoxy)pyrimidine

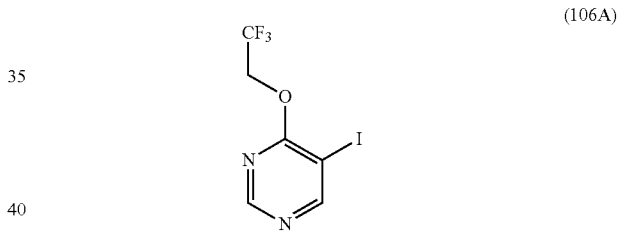

(106A)

To a solution of 2,2,2-trifluoroethanol (0.672 mL, 9.36 mmol) in THF (18.08 mL), was added, portionwise, at 0° C., NaH (0.424 g, 10.61 mmol). The reaction mixture was stirred at 0° C. for 30 min. Then 4-chloro-5-iodopyrimidine (1.5 g, 6.24 mmol) was added and the reaction mixture was refluxed for about 1 h. The reaction mixture was allowed to cool to room temperature, then a saturated aqueous solution of $NH_4Cl$ was added. The mixture was diluted with EtOAc and the layers were separated. The aqueous phase was extracted with EtOAc (2×). The combined organics were washed with brine (1×), dried over $Na_2SO_4$, filtered, and concentrated in vacuo to afford Intermediate 106A as a yellow solid. MS (ESI): m/z=304.7 $[M+H]^+$ HPLC Peak ret. T=0.88 minutes was product. (HPLC conditions: Condition F).

Example 106

A reaction flask was charged with tetrakis(triphenylphosphine)palladium(0) (5.78 mg, 5.00 μmol), Intermediate 105B (33.9 mg, 0.100 mmol), sodium carbonate (42.4 mg, 0.400 mmol), and Intermediate 106A (31.9 mg, 0.105 mmol). The mixture was stirred at room temperature for 10 min under $N_2$, then DME (Ratio: 2.0, Volume: 373 μl), EtOH (Ratio: 1.000, Volume: 187 μl), and water (Ratio: 1.000, Volume: 187 μl) were added sequentially. The resultant mixture was heated at 90° C. for 17 h. Next, the reaction mixture was cooled to room temperature, quenched with water and diluted with EtOAc. The layers were separated and the aqueous phase was extracted with EtOAc (3×). The organic phases were combined, dried over Na$_2$SO$_4$, filtered, and concentrated to afford a residue. The crude material was purified via preparative LC/MS with the following conditions: Column: Waters XBridge C18, 19×250 mm, 5-µm particles; Guard Column: Waters XBridge C18, 19×10 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 30-65% B over 25 minutes, then a 5-minute hold at 100% B; Flow: 20 mL/min. Fractions containing the desired product were combined and dried via centrifugal evaporation to give 3.0 mg (7%) of the title compound. LC/MS (condition D); ret time=2.803 min, MS (ES): m/z=389.95 [M+H]$^+$.

Example 107

5-(1-(4-fluorophenyl)-1H-pyrazolo[3,4-b]pyridin-4-yl)-N-(2,2,2-trifluoroethyl)pyrimidin-4-amine

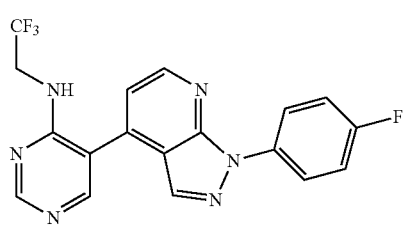

(107)

Intermediate 107A:
5-iodo-N-(2,2,2-trifluoroethyl)pyrimidin-4-amine

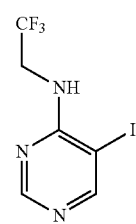

(107A)

To a solution of 4-chloro-5-iodopyrimidine (0.250 g, 1.040 mmol) and 2,2,2-trifluoroethanamine (0.216 g, 2.184 mmol) in EtOH (volume: 2.080 ml) was added Hunig's Base (0.200 ml, 1.144 mmol). The reaction mixture was heated in a microwave for 4 h at 120° C. and then allowed to cool to room temperature. The solvent was evaporated. The crude material was dissolved in a minimal amount of CH$_2$Cl$_2$ to be chromatographed. Purification of the crude material by silica gel chromatography using an ISCO machine (24 g column, 35 mL/min, 0-90% EtOAc in hexanes over 25 min, ret. T=12 min) gave Intermediate 107A (0.188 g, 0.614 mmol, 59.1% yield) as a yellow residue. MS (ESI): m/z=303.9 [M+H]$^+$ HPLC Peak ret. T=1.26 minutes was product. (HPLC conditions: Column:Luna C18 4.6×30 mm 3 u A:10:90 H$_2$O:ACN NH$_4$OAc/B:10:90 H$_2$O:ACN NH$_4$OAc; 0%-95% B in 2 min; 4 mL/min flow).

Example 107

A vial was charged with tetrakis(triphenylphosphine)palladium(0) (11.56 mg, 10.00 µmol), Intermediate 105B (67.8 mg, 0.200 mmol), sodium carbonate (85 mg, 0.800 mmol), and Intermediate 107A (63.6 mg, 0.210 mmol). The mixture was stirred at room temperature for 10 min under N$_2$, then DME (Ratio: 2.0, Volume: 746 µl), EtOH (Ratio: 1.000, Volume: 373 µl), and water (Ratio: 1.000, Volume: 373 µl) were added sequentially. The resultant mixture was heated at 90° C. for 17 h. Next, the reaction mixture was allowed to cool to room temperature, then quenched with water and diluted with EtOAc. The layers were separated and the aqueous phase was extracted with EtOAc (3×). The organic phases were combined, dried over Na$_2$SO$_4$, filtered, and concentrated to afford a brown residue. The crude material was dissolved in a minimal amount of CH$_2$Cl$_2$ to be chromatographed. Purification of the crude material by silica gel chromatography using an ISCO machine (12 g column, 30 mL/min, 0-90% EtOAc in hexanes over 18 min, ret. T=10 min) gave the product at approximately 87% purity. Product-containing fractions were combined and the solvent was evaporated to afford a yellow solid (33 mg). The solid was dissolved in a minimal amount of CH$_2$Cl$_2$ (required a few drops of acetone and MeOH) and re-chromatographed by silica gel chromatography using an ISCO machine (12 g column, 30 mL/min, 0-30% acetone in CH$_2$Cl$_2$ over 25 min, ret. T=7 min), which gave Example 107 (7 mg, 0.017 mmol, 8.74% yield) as a yellow solid. ESI MS (M+H)$^+$=389.1. HPLC Peak ret. T=2.665 minutes was product. Purity=97%. (HPLC conditions: YMC S5 ODS column, 4.6×50 mm. 4 min gradient (0-100% B), 4 mL/min, 40° C. @ 220 nm, solvent A: 0.2% H$_3$PO$_4$ in 10% MeOH-90% H$_2$O solvent B: 0.2% H$_3$PO$_4$ in 90% MeOH-10% H$_2$O).

Example 108

N-cyclopropyl-5-(1-(2,4-difluorophenyl)-1H-pyrazolo[3,4-b]pyridin-4-yl)pyrimidin-4-amine

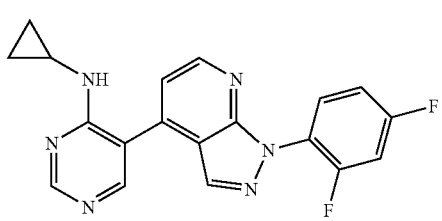

(108)

Intermediate 108A:
N-cyclopropyl-5-iodopyrimidin-4-amine

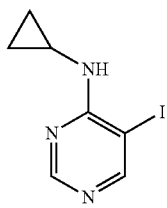 [SMILES: Ic1cncnc1NC1CC1]

To a vial containing a solution of 4-chloro-5-iodopyrimidine (0.400 g, 1.664 mmol) in DMF (Volume: 2.67 ml) was added cyclopropanamine (0.461 ml, 6.65 mmol) followed by cesium carbonate (1.084 g, 3.33 mmol). The vial was sealed with a Teflon cap and heated at 90° C. for 3 h, then allowed to cool to room temperature. The reaction mixture was filtered through a disposable fritted funnel and the filter cake washed with EtOAc. The filtrate was diluted with $H_2O$ and the layers were separated. The organic phase was washed with $H_2O$ (2×). The combined aqueous phases were back-extracted with EtOAc (3×). All organics were combined, dried over $Na_2SO_4$, filtered, and concentrated to afford an orange residue. The crude material was dissolved in a minimal amount of $CH_2Cl_2$ to be chromatographed. Purification of the crude material by silica gel chromatography using an ISCO machine (40 g column, 40 mL/min, 20-70% EtOAc in hexanes over 19 min, ret. T=13.5 min) gave Intermediate 108A (348 mg, 1.320 mmol, 79% yield) as a yellow solid. MS (ESI): m/z=262.0 [M+H]$^+$ HPLC Peak ret. T=1.47 minutes was product. (HPLC conditions: Column:Luna C18 4.6×30 mm 3 u A:10:90 $H_2O$:ACN $NH_4OAc$/B:10:90 $H_2O$:ACN $NH_4OAc$; 0%-95% B in 2 min; 4 mL/min flow).

Example 108

To a vial was added Intermediate 108A (52.2 mg, 0.200 mmol), sodium carbonate (47.1 mg, 0.444 mmol), and tetrakis(triphenylphosphine)palladium(0) (11.79 mg, 10.20 µmol). The vial was capped with a rubber septum and then evacuated and backfilled with $N_2$. Intermediate 63A (27.5 mg, 0.100 mmol) in DMSO (1 mL) was added via syringe through the septum, followed by the addition of DME (Ratio: 2.5, Volume: 560 µl), EtOH (Ratio: 1.2, 269 µl), and water (Ratio: 1.0, Volume: 224 µl) sequentially. The reaction mixture was sparged with $N_2$, then the septum was replaced with a Teflon screw valve, and the vial sealed. The resultant mixture was heated at 105° C. for 15 h. Next, the reaction mixture was allowed to cool to room temperature, then quenched with water and diluted with EtOAc. The layers were separated and the aqueous phase was extracted with EtOAc (5×). The organic phases were combined, washed with $H_2O$ (2×), dried over $Na_2SO_4$, filtered, and concentrated to afford a dark brown residue. The crude material was purified via preparative LC/MS with the following conditions: Column: Waters XBridge C18, 19×250 mm, 5-µm particles; Guard Column: Waters XBridge C18, 19×10 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 0-100% B over 25 minutes, then a 5-minute hold at 100% B; Flow: 20 mL/min. Fractions containing the desired product were combined and dried via centrifugal evaporation. The material was further purified via preparative LC/MS with the following conditions: Column: Waters XBridge C18, 19×250 mm, 5-µm particles; Guard Column: Waters XBridge C18, 19×10 mm, 5-µm particles; Mobile Phase A: 5:95 acetonitrile:water with 10-mM ammonium acetate; Mobile Phase B: 95:5 acetonitrile:water with 10-mM ammonium acetate; Gradient: 0-40% B over 25 minutes, then a 15-minute hold at 40% B; Flow: 20 mL/min. Fractions containing the Example 108 were combined and dried via centrifugal evaporation to give 7.1 mg (19%) of the title compound. LC/MS (condition D): purity=99%, ret time=1.888 min, MS (ES): m/z=365.1 [M+H]$^+$.

Biological Assays

The pharmacological properties of the compounds of this invention may be confirmed by a number of biological assays.

The exemplified biological assays, which follow, have been carried out with compounds of the invention and/or salts thereof.

CYP17 Total SPA Assay

The assays were performed in U-bottom 384-well optiplates. The final assay volume was 15 µl prepared from 7.5 µl additions of microsomes (prepared as a high-speed pellet from homogenized HEK2 cells stably transfected with CYP17), substrates (3 H-Pregnenolone and NADPH) and test compounds in assay buffer (50 mM Potassium phosphate pH 7.2, 10% glycerol). The reaction was initiated by the combination of the microsomes and substrates in wells containing compound. The reaction was incubated at room temperature for 45 minutes and terminated by adding 7.5 µl of 0.2N HCl to each well. Following an incubation period of 10 minutes, anti-DHEA-coated SPA beads were added to the terminated reaction. The plate was sealed and incubated overnight with shaking at 4° C. The beads were allowed to settle in the plate for 1 hour and the plate read on a Topcount (Perkin-Elmer) plate reader.

Inhibition data were calculated by comparison to no enzyme control reactions for 100% inhibition and vehicle-only reactions for 0% inhibition. The final concentration of reagents in the assays are NADPH, 2 mM; 3H-Pregnenolone, 1 uM; microsomes, 1.25 ug/ml; Anti-DHEA-SPA beads (0.125 mg/well) in 0.5% Triton X-100 and DMSO, 0.05%. Dose response curves were generated to determine the concentration required inhibiting 50% of enzyme activity ($IC_{50}$). Compounds were dissolved at 10 mM in dimethylsulfoxide (DMSO) and evaluated at eleven concentrations, each in duplicate. $IC_{50}$ values were derived by non-linear regression analysis.

Table 5 below lists the $IC_{50}$ values for the following examples of this invention measured in the Total CYP17 SPA Assay hereinabove. The compounds of the present invention, as exemplified by the following examples, showed Human CYP17 SPA $IC_{50}$ values of less than 1 µM.

TABLE 5

Human CYP17 Inhibition

| Example # | Human CYP17 SPA $IC_{50}$ Value (nM) |
|---|---|
| 2 | 186 |
| 8 | 23 |
| 9 | 5.9 |
| 33 | 393 |
| 39 | 100 |
| 46 | 10 |
| 55 | 807 |
| 64 | 15 |
| 67 | 5.8 |
| 70 | 105 |
| 72 | 525 |
| 80 | 18 |
| 84 | 89 |
| 88 | 622 |
| 93 | 159 |
| 96 | 704 |
| 100 | 320 |
| 106 | 123 |

CYP17 Lyase Assay

Human CYP17 was expressed in HEK293 cells and microsomal preparations were made and subsequently used as the source of enzyme in the lyase assay. The reaction consists of 200 nM [3H]-Hydroxypregnenolone (ARC), 200 nM 17-Hydroxypregnenolone (Sigma), 2 mM NADPH (Cal-Biochem), and CYP17-HEK293 microsomes which were incubated in the presence of DMSO or test compounds for 20 minutes at room temperature. Compounds were dissolved in DMSO and serially diluted. The reaction was stopped by the addition of 0.2 N HCl and the product was captured using anti-mouse YSi SPA beads (GE) conjugated to an anti-DHEA monoclonal antibody (Abcam). Signal intensity determined by a Packard Top Count was used to calculate percent inhibition and $IC_{50}$ values.

Cyp17 Hydroxylase Assay

E. coli was transformed to express active human CYP17 and membranes prepared from the transformed E. coli were used as the source of enzyme. The reaction was carried out in a 50 uL final volume containing 200 nM hCYP17 membranes, 25 μM Pregnenolone (Sigma), 7 mM NADPH (Cal-Biochem), 1 μM cytochrome P450 reductase (Invitrogen), and 50 mM sodium phosphate buffer, pH 7.3. The $IC_{50}$ determination of compounds dissolved in 100% DMSO was done by serial dilution into the assay buffer to a final concentration of 0.2% DMSO. The reaction was incubated at 37° C. for 120 minutes and stopped by the addition of 200 uL of 0.02N HCl in acetonitrile. Samples were then spun at 750000 g and 200 uL of the supernatant was transferred to a clean tube for analysis. The product of the reaction, 17 alpha pregnenolone, was measured via LC/MS.

Cyp17 HEK293 Cell Based Assay

HEK293 cells were stably transfected with human Cyp17 and individual clones analyzed for Cyp17 enzymatic activity via LC/MS. A single clone showing robust activity was selected and scaled up. Cells were seeded in 96 well plates and a serial dilution of compounds dissolved in DMSO was added to the cells. Following an incubation of 4 hours, reactions were neutralized by the addition of 200 ul of acetonitrile containing 0.5 uM pregnenolone as tracer. Plates were spun down at 2K for 15 minutes and supernatants transferred to siliconized 96 well plates. The end product of the reaction DHEA was analyzed via LC/MS.

1-Day Cyno PK/PD Study Protocol

Animals: All procedures involving animals and their care were conducted in conformity with the guidelines that are in compliance with the Bristol-Myers Squibb Institutional Animal Care and Use Committee. Fully mature male cynomolgus monkeys (>4 yrs of age; 5-6 kg) were from an in-house colony. All the monkeys used had chronically implanted femoral vein access ports. For oral studies, all animals were fasted overnight prior to dosing and were fed 4 hr after dosing. All animals had free access to water and were conscious throughout the study.

Drug: For all oral pharmacokinetic studies in cynomolgus monkeys, the tested compound was formulated in polyethylene glycol (PEG 400): water (80:20, v:v) at concentrations of 1-5 mg/mL.

Drug Treatment: The tested compound was administered by oral gavage to cynomolgus monkeys.

Sampling: Blood samples were collected from the femoral port, at 15, 30, and 45 min, and 1, 2, 4, 6, 8, 12, 24, 30, and 48 hr after oral administration. All blood samples were collected into syringes containing sodium heparin. The plasma fraction was immediately separated by centrifugation (14,000 rpm, 10 min, 4° C.), frozen on dry ice, and stored at −20° C. until the samples were analyzed.

Analysis of Tested Compound: Plasma samples were thawed and treated with two volumes of acetonitrile containing internal standard. After centrifugation to remove precipitated proteins, an aliquot of supernatant was analyzed by LC/MS/MS. Analysis of Steroids. Plasma samples were thawed, and assayed in accordance with package insert instructions for the following kits: Coat-A-Count total testosterone solid phase RIA kit, Coat-A-Count total progesterone solid phase RIA kit, and Coat-A-Count total cortisol solid phase RIA kit (Diagnostic Product Corp, Siemens Healthcare Diagnostics, Deerfield, Ill.).

FIG. 1 shows the results of a 1-day PK/PD study in NHP cynomolgus monkeys with Example 67. Example 67 was formulated in 80% PEG-400/water at a volume of 1 mL/Kg and a dose of 1 mg/Kg. The formulation was then dosed orally at time=0 hours and blood samples were taken over a 24 hours period to monitor for drug exposure and testosterone levels. As shown in FIG. 1, testosterone levels were reduced to ~30 ng/dL after a single oral dose of Example 67, consistent with an inhibitor of CYP17 lyase.

The invention claimed is:

1. A compound of Formula (I)

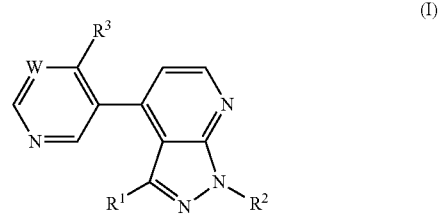

(I)

or pharmaceutically acceptable salts thereof, wherein:

W is $CR^4$ or N;

$R^1$ is H, halo, or $C_{1-6}$alkyl substituted with zero to 4 $R^a$;

$R^2$ is:
  (i) $C_{1-6}$alkyl substituted with zero to 4 $R^a$;
  (ii) $C_{3-6}$cycloalkyl substituted with zero to 4 $R^a$;
  (iii) aryl substituted with zero to 6 $R^b$;
  (iv) heterocyclyl substituted with zero to 6 $R^c$; or
  (v) heteroaryl substituted with zero to 6 $R^c$;

$R^3$ is:
  (i) H, halo, —CN, —$OR^d$, —$NR^eR^e$, or —$C(O)OR^f$;
  (ii) $C_{1-6}$alkyl substituted with zero to 4 $R^a$;
  (iii) $C_{3-6}$cycloalkyl substituted with zero to 4 $R^a$;
  (iv) aryl substituted with zero to 6 $R^b$;
  (v) heterocyclyl substituted with zero to 6 $R^c$; or
  (vi) heteroaryl substituted with zero to 6 $R^c$;

$R^4$ is:
  (i) H, halo, —CN, —$OR^d$, —$NR^eR^e$, or —$C(O)OR^f$;
  (ii) $C_{1-6}$alkyl substituted with zero to 4 $R^a$; or
  (iii) $C_{3-6}$cycloalkyl substituted with zero to 4 $R^a$;

each $R^a$ is independently halo, —OH, —CN, $C_{3-6}$cycloalkyl, $C_{1-2}$fluoroalkyl, $C_{1-2}$fluoroalkoxy, morpholinyl, and/or phenyl substituted with zero to 5 $R^b$;

each $R^b$ is independently halo, —OH, —CN, $C_{1-4}$alkyl, $C_{3-6}$cycloalkyl, $C_{1-2}$fluoroalkyl, $C_{1-2}$alkoxy, $C_{1-2}$fluoroalkoxy, —$NH_2$, —$NH(CH_3)$, —$NH(CH_2CF_3)$, —$N(CH_3)_2$, —$N(CH_3)(CH_2CF_3)$, —C(O)OH, —$S(O)_2$($C_{1-4}$alkyl), —$S(O)_2NR^fR^f$, azetidine, and/or pyrrolidine;

each $R^c$ is independently halo, —CN, —OH, $C_{1-4}$alkyl, $C_{3-6}$cycloalkyl, $C_{1-2}$fluoroalkyl, —$OCF_3$, —$OCHF_2$, —$OCH_2F$, —$NH_2$, —$NH(CH_3)$, —$NH(CH_2CF_3)$, —$N(CH_3)_2$, —$N(CH_3)(CH_2CF_3)$, azetidine, and/or pyrrolidine, or two $R^c$ attached to the same atom can form =O;

$R^d$ is:
  (i) $C_{1-4}$alkyl substituted with zero to 4 $R^a$;
  (ii) $C_{3-6}$cycloalkyl substituted with zero to 4 $R^a$;
  (iii) aryl substituted with zero to 6 $R^b$;
  (iv) heterocyclyl substituted with zero to 6 $R^c$; or
  (v) heteroaryl substituted with zero to 6 $R^c$;

each $R^e$ is independently:
(i) H;
(ii) $C_{1-4}$alkyl substituted with zero to 4 $R^a$; and/or
(iii) $C_{3-6}$ cycloalkyl substituted with zero to 4 $R^a$; and
each $R^f$ is independently H and/or $C_{1-4}$alkyl;
with the provisos that:
(i) if $R^1$ is H, W is CH, and $R^3$ is —CH$_3$, then $R^2$ is not:

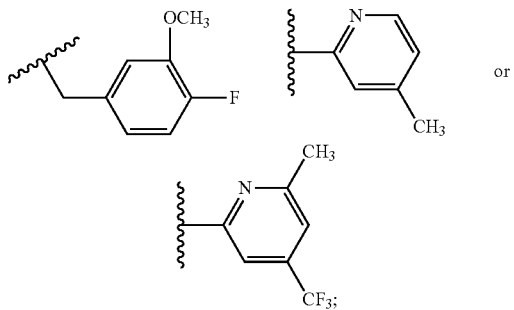

or (ii) if $R^1$ is H, W is N, and $R^3$ is CF$_3$, then $R^2$ is not:

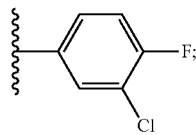 [SMILES: *c1ccc(F)c(Cl)c1]

and (iii) if $R^1$ is H, W is N, and $R^3$ is —NH$_2$, then $R^2$ is not:

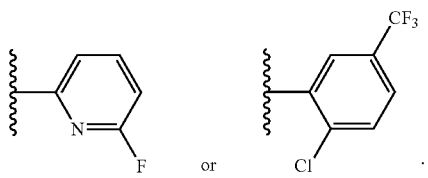 [SMILES: *c1cccc(F)n1 ; "or" ; *c1cc(C(F)(F)F)ccc1Cl]

2. A compound according to claim 1 or pharmaceutically acceptable salts thereof, wherein:
$R^1$ is H, F, Cl, or —CH$_3$;
$R^2$ is:
(i) $C_{1-4}$alkyl substituted with zero to 4 $R^a$;
(ii) $C_{4-6}$ cycloalkyl substituted with zero to 2 $R^a$;
(iii) phenyl or naphthalenyl substituted with zero to 6 $R^b$;
(iv) monocyclic heterocyclyl substituted with zero to 4 $R^c$; or
(v) 5- to 6-membered or 9- to 10-membered heteroaryl substituted with zero to 4 $R^c$;
$R^3$ is:
(i) H, F, Cl, Br, —CN, —OR$^d$, —NR$^e$R$^e$, or —C(O)OR$^f$;
(ii) $C_{1-3}$alkyl substituted with zero to 4 $R^a$;
(iii) $C_{3-6}$ cycloalkyl substituted with zero to 2 $R^a$;
(iv) phenyl substituted with zero to 5 $R^b$;
(v) monocyclic heterocyclyl substituted with zero to 5 $R^c$; or
(vi) monocyclic heteroaryl substituted with zero to 3 $R^c$;
$R^4$ is:
(i) H, F, Cl, Br, —CN, —OR$^d$, —NR$^e$R$^e$, or —C(O)OR$^f$;
(ii) $C_{1-3}$alkyl substituted with zero to 4 $R^a$; or
(iii) $C_{3-6}$ cycloalkyl substituted with zero to 2 $R^a$;

each $R^a$ is independently F, Br, —OH, —CN, $C_{3-6}$cycloalkyl, $C_{1-2}$fluoroalkyl, —OCF$_3$, —OCHF$_2$, morpholinyl, and/or phenyl substituted with zero to 3 $R^b$;
each $R^b$ is independently F, Cl, Br, $C_{1-4}$alkyl, $C_{1-2}$fluoroalkyl, $C_{1-2}$alkoxy, —OCF$_3$, —OCHF$_2$, —OCH$_2$F, —NH$_2$, and/or —S(O)$_2$NR$^f$R$^f$;
each $R^c$ is independently F, Cl, Br, —CN, —OH, $C_{1-2}$alkyl, $C_{1-2}$fluoroalkyl, —OCF$_3$, —NH$_2$, —NH(CH$_3$), and/or —N(CH$_3$)$_2$, or two $R^c$ attached to the same atom can form =O;
$R^d$ is $C_{1-2}$alkyl or $C_{1-2}$fluoroalkyl;
each $R^e$ is independently:
(i) H;
(ii) $C_{1-2}$alkyl or $C_{1-2}$fluoroalkyl; and/or
(iii) $C_{3-6}$ cycloalkyl; and
each $R^f$ is independently H and/or $C_{1-2}$alkyl.

3. A compound according to claim 1 or pharmaceutically acceptable salts thereof, wherein:
$R^1$ is H or Cl;
$R^2$ is:
(i) $C_{1-4}$alkyl substituted with zero to 3 $R^a$;
(ii) $C_{4-6}$ cycloalkyl;
(iii) phenyl substituted with zero to 4 $R^b$;
(iv) tetrahydropyran or tetrahydrothiophenyl substituted with zero to 4 $R^c$; or
(v) oxazolyl, thiazolyl, pyridinyl, or benzothiazolyl, each substituted with zero to 2 $R^c$;
$R^3$ is:
(i) H, Cl, —OCH$_3$, —OCH$_2$CF$_3$, —NHR$^e$, or —C(O)OCH$_3$;
(ii) —CH$_3$, —CF$_3$, —CHCl$_2$, or —CH$_2$CN;
(iii) cyclopropyl;
(iv) oxetanyl, azetidinyl, or morpholinyl, each substituted with zero to 2 $R^c$; or
(v) triazolyl;
$R^4$ is H;
each $R^a$ is independently —OH, cyclohexyl, —CF$_3$, morpholinyl, and/or phenyl substituted with zero to 2 $R^b$;
each $R^b$ is independently F, Cl, Br, $C_{1-3}$alkyl, —CF$_3$, $C_{1-2}$alkoxy, —OCF$_3$, —C(O)OH, and/or —S(O)$_2$NH$_2$;
each $R^c$ is independently F, Cl, Br, —CN, —OH, —CH$_3$, —CF$_3$, or two $R^c$ attached to the same atom can form =O; and
$R^e$ is H, —CH$_2$CF$_3$, or cyclopropyl.

4. The compound according to claim 3 or pharmaceutically acceptable salt thereof, wherein:
$R^1$ is H or Cl;
$R^2$ is:
(i) butyl or $C_{4-6}$cycloalkyl;
(ii) $C_{1-2}$alkyl substituted with —OH, —CF$_3$, cyclohexyl, or morpholinyl;
(iii) phenyl substituted with zero to 4 substituents independently selected from F, Cl, Br, $C_{1-3}$alkyl, $C_{1-2}$alkoxy, —CF$_3$, —OCF$_3$, —C(O)OH, and/or —S(O)$_2$NH$_2$;
(iv) benzyl substituted with zero to 2 substituents independently selected from F, Cl, and/or —OCH$_3$;
(v) thiazolyl, oxazolyl, or pyridinyl, each substituted with zero to two substituents independently selected from F, Cl, Br, —CH$_3$, —CF$_3$, and/or —CN;
(vi) benzothiazolyl; or
(vii) tetrahydropyranyl or tetramethylene sulfonyl; and
$R^3$ is H, Cl, —CH$_3$, —CF$_3$, —CHCl$_2$, —CH$_2$CN, —OCH$_3$, —OCH$_2$CF$_3$, —NH$_2$, —C(O)OCH$_3$, —NH(cyclopropyl), —NH(CH$_2$CF$_3$), cyclopropyl, morpholinyl, triazolyl, azetidinyl, difluoro azetidinyl, hydroxyazetidinyl, or hydroxy oxetanyl.

5. The compound according to claim 4 or pharmaceutically acceptable salt thereof, wherein: W is CH.

6. The compound according to claim 4 or pharmaceutically acceptable salt thereof, wherein: W is N.

7. The compound according to claim 1 or pharmaceutically acceptable salt thereof, wherein said compound is selected from 3-(4-(4-methoxypyridin-3-yl)-1H-pyrazolo[3,4-b]pyridin-1-yl)benzenesulfonamide (1); 1-(4-fluorophenyl)-4-(4-methylpyrimidin-5-yl)-1H-pyrazolo[3,4-b]pyridine (2); 1-(4-fluorophenyl)-4-(4-methylpyridin-3-yl)-1H-pyrazolo[3,4-b]pyridine (3); 3-(4-(4-aminopyrimidin-5-yl)-1H-pyrazolo[3,4-b]pyridin-1-yl)benzenesulfonamide (4); 1-(4-fluorophenyl)-4-(4-(trifluoromethyl)pyridin-3-yl)-1H-pyrazolo[3,4-b]pyridine (5); 1-(4-fluorophenyl)-4-(4-methoxypyridin-3-yl)-1H-pyrazolo[3,4-b]pyridine (6); 4-(4-cyclopropylpyrimidin-5-yl)-1-(4-fluorophenyl)-1H-pyrazolo[3,4-b]pyridine (7); 5-(1-(4-fluorophenyl)-1H-pyrazolo[3,4-b]pyridin-4-yl)pyrimidin-4-amine (8); 3-(3-(1-(4-fluorophenyl)-1H-pyrazolo[3,4-b]pyridin-4-yl)pyridin-4-yl) oxetan-3-ol (9); 4-(4-chloropyridin-3-yl)-1-(4-fluorophenyl)-1H-pyrazolo[3,4-b]pyridine (10); 1-(4-fluorophenyl)-4-(pyridin-3-yl)-1H-pyrazolo[3,4-b]pyridine (11); methyl 3-(1-(4-fluorophenyl)-1H-pyrazolo[3,4-b]pyridin-4-yl)isonicotinate (12); 1-(2,4-difluorophenyl)-4-(4-methylpyridin-3-yl)-1H-pyrazolo[3,4-b]pyridine (13); 4-(4-methylpyridin-3-yl)-1-(pyridin-2-yl)-1H-pyrazolo[3,4-b]pyridine (14); 1-(2,5-dichlorophenyl)-4-(4-methylpyridin-3-yl)-1H-pyrazolo[3,4-b]pyridine (15); 4-(4-methylpyridin-3-yl)-1-(2,4,6-trifluorophenyl)-1H-pyrazolo[3,4-b]pyridine (16); 1-(2,5-difluorophenyl)-4-(4-methylpyridin-3-yl)-1H-pyrazolo[3,4-b]pyridine (17); 1-(3-chloro-4-fluorophenyl)-4-(4-methylpyridin-3-yl)-1H-pyrazolo[3,4-b]pyridine (18); 1-(2-chloro-5-(trifluoromethyl)phenyl)-4-(4-methylpyridin-3-yl)-1H-pyrazolo[3,4-b]pyridine (19); 1-(3-fluoro-2-methoxyphenyl)-4-(4-methylpyridin-3-yl)-1H-pyrazolo[3,4-b]pyridine (20); 1-tert-butyl-4-(4-methylpyridin-3-yl)-1H-pyrazolo[3,4-b]pyridine (21); 3-(4-(4-methylpyridin-3-yl)-1H-pyrazolo[3,4-b]pyridin-1-yl)benzoic acid (22); 4-(4-methylpyridin-3-yl)-1-(3-(trifluoromethyl)pyridin-2-yl)-1H-pyrazolo[3,4-b]pyridine (23); 1-(cyclohexylmethyl)-4-(4-methylpyridin-3-yl)-1H-pyrazolo[3,4-b]pyridine (24); 1-(3-chloropyridin-2-yl)-4-(4-methylpyridin-3-yl)-1H-pyrazolo[3,4-b]pyridine (25); 1-(3-chloro-2-methylphenyl)-4-(4-methylpyridin-3-yl)-1H-pyrazolo[3,4-b]pyridine (26); 1-cyclohexyl-4-(4-methylpyridin-3-yl)-1H-pyrazolo[3,4-b]pyridine (27); 1-isobutyl-4-(4-methylpyridin-3-yl)-1H-pyrazolo[3,4-b]pyridine (28); 1-(4-fluorobenzyl)-4-(4-methylpyridin-3-yl)-1H-pyrazolo[3,4-b]pyridine (29); 1-(3-chloro-5-fluorophenyl)-4-(4-methylpyridin-3-yl)-1H-pyrazolo[3,4-b]pyridine (30); 4-(2-(4-(4-methylpyridin-3-yl)-1H-pyrazolo[3,4-b]pyridin-1-yl)ethyl) morpholine (31); 1-(5-chloropyridin-2-yl)-4-(4-methylpyridin-3-yl)-1H-pyrazolo[3,4-b]pyridine (32); 4-(4-methylpyridin-3-yl)-1-(tetrahydro-2H-pyran-4-yl)-1H-pyrazolo[3,4-b]pyridine (33); 2-(4-(4-methylpyridin-3-yl)-1H-pyrazolo[3,4-b]pyridin-1-yl)benzo[d]thiazole (34); 4-(4-methylpyridin-3-yl)-1-(2-(trifluoromethyl)phenyl)-1H-pyrazolo[3,4-b]pyridine (35); 4-(4-methylpyridin-3-yl)-1-(2-methylpyridin-4-yl)-1H-pyrazolo[3,4-b]pyridine (36); 1-cyclobutyl-4-(4-methylpyridin-3-yl)-1H-pyrazolo[3,4-b]pyridine (37); 1-(6-fluoropyridin-2-yl)-4-(4-methylpyridin-3-yl)-1H-pyrazolo[3,4-b]pyridine (38); 4-(4-methylpyridin-3-yl)-1-(5-(trifluoromethyl)pyridin-2-yl)-1H-pyrazolo[3,4-b]pyridine (39); 2-methyl-5-(4-(4-methylpyridin-3-yl)-1H-pyrazolo[3,4-b]pyridin-1-yl)oxazole-4-carbonitrile (40); 1-(3-methoxyphenyl)-4-(4-methylpyridin-3-yl)-1H-pyrazolo[3,4-b]pyridine (41); 1-(4-methoxybenzyl)-4-(4-methylpyridin-3-yl)-1H-pyrazolo[3,4-b]pyridine (42); 1-(2-methoxybenzyl)-4-(4-methylpyridin-3-yl)-1H-pyrazolo[3,4-b]pyridine (43); 1-(3-methoxybenzyl)-4-(4-methylpyridin-3-yl)-1H-pyrazolo[3,4-b]pyridine (44); 1-benzyl-4-(4-methylpyridin-3-yl)-1H-pyrazolo[3,4-b]pyridine (45); 1-(3-bromopyridin-2-yl)-4-(4-methylpyridin-3-yl)-1H-pyrazolo[3,4-b]pyridine (46); 4-(4-methylpyridin-3-yl)-1-o-tolyl-1H-pyrazolo[3,4-b]pyridine (47); 1-(2-methoxyphenyl)-4-(4-methylpyridin-3-yl)-1H-pyrazolo[3,4-b]pyridine (48); 4-(4-(4-methylpyridin-3-yl)-1H-pyrazolo[3,4-b]pyridin-1-yl)benzenesulfonamide (49); 1-(5-fluoro-2-methylphenyl)-4-(4-methylpyridin-3-yl)-1H-pyrazolo[3,4-b]pyridine (50); 4-(4-methylpyridin-3-yl)-1-(3-(trifluoromethyl)phenyl)-1H-pyrazolo[3,4-b]pyridine (51); 1-(3,4-difluorophenyl)-4-(4-methylpyridin-3-yl)-1H-pyrazolo[3,4-b]pyridine (52); 1-(2-isopropylphenyl)-4-(4-methylpyridin-3-yl)-1H-pyrazolo[3,4-b]pyridine (53); 1-(2-ethoxyphenyl)-4-(4-methylpyridin-3-yl)-1H-pyrazolo[3,4-b]pyridine (54); 1-(2-chloro-6-fluorobenzyl)-4-(4-methylpyridin-3-yl)-1H-pyrazolo[3,4-b]pyridine (55); 1-(1,1-dioxidotetrahydrothiophen-3-yl)-4-(4-methylpyridin-3-yl)-1H-pyrazolo[3,4-b]pyridine (56); 1-(2,6-difluorophenyl)-4-(4-methylpyridin-3-yl)-1H-pyrazolo[3,4-b]pyridine (57); 1-(5-chloro-2-fluorophenyl)-4-(4-methylpyridin-3-yl)-1H-pyrazolo[3,4-b]pyridine (58); 1-(2-bromophenyl)-4-(4-methylpyridin-3-yl)-1H-pyrazolo[3,4-b]pyridine (59); 1-(3-bromophenyl)-4-(4-methylpyridin-3-yl)-1H-pyrazolo[3,4-b]pyridine (60); 4-(4-(dichloromethyl)pyridin-3-yl)-1-(2,4-difluorophenyl)-1H-pyrazolo[3,4-b]pyridine (61); 3-(1-(2,4-difluorophenyl)-1H-pyrazolo[3,4-b]pyridin-4-yl)pyridin-4-amine (62): 2-(3-(1-(2,4-difluorophenyl)-1H-pyrazolo[3,4-b]pyridin-4-yl)pyridin-4-yl)acetonitrile (63); 1-(2,4-difluorophenyl)-4-(4-methylpyrimidin-5-yl)-1H-pyrazolo[3,4-b]pyridine (64); 4-(4-(Azetidin-1-yl)pyridin-3-yl)-1-(2,4-difluorophenyl)-1H-pyrazolo[3,4-b]pyridine (65); 4-(4-(azetidin-1-yl)pyrimidin-5-yl)-1-(2,4-difluorophenyl)-1H-pyrazolo[3,4-b]pyridine (66); 5-(1-(2,4-difluorophenyl)-1H-pyrazolo[3,4-b]pyridin-4-yl)pyrimidin-4-amine (67); 1-(5-(1-(2,4-difluorophenyl)-1H-pyrazolo[3,4-b]pyridin-4-yl)pyrimidin-4-yl)azetidin-3-ol (68); 5-(1-(2,3,5,6-tetrafluorophenyl)-1H-pyrazolo[3,4-b]pyridin-4-yl)pyrimidin-4-amine (69); 5-(1-(2,3,4-trifluorophenyl)-1H-pyrazolo[3,4-b]pyridin-4-yl)pyrimidin-4-amine (70); 5-(1-(3-bromopyridin-2-yl)-1H-pyrazolo[3,4-b]pyridin-4-yl)pyrimidin-4-amine (71); 5-(1-(pyridin-2-yl)-1H-pyrazolo[3,4-b]pyridin-4-yl)pyrimidin-4-amine (72); 5-(1-(3-(trifluoromethyl)pyridin-2-yl)-1H-pyrazolo[3,4-b]pyridin-4-yl)pyrimidin-4-amine (73); 5-(1-(2,6-difluorophenyl)-1H-pyrazolo[3,4-b]pyridin-4-yl)pyrimidin-4-amine (74); 5-(1-(3-chloro-5-fluorophenyl)-1H-pyrazolo[3,4-b]pyridin-4-yl)pyrimidin-4-amine (75); 5-(1-(2-(trifluoromethyl)phenyl)-1H-pyrazolo[3,4-b]pyridin-4-yl)pyrimidin-4-amine (76); 5-(1-(2,4,6-trifluorophenyl)-1H-pyrazolo[3,4-b]pyridin-4-yl)pyrimidin-4-amine (77); 5-(1-(2-chloro-4-fluorophenyl)-1H-pyrazolo[3,4-b]pyridin-4-yl)pyrimidin-4-amine (78); 3-(4-(4-aminopyridin-3-yl)-1H-pyrazolo[3,4-b]pyridin-1-yl)benzenesulfonamide (79); 3-(4-(4-methylpyridin-3-yl)-1H-pyrazolo[3,4-b]pyridin-1-yl)benzenesulfonamide (80); 1-(3-fluorophenyl)-4-(4-methylpyridin-3-yl)-1H-pyrazolo[3,4-b]pyridine (81); 1-(2-chloro-4-fluorophenyl)-4-(4-methylpyridin-3-yl)-1H-pyrazolo[3,4-b]pyridine (82); 2-(4-(4-methylpyridin-3-yl)-1H-pyrazolo[3,4-b]pyridin-1-yl) ethanol (83); 4-(4-methylpyridin-3-yl)-1-(2,2,2-trifluoroethyl)-1H-pyrazolo[3,4-b]pyridine (84); 4-(4-methylpyridin-3-yl)-1-phenyl-1H-pyrazolo[3,4-b]pyridine (85); 1-(5-methylpyridin-2-yl)-4-(4-methylpyridin-3-yl)-1H-pyrazolo[3,4-b]pyridine (86); 2-(4-(4-methylpyridin-3-yl)-1H-pyrazolo[3,4-b]pyridin-1-yl)thiazole (87); 4-methyl- 2-(4-(4-methylpyridin-3-yl)-1H-pyrazolo[3,4-b]pyridin-1-yl)thiazole (88); N-cyclopropyl-5-(1-(4-fluorophenyl)-1H-pyrazolo[3,4-b]pyridin-4-yl)pyrimidin-4-amine (89); 5-(1-(2,4-difluorophenyl)-1H-pyrazolo[3,4-b]pyridin-4-yl)-N-(2,2,2-trifluoroethyl)pyrimidin-4-amine (90); 4-(4-(2 H-1,2,3-triazol-2-yl)pyrimidin-5-yl)-1-(2,4-difluorophenyl)-1H-pyrazolo[3,4-b]pyridine (91); 5-(3-chloro-1-(4-fluorophenyl)-1H-pyrazolo[3,4-b]pyridin-4-yl)pyrimidin-4-amine (92); 1-(2,4-difluorophenyl)-4-(4-(trifluoromethyl)pyrimidin-5-yl)-1H-pyrazolo[3,4-b]pyridine (93); 5-(1-(2-methoxyphenyl)-1H-pyrazolo[3,4-b]pyridin-4-yl)-4-pyrimidinamine (94); 5-(1-(3,4-difluorophenyl)-1H-pyrazolo[3,4-b]pyridin-4-yl)-4-pyrimidinamine (95); 5-(1-(3-chloro-4-fluorophenyl)-1H-pyrazolo[3,4-b]pyridin-4-yl)-4-pyrimidinamine (96); 5-(1-(2,5-difluorophenyl)-1H-pyrazolo[3,4-b]pyridin-4-yl)-4-pyrimidinamine (97); 5-(1-(2-(trifluoromethoxy)phenyl)-1H-pyrazolo[3,4-b]pyridin-4-yl)-4-pyrimidinamine (98); 1-(4-fluorophenyl)-4-(4-(trifluoromethyl)-5-pyrimidinyl)-1H-pyrazolo[3,4-b]pyridine (99); 1-(3,4-difluorophenyl)-4-(4-(trifluoromethyl)-5-pyrimidinyl)-1H-pyrazolo[3,4-b]pyridine (100); 1-(2,5-difluorophenyl)-4-(4-(trifluoromethyl)-5-pyrimidinyl)-1H-pyrazolo[3,4-b]pyridine (101); 4-(4-(3,3-difluoroazetidin-1-yl)pyrimidin-5-yl)-1-(4-fluorophenyl)-1H-pyrazolo[3,4-b]pyridine (102); 4-(4-(3,3-difluoroazetidin-1-yl)pyrimidin-5-yl)-1-(2,4-difluorophenyl)-1H-pyrazolo[3,4-b]pyridine (103); 5-(1-(4-fluoro-2-(trifluoromethyl) phenyl)-1H-pyrazolo[3,4-b]pyridin-4-yl)pyrimidin-4-amine (104); 4-(5-(1-(4-fluorophenyl)-1H-pyrazolo[3,4-b]pyridin-4-yl)pyrimidin-4-yl)morpholine (105); 1-(4-fluorophenyl)-4-(4-(2,2,2-trifluoroethoxy)pyrimidin-5-yl)-1H-pyrazolo[3,4-b]pyridine (106); 5-(1-(4-fluorophenyl)-1H-pyrazolo[3,4-b]pyridin-4-yl)-N-(2,2,2-trifluoroethyl)pyrimidin-4-amine (107); and N-cyclopropyl-5-(1-(2,4-difluorophenyl)-1H-pyrazolo[3,4-b]pyridin-4-yl)pyrimidin-4-amine (108).

8. A pharmaceutical composition, comprising; a pharmaceutically acceptable carrier and a compound according to claim 1 or pharmaceutically acceptable salts thereof.

\* \* \* \* \*